US008680296B2

(12) United States Patent
Goto et al.

(10) Patent No.: US 8,680,296 B2
(45) Date of Patent: Mar. 25, 2014

(54) LEAVING SUBSTITUENT-CONTAINING COMPOUND, PRODUCTS PRODUCED USING THE SAME, AND METHODS FOR PRODUCING THE PRODUCTS

(75) Inventors: Daisuke Goto, Kanagawa (JP); Satoshi Yamamoto, Kanagawa (JP); Toshiya Sagisaka, Kanagawa (JP); Takuji Kato, Fukuoka (JP); Takashi Okada, Kanagawa (JP); Masato Shinoda, Kanagawa (JP); Shinji Matsumoto, Kanagawa (JP); Masataka Mohri, Kanagawa (JP); Keiichiro Yutani, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 13/391,448

(22) PCT Filed: Sep. 9, 2010

(86) PCT No.: PCT/JP2010/065996
§ 371 (c)(1),
(2), (4) Date: Feb. 21, 2012

(87) PCT Pub. No.: WO2011/030918
PCT Pub. Date: Mar. 17, 2011

(65) Prior Publication Data
US 2012/0153271 A1    Jun. 21, 2012

(30) Foreign Application Priority Data

| Sep. 11, 2009 | (JP) | 2009-209911 |
| Jan. 12, 2010 | (JP) | 2010-004324 |
| Mar. 17, 2010 | (JP) | 2010-061591 |
| Jul. 20, 2010 | (JP) | 2010-162750 |
| Jul. 21, 2010 | (JP) | 2010-163865 |

(51) Int. Cl.
*C07D 495/02* (2006.01)
*H01J 1/62* (2006.01)

(52) U.S. Cl.
USPC ............ 549/50; 549/29; 549/41; 549/49; 313/504; 313/506; 257/40

(58) Field of Classification Search
USPC .............. 549/29, 41, 49, 50; 313/504, 506; 257/40
See application file for complete search history.

(56) References Cited

U.S. PATENT DOCUMENTS

| 4,316,985 | A |  | 2/1982 | Broadhurst et al. |
| 8,440,713 | B2 | * | 5/2013 | Goto et al. ............ 514/443 |
| 2006/0286314 | A1 |  | 12/2006 | Park et al. |
| 2009/0261300 | A1 |  | 10/2009 | Watanabe |
| 2010/0032655 | A1 |  | 2/2010 | Takimiya et al. |
| 2010/0065826 | A1 |  | 3/2010 | Takimiya et al. |

FOREIGN PATENT DOCUMENTS

| CN | 101528753 A | 9/2009 |
| CN | 101529609 A | 9/2009 |
| JP | 5 55568 | 3/1993 |
| JP | 7 72664 | 3/1995 |
| JP | 7 188234 | 7/1995 |
| JP | 2006 352143 | 12/2006 |
| JP | 2007 224019 | 9/2007 |
| JP | 2008 226959 | 9/2008 |
| JP | 2008 270843 | 11/2008 |
| JP | 2009 84555 | 4/2009 |
| JP | 2009 105336 | 5/2009 |
| JP | 2009 275032 | 11/2009 |
| KR | 10-2009-0074248 | 7/2009 |
| KR | 10-2009-0080042 | 7/2009 |
| TW | 200838866 A | 10/2008 |
| WO | 2006 077888 | 7/2006 |
| WO | 2008 026602 | 3/2008 |
| WO | 2008 047896 | 4/2008 |
| WO | 2008 050726 | 5/2008 |

OTHER PUBLICATIONS

Barnes, R.A., "N-Bromosuccinimide as a Dehydrogenating Agent," Journal of the American Chemical Society, vol. 70, No. 1, pp. 145-147 (Jan. 1948).
Dyall, L.K., et al., "Pyrolysis of Aryl Azides. XII* Mechanistic Implications of the Very Small Neighbouring Group Effects Across the 2,3-Bond of 2-Azidonaphthalene," Australian Journal of Chemistry, vol. 47, pp. 1031-1042, (1994).
Yamada, S., et al., "Asymmetric Acylation of sec-Alcohols with Twisted Amides Possessing Axial Chirality Induced by the Adjacent Asymmetric Center," The Journal of Organic Chemistry, vol. 64, No. 26, pp. 9365-9373, (1999).
Yamada, S., et al., "New Class of Pyridine Catalyst Having a Conformation Switch System: Asymmetric Acylation of Various sec-Alcohols," The Journal of Organic Chemistry, vol. 71, No. 18, pp. 6872-6880, (2006).
Tsang, W.S., et al., "Chemistry of anti- and syn-1,2:3.4-Naphthalene Dioxides and Their Potential Relevance as Metabolic Intermediates," The Journal of Organic Chemistry, vol. 47, No. 27, pp. 5339-5353, (1982).

(Continued)

*Primary Examiner* — Golam M M Shameem
(74) *Attorney, Agent, or Firm* — Oblon, Spivak, McClelland, Maier & Neustadt, L.L.P.

(57) ABSTRACT

A leaving substituent-containing compound including a partial structure represented by the following General Formula (I): where a pair of $X_1$ and $X_2$ or a pair of $Y_1$ and $Y_2$ each represent a hydrogen atom; the other pair each represent a group selected from the group consisting of a halogen atom and a substituted or unsubstituted acyloxy group having one or more carbon atoms; a pair of the acyloxy groups represented by the pair of $X_1$ and $X_2$ or the pair of $Y_1$ and $Y_2$ may be identical or different, or may be bonded together to form a ring; $R_1$ to $R_4$ each represent a hydrogen atom or a substituent; and $Q_1$ and $Q_2$ each represent a hydrogen atom, a halogen atom or a monovalent organic group, and may be bonded together to form a ring.

4 Claims, 5 Drawing Sheets

(56) References Cited

OTHER PUBLICATIONS

Rosario, C.A., et al., "Synthesis of Potential Metabolites of Dibenz[a,j]acridine: Dihydro Diols and Phenols," The Journal of Organic Chemistry, vol. 52, No. 6, pp. 1064-1072, (1987).

Nelson, S.F., et al., "Temperature-independent transport in high-mobility pentacene transistors," Applied Physics Letters, vol. 72, No. 15, pp. 1854-1856, (Apr. 13, 1998).

Takimiya, K., et al., "2,7-Diphenyl[1]benzothieno[3,2-b]benzothiophene, A New Organic Semiconductor for Air-Stable Organic Field-Effect Transistors with Mobilities up to 2.0 cm$^2$ V$^{-1}$ s$^{-1}$," Journal of the American Chemical Society, vol. 128, No. 39, pp. 12604-12605, (2006).

Ebata, H., et al., "Highly Soluble [1]Benzothieno[3,2-b]benzothiophene (BTBT) Derivatives for High-Performance, Solution-Processed Organic Field-Effect Transitors," Journal of the American Chemical Society, vol. 129, No. 51, pp. 15732-15733, (2007).

Herwig, P.T., et al., "A Soluble Pentacene Precursor: Synthesis, Solid-State Conversion into Pentacene and Application in a Field-Effect Transistor**," Advanced Materials, vol. 11, No. 6, pp. 480-483, (1999).

Shea, P.B., et al., "Solution-processed nickel tetrabenzopophyrin thin-film transistors," Journal of Applied Physics, vol. 100, pp. 34502-1-34502-7, (2006).

Aramaki, S., et al. "Solution-processible organic semiconductor for transistor applications: Tetrabenzoporphyrin," Applied Physics Letters, vol. 84, No. 12, pp. 2085-2087 (Mar. 22, 2004).

Murphy A.R., et al., "Organic Thin Film Transistors from a Soluble Oligothiophene Derivative Containing Thermally Removable Solubilizing Groups," Journal of the American Chemical Society, vol. 126, No. 6, pp. 1596-1597, (2004).

Erenler, R., et al., "Synthesis of hydroxy, epoxy, nitrato and methoxy derivatives of tetralins and naphthalenes," Journal of Chemical Research, vol. 12, pp. 753-757, (Dec. 2006).

Zambounis, J.S., et al., "Latent pigments activated by heat," Nature, vol. 388, p. 131, (Jul. 10, 1997).

International Search Report Issued Oct. 19, 2010 in PCT/JP10/65996 Filed Sep. 9, 2010.

Combined Office Action and Search Report issued Apr. 25, 2013 in Taiwanese Patent Application No. 099130655 with English language translation.

Todd C. Henninger, et al., "Stereodivergent Routes from Tyrosine to the 7-(R) and 7-(S) Diastereomers of the 7-Hydroxy-2,3,7,7a-Tetrahydroindole Ring Found in Gliotoxin", Tetrahedrom, vol. 52, No. 46, 1996, pp. 14403-14418.

Office Action issued Sep. 13, 2013 in Korean Application No. 10-2012-7006410 (With English Translation).

Extended Search Report issued Sep. 12, 2013 in European Application No. 10815507.8.

Roland Köster, et al., "Reaktionen von Naphthalin, Anthracen und Phenanthren mit Tetraalkyldiboranen (6)", Chemische Berichte, vol. 122, No. 4, Apr. 1, 1989, pp. 677-686.

H. Yagi, et al., "Synthesis and Reactions of the Highly Mutagenic 7,8-Diol 9,10-Epoxides of the Carcinogen Benzo[a]pyrene", Journal of the American Chemical Society, vol. 99, No. 5, Mar. 1, 1977, pp. 1604-1611.

J.W. Cook, et al., "Oxidation of Anthracene by Osmium Tetroxide", Nature: International Weekly Journal of Science, vol. 161, No. 4085, Feb. 14, 1948, pp. 237-238.

Shoujun Chen, et al., "A Facile Synthesis of 9-Hydroxybenzo[a]Pyrene", Organic Preparations and Procedures International, vol. 29, No. 1, Jan. 1, 1997, pp. 131-134.

Marino Novi, et al., "*ipso*- and *tele*-Substitution Pathways in the Reactions of 1,3-Dimethyl-2,4-dinitro- and 1,3-Dimethyl-2 nitro-4-phenylsulphonylnaphthalene with Sodium Arenethiolates in Dimethyl Sulphoxide", J. Chem. Soc. Perkin Trans.1, Jan. 1, 1983, pp. 1145-1150.

M. Novi G. Guanti, et al, "Tele-Versus Normal Substitution in the Reaction of 1,4-Dialkyl-2,3-Dinitronaphthalenes with Sodium Arenethiolates in DMSO", Tetrahedron, Elsevier Science Publishers, vol. 35, Jan. 1, 1979, pp. 1783-1788.

Eug. Bamberger, et al., "Ueber die Einwirkung von Natrium und Alkohol auf α-Naphtonitril, Benzonitril und Tolunitril", Berichte Der Deutschen Chemischen Gesellschaft, vol. 20, Jan. 1, 1887, pp. 1703-1710.

Cited Reference 1; STN_Data.

Office Action issued Dec. 11, 2013, in Chinese Patent Application No. 2010840101, filed Sep. 9, 2010 (w/English translation).

Office Action issued Jan. 20, 2014, in Korean Patent Application No. 20127006410, filed Sep. 9, 2010 (w/English translation).

\* cited by examiner

LEAVING SUBSTITUENT-CONTAINING COMPOUND, PRODUCTS PRODUCED USING THE SAME, AND METHODS FOR PRODUCING THE PRODUCTS

TECHNICAL FIELD

The present invention relates to a leaving substituent-containing compound which is synthesized in a simple manner, which has high solubility, and which has substituents able to be efficiently eliminated upon application of external energy; to an organic semiconductor containing a compound formed therefrom; to a film containing the organic semiconductor; and to an organic electronic device containing the film. The leaving substituent-containing compound and the organic semiconductor of the present invention are useful, since organic electronic devices such as photoelectric conversion elements, thin-film transistor elements and light-emitting elements can be produced through a wet process using a solution.

The present invention relates to a method for producing a π-electron conjugated compound at high yield in a simple manner, the π-electron conjugated compound having a benzene ring and being produced by eliminating specific substituents from a π-electron conjugated compound precursor which is easily synthesized and has a cyclohexene ring with high solubility. The present invention also relates to a method for producing a film-like product containing the compound. The methods of the present invention for producing the benzene ring-containing π-electron conjugated compound and the film-like product containing the π-electron conjugated compound are useful in the production of organic electronics such as organic electronic devices (organic electroluminescence (EL) elements, organic semiconductors and organic solar cells) as well as the production of films of organic pigments and dyes.

BACKGROUND ART

In recent years, organic thin-film transistors using organic semiconductor materials have been intensively studied and developed.

Hitherto, organic semiconductive materials of low molecular weight have been reported, such as acene materials (e.g., pentacene) (see, for example, PTL 1 and NPL 1).

It has been reported that the organic thin-film transistors including an organic semiconductive layer formed of the aforementioned pentacene has relatively high charge mobility. However, these acene materials have extremely low solubility to common solvents. Therefore, these materials need to be vacuum-deposited to form a thin film as an organic semiconductive layer of an organic thin-film transistor. For this reason, these materials do not meet the demand in the art, which is to provide an organic semiconductive material that can be formed into a thin film by a simple wet process such as coating or printing.

As one of the acene-based materials such as pentacene, 2,7-diphenyl[1]benzothieno[3,2-b][1]benzothiophene having the following Structural Formula (1) (see PTL 2 and NPL 2), which is a derivative of benzothieno[3,2-b]benzothiophene, is deposited on a substrate having been treated with octadecyltrichlorosilane, so that the deposited product exhibits a mobility comparable to that of pentacene (approximately 2.0 cm$^2$/V·s) and has prolonged stability in the atmosphere.

However, this compound also needs to be vacuum-deposited similar to pentacene. Thus, this material also does not meet the demand in the art, which is to provide an organic semiconductive material that can be formed into a thin film by a simple process such as coating or printing.

The organic semiconductor materials can be easily formed into a thin film by a simple process such as a wet process, for example, printing, spin coating, ink jetting, or the like. The thin-film transistors using organic semiconductor materials also have an advantage over those using inorganic semiconductor materials in that the temperature of the production process can be lowered.

Thus, a film can be formed on a plastic substrate having a generally low heat resistance, so that electronic devices such as displays can be reduced in weight and cost. Further, the electronic devices are expected to be widely used by taking advantage of flexibility of the plastic substrate.

Moreover, 2,7-dialkyl[1]benzothieno[3,2-b][1]benzothiophene represented by the following General Formula (2), having liquid crystallinity and high solubility, can be applied by spin coating or casting (see PTL 2 and NPL 3). This compound is also a derivative which exhibits a mobility comparable to that of pentacene (approximately 2.0 cm$^2$/V·s) when thermally treated at a temperature equal to or lower than the temperature at which the compound shows a liquid crystal phase (about 100° C.).

However, the temperature at which this compound shows a liquid crystal phase is relatively low; i.e., about 100° C., and the film formed therefrom may be changed through thermal treatment after film formation. Thus, this compound poses a problem in process adaptability in production of organic semiconductor devices.

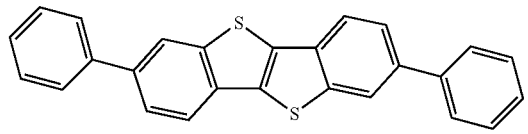

Structural Formula (1)

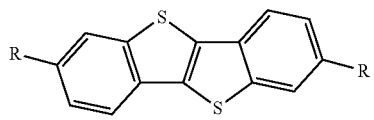

General Formula (2)

In recent years, a method of producing a field-effect transistor is reported, wherein a low-molecular-weight compound having high solvent solubility is used as a semiconductor precursor, which is dissolved in a solvent and the like, and applied so as to form a film by a coating process, and then the film is transformed to an organic semiconductor film. Intensive studies have been made on methods of converting the precursor to pentacene, a porphyrin-based compound, and a phthalocyanine-based compound through retro-Diels-Alder reaction (see, for example, PTLs 3 to 5 and NPLs 4 to 7).

As described in NPL 4, the charge mobility of organic semiconductor materials depends on the orderly molecular arrangement (e.g., crystallization) in organic material films. When a vapor-deposition method is employed, the molecular arrangement of the materials in the films can be surely obtained. Meanwhile, the organic materials with molecular arrangement generally have a low solubility to an organic solvent. That is, in the organic material films, the semiconductive property and film formability (through coating) are generally in a trade-off relation.

Thus, in only one possible method for attaining both satisfactorily, after a coating film has been formed from a coating liquid containing a semiconductor precursor having a solubility-imparting group, the precursor in the coating film is converted to an organic semiconductor material. When the disclosures of these literatures are deductively considered having such meanings, it can be said that these literatures have contributed in some degree to the improvement of the technology.

However, in the above-described example, a tetrachlorobenzene molecule or other molecules are eliminated from the pentacene precursor. Here, tetrachlorobenzene has a high boiling point and is hard to be removed from the reaction system. Additionally, there is concern for its toxicity.

Also, both porphyrin and phthalocyanine require complicate syntheses, and thus are used in narrow applications. Therefore, there is a need to develop a substituent-containing compound that can be synthesized in a simple manner.

Also, it has been proposed that, by applying an external stimulus to a precursor having a high solvent-solubility and sulfonate-based substituents so that the substituents are eliminated and substituted with hydrogen atoms, the precursor is converted to phthalocyanine (see, for example, PTL 6).

However, in this method, the sulfonate-based substituents have a high polarity and thus do not have sufficient solubility to an organic solvent having no polarity. In addition, sulfonic acid (eliminated component) has a high boiling point and difficult to remove from the reaction system. Furthermore, the temperature for conversion of the precursor is relatively high; i.e., at least 250° C. to 300° C. or higher, which is disadvantageous.

Also, it has been proposed that, by applying a thermal stimulus to a nitroester so that their substituents are eliminated, the nitroester is converted to a naphthalene derivative (see, for example, NPL 8). However, nitroesters such as nitroglycerine and nitrocellulose are unstable and explosive, and thus, such compounds are difficult to store for a long period of time.

Also, it has been proposed that an alkyl group-containing carboxylate is introduced to the end a-position of an oligothiophene for imparting solubilization, and then heat is applied to eliminate the carboxylate, thereby obtaining an olefin-substituted oligthiophene or an olefin-substituted [1]benzothieno[3,2-b][1]benzothiphene (see, for example, PTLs 7 and 8 and NPL 7).

In this method, the elimination occurs by heating to about 150° C. to about 250° C., and the converted compound has at its ends olefin groups (e.g., a vinyl group and a propenyl group) which involve cis-trans isomerization due to heat or light. Thus, the resultant material is problematically degraded in purity and/or crystallinity. In addition, such highly reactive olefin end groups allow the compound to decrease in stability to oxygen or water. Furthermore, one olefin group is thermally polymerized with another olefin group at higher temperatures.

In the above-described conventional compounds, there have been problems regarding solubility of the precursors, safety of the eliminated components, the conversion temperatures, and stability of the converted compounds. Also, it is difficult to obtain desired intermediate compounds in the synthesis processes of the conventional compounds.

π-Electron conjugated compounds, having a moiety in which double bonds and single bonds are alternatingly located, have a highly extended n-electron conjugation system, and thus, are excellent in hole transportability and electron transportability. Thus, such π-electron conjugated compounds have been used as electroluminescence materials and organic semiconductor materials (see, for example, PTLs 1 and 2 and NPLs 1 and 2) as well as organic dyes and pigments. The π-electron conjugated compounds widely used involve the following problem, for example. Specifically, most of the π-electron conjugated compounds are rigid and highly planar, and thus the intermolecular interaction is very strong. As a result, these compounds have poor solubility to water or organic solvents. For example, the organic pigments made of such conjugated compounds are unstable in dispersion due to aggregation of the pigments. Also, taking an example electroluminescence materials and organic semiconductor materials made of such conjugated compounds, a wet process (using a solution) is difficult to employ since the conjugated compounds are sparingly soluble. As a result, vapor phase-film formation (e.g., vacuum vapor deposition) is required to elevate the production cost and complicate the production process which is disadvantageous. Considering the coating on a larger area and the attainment of higher efficiency, the π-electron conjugated compounds are required to be applicable to wet processes using a coating liquid previously prepared by dissolving materials in a solvent (e.g., spin coating, blade coating, gravure printing, inkjet coating and dip coating). Meanwhile, the fact that intermolecular contact, rearrangement, aggregation and crystallization are easily attained since intermolecular interaction is very strong contributes to conductivity of the compounds. In general, the film-formability and the conductivity of the obtained film are often in a trade-off relation. This is one cause making difficult to employ the π-electron conjugated compounds.

In order to overcome the above-described problems, it has been proposed that an external stimulus is applied to an organic compound precursor (including π-electron conjugated compound precursors) having reactive substituents (which impart the solubility to the precursor) to thereby eliminate the substituents to obtain a compound of interest (see, for example, PTLs 9 and 10 and NPL 9). In this method, for example, a pigment precursor having a structure in which an amino group or an alcoholic or phenolic hydroxyl group is modified with a t-butoxycarbonyl group (a t-Boc group) is heated or treated otherwise to thereby eliminate the t-Boc group. However, some limitation is imposed on the compound employable in this method, since the substituent must be bonded to the nitrogen atom or oxygen atom. In addition, further improvement has been required in terms of stability of the precursor.

Meanwhile, in recent years, intensive studies have been made on a method of applying an external stimulus to a precursor having solvent-soluble bulky substituents so that the solvent-soluble bulky substituents are eliminated, and converting the precursor to a pentacene, a porphyrin-based compound, and a phthalocyanine-based compound (see, for example, PTLs 3 and 4, NPLs 4, 5, 6 and 7).

However, in the above-described example, a tetrachlorobenzene molecule or other molecules are eliminated from the pentacene precursor. Here, tetrachlorobenzene has a high boiling point and is hard to be removed from the reaction system. Additionally, there is concern for its toxicity. Also, both porphyrin and phthalocyanine require complicate syntheses, and thus are used in narrow applications. Therefore, there is a need to develop a substituent-containing compound that can be synthesized in a simple manner.

Also, it has been proposed that, by applying external stimulus to a precursor having a high solvent-solubility and sulfonate-based substituents so that the substituents are eliminated and substituted with hydrogen atoms, whereby the precursor is converted to phthalocyanine (see, for example, PTL 6).

However, in this method, the sulfonate-based substituents have a high polarity and thus do not have sufficient solubility to an organic solvent having no polarity. In addition, the temperature for conversion of the precursor is relatively high; i.e., at least 250° C. to 300° C. or higher, which is disadvantageous.

Also, it has been proposed that an alkyl group-containing carboxylate is introduced to the end of an oligothiophene for imparting solubilization, and then heat is applied to eliminate the carboxylate, thereby obtaining an olefin-substituted oligthiophene (see, for example, PTL 7 and NPL 8).

In this method, the elimination occurs by heating to about 150° C. to about 250° C., and the converted compound has at its ends olefin groups (e.g., a vinyl group and a propenyl group) which involve cis-trans isomerization due to heat or light. Thus, the resultant material is problematically degraded in purity and/or crystallinity. In addition, such highly reactive olefin end groups allow the compound to decrease in stability to oxygen or water. Furthermore, one olefin group is thermally polymerized with another olefin group at higher temperatures.

CITATION LIST

Patent Literature

PTL 1: Japanese Patent Application Laid-Open (JP-A) No. 05-055568
PTL 2: International Publication No. WO2006/077888
PTL 3: JP-A No. 2007-224019
PTL 4: JP-A No. 2008-270843
PTL 5: JP-A No. 2009-105336
PTL 6: JP-A No. 2009-84555
PTL 7: JP-A No. 2006-352143
PTL 8: JP-A No. 2009-275032
PTL 9: JP-A No. 07-188234
PTL 10: JP-A No. 2008-226959

Non Patent Literature

NPL 1: Appl. Phys. Lett. 72, p. 1854 (1998)
NPL 2: J. Am. Chem. Soc. 128, p. 12604 (2006)
NPL 3: J. Am. Chem. Soc. 129, p. 15732 (2007)
NPL 4: Adv. Mater., 11, p. 480 (1999)
NPL 5: J. Appl. Phys. 100, p. 034502 (2006)
NPL 6: Appl. Phys. Lett. 84, 12, p. 2085 (2004)
NPL 7: J. Am. Chem. Soc. 126, p. 1596 (2004)
NPL 8: J. Chem. Res. (12), p. 753-757 (2006)
NPL 9: Nature, 388, p. 131 (1997)

SUMMARY OF INVENTION

Technical Problem

The present invention has been made under such circumstances, and aims to provide a novel leaving substituent-containing compound which is synthesized in a simple manner, which has good storage stability and high solubility to an organic solvent, and which has substituents able to be efficiently eliminated upon application of external energy; an organic semiconductor material containing a compound which is formed at high yield by applying an external stimulus such as heat to the leaving substituent-containing compound without generating chemically unstable olefin end-groups. Also, in the present invention, the leaving substituent-containing compound is used for film formation as an organic semiconductor precursor, followed by converting to an organic semiconductor with, for example, heat, thereby obtaining, through a wet process using a solution, a continuous film of a sparingly-soluble organic photoconductor material. Thus, the present invention also aims to provide the continuous film and an organic electronic device containing the film (in particular, an organic thin-film transistor).

Furthermore, the present invention aims to provide a method for producing a benzene ring-containing π-electron conjugated compound, without generating chemically unstable olefin end-groups, including applying an external stimulus such as heat to a novel π-electron conjugated compound precursor which has high solubility to an organic solvent and is synthesized in a simple manner. On the basis of this method, the present invention also aims to provide a method for efficiently producing a continuous thin film of a sparingly-soluble π-electron conjugated compound. Further, the present invention aims to apply the thin film to an organic electronic device.

Solution to Problem

Means for solving the above-described problems are as follows.
<1> A leaving substituent-containing compound including:
a partial structure represented by the following General Formula (I):

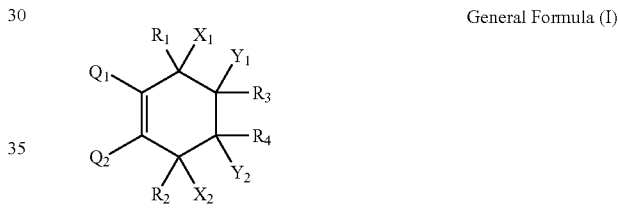

General Formula (I)

where a pair of $X_1$ and $X_2$ or a pair of $Y_1$ and $Y_2$ each represent a hydrogen atom; the other pair each represent a group selected from the group consisting of a halogen atom and a substituted or unsubstituted acyloxy group having one or more carbon atoms; a pair of the acyloxy groups represented by the pair of $X_1$ and $X_2$ or the pair of $Y_1$ and $Y_2$ may be identical or different, or may be bonded together to form a ring; $R_1$ to $R_4$ each represent a hydrogen atom or a substituent; and $Q_1$ and $Q_2$ each represent a hydrogen atom, a halogen atom or a monovalent organic group, and may be bonded together to form a ring.

<2> The leaving substituent-containing compound according to <1>, wherein the partial structure represented by General Formula (I) includes a partial structure represented by the following General Formula (III):

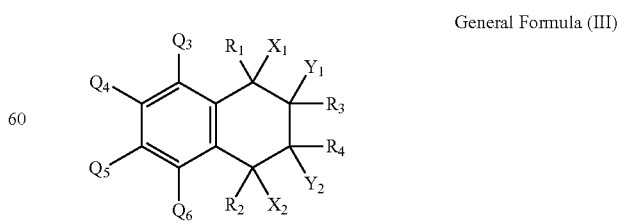

General Formula (III)

where $Q_3$ to $Q_6$ each represent a hydrogen atom, a halogen atom or a monovalent organic group; $Q_3$ and $Q_4$ may be bonded together to form a ring; $Q_4$ and $Q_5$ may be bonded together to form a ring; and $Q_5$ and $Q_6$ may be bonded together to form a ring.

<3> The leaving substituent-containing compound according to <1> or <2>, wherein the partial structure represented by General Formula (III) is a partial structure represented by the following General Formula (IV) or (V):

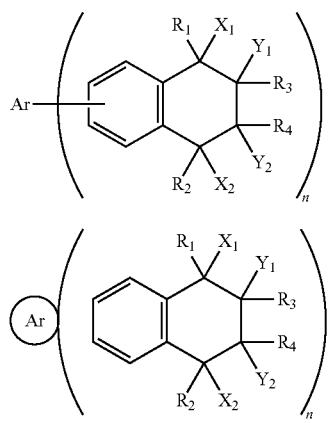

General Formula (IV)

General Formula (V)

where n is an integer of 1 or more, and when n is an integer of 2 or greater, a plurality of the substituents in parentheses may be identical or different; Ar represents an aryl group which may have a substituent or a heteroaryl group which may have a substituent; and Ar is linked via a covalent bond with or ring-fused with a skeleton of a cyclohexene derivative.

<4> The leaving substituent-containing compound according to <3>, wherein Ar is at least one compound selected from the group consisting of (i) aromatic hydrocarbon rings, aromatic heterocyclic rings, compounds in which one or more aromatic hydrocarbon rings are ring-fused with one or more aromatic heterocyclic rings, compounds in which two or more aromatic hydrocarbon rings are ring-fused together, and compounds in which two or more aromatic heterocyclic rings are ring-fused together; and (ii) compounds in which one or more aromatic hydrocarbon rings are linked via a covalent bond with one or more aromatic heterocyclic rings, compounds in which two or more aromatic hydrocarbon rings are linked together via a covalent bond, and compounds in which two or more aromatic heterocyclic rings are linked together via a covalent bond.

<5> The leaving substituent-containing compound according to <4> wherein the aromatic hydrocarbon ring is a benzene ring and the aromatic heterocyclic ring is a thiophene ring.

<6> The leaving substituent-containing compound according to any one of <3> to <5>, wherein Ar is any one of the following groups:

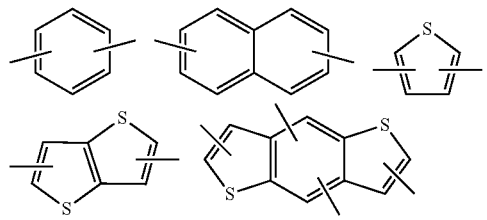

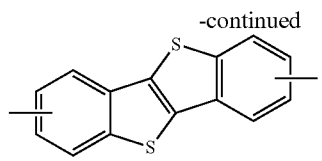

where each group may have at least one substituent selected from the group consisting of halogen atoms, C1-C18 alkyl groups, C1-C18 alkyloxy groups, C1-C18 alkylthio groups and aryl groups.

<7> An organic semiconductor material including:
a compound represented by the following General Formula (Ia),
wherein the compound is obtained by eliminating hydrogen halides or carboxylic acid derivatives represented by the following General Formulas (IIa) and (IIb) from the leaving substituent-containing compound according to any one of <1> to <6>:

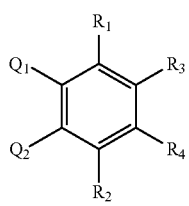

General Formula (Ia)

$X_1$—$Y_1$  General Formula (IIa)

$X_2$—$Y_2$  General Formula (IIb)

<8> An organic semiconductor film including:
the organic semiconductor material according to <7>.
<9> An organic electronic device including:
the organic semiconductor film according to <8>.
<10> The organic electronic device according to <9>, wherein the organic electronic device is an organic thin-film transistor.
<11> The organic electronic device according to <10>, wherein the organic thin-film transistor includes:
a pair of a first electrode and a second electrode,
the organic semiconductor film disposed between the first electrode and the second electrode, and
a third electrode,
wherein when a voltage is applied to the third electrode, the third electrode controls a current running through the organic semiconductor film.
<12> The organic electronic device according to <11>, wherein the organic thin-film transistor further includes an insulative film between the third electrode and the organic semiconductor film.
<13> A method for producing a film-like product, including:
forming a coating film on a substrate by coating the substrate with a coating liquid containing in a solvent a π-electron conjugated compound precursor represented by A-(B)$_m$, and
eliminating components represented by the following General Formulas (IIa) and (IIb) to form a π-electron conjugated compound represented by A-(C)$_m$ in the coating film,
wherein in A-(B)$_m$ and A-(C)$_m$, A represents a π-electron conjugated substituent, B represents a solvent-soluble substituent containing a structure represented by the following General Formula (I) as at least a partial structure, C represents a moiety containing a structure represented by the following General Formula (II) as at least a partial structure, and m is a natural number, and wherein the solvent-soluble substituent represented by B is linked via a covalent bond with the π-electron conjugated substituent represented by A where the covalent bond is formed with a carbon atom which is present on the solvent-soluble substituent represented by B and is other than those having substituents represented by $X_1$, $X_2$, $Y_1$ and $Y_2$; or is ring-fused with the π-electron conjugated substituent represented by A via the carbon atoms which are present on the solvent-soluble substituent represented by B and are other than those having substituents represented by $X_1$, $X_2$, $Y_1$ and $Y_2$,

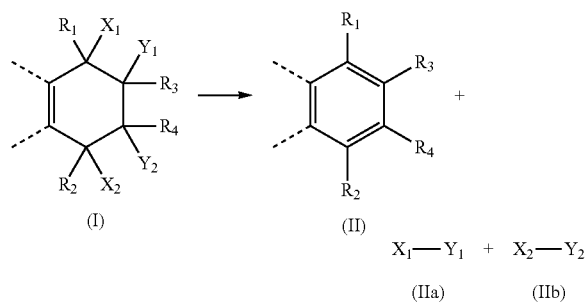

where a pair of $X_1$ and $X_2$ or a pair of $Y_1$ and $Y_2$ each represent a hydrogen atom; the other pair each represent a group selected from the group consisting of a halogen atom and a substituted or unsubstituted acyloxy group having one or more carbon atoms; a pair of the halogen atoms or the acyloxy groups represented by the pair of $X_1$ and $X_2$ or the pair of $Y_1$ and $Y_2$ may be identical or different, or may be bonded together to form a ring; and $R_1$ to $R_4$ each represent a hydrogen atom, a halogen atom or an organic group.

<14> The method for producing a film-like product according to <13>, wherein the substrate is coated with the coating liquid by a method selected from the group consisting of inkjet coating, spin coating, solution casting and dip coating.

<15> The method for producing a film-like product according to <13> or <14>, wherein the substituent represented by A is at least one π-electron conjugated compound selected from the group consisting of (i) aromatic hydrocarbon rings, aromatic heterocyclic rings, compounds in which one or more aromatic hydrocarbon rings are ring-fused with one or more aromatic heterocyclic rings, compounds in which two or more aromatic hydrocarbon rings are ring-fused together, and compounds in which two or more aromatic heterocyclic rings are ring-fused together; and (ii) compounds in which one or more aromatic hydrocarbon rings are linked via a covalent bond with one or more aromatic heterocyclic rings, compounds in which two or more aromatic hydrocarbon rings are linked together via a covalent bond, and compounds in which two or more aromatic heterocyclic rings are linked together via a covalent bond.

<16> The method for producing a film-like product according to any one of <13> to <15>, wherein the components represented by $X_1$-$Y_1$ and $X_2$-$Y_2$ and eliminated from the compound represented by A-(B)$_m$ include a hydrogen halide or carboxylic acid.

<17> The method for producing a film-like product according to any one of <14> to <16>, wherein the compound represented by A-(B)m has a solvent solubility, and the compound represented by A-(C)m and formed after elimination of the components has a solvent insolubility.

<18> The method for producing a film-like product according to any one of <13> to <17>, wherein the substituent represented by B contains a partial structure represented by the following General Formula (III), and the substituent represented by C contains a partial structure represented by the following General Formula (IV):

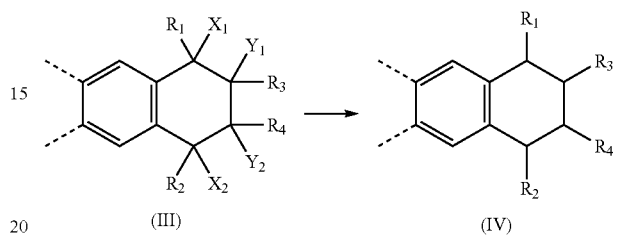

where a pair of $X_1$ and $X_2$ or a pair of $Y_1$ and $Y_2$ each represent a hydrogen atom; the other pair each represent a group selected from the group consisting of a halogen atom and a substituted or unsubstituted acyloxy group having one or more carbon atoms; a pair of the halogen atoms or the acyloxy groups represented by the pair of $X_1$ and $X_2$ or the pair of $Y_1$ and $Y_2$ may be identical or different, or may be bonded together to form a ring; and $R_1$ to $R_4$ each represent a hydrogen atom or a substituent.

<19> A method for producing a π-electron conjugated compound, including:

eliminating components represented by the following General Formulas (IIa) and (IIb) from a π-electron conjugated compound precursor represented by A-(B)m so as to form a π-electron conjugated compound represented by A-(C)m, wherein in A-(B)m and A-(C)m, A represents a π-electron conjugated substituent, B represents a solvent-soluble substituent containing a structure represented by the following General Formula (I) as at least a partial structure, C represents a moiety containing a structure represented by the following General Formula (II) as at least a partial structure, and m is a natural number, and wherein the solvent-soluble substituent represented by B is linked via a covalent bond with the π-electron conjugated substituent represented by A where the covalent bond is formed with a carbon atom other than those having substituents represented by $X_1$, $X_2$, $Y_1$ and $Y_2$, or is ring-fused with the π-electron conjugated substituent represented by A via other carbon atoms than those having substituents represented by $X_1$, $X_2$, $Y_1$ and $Y_2$,

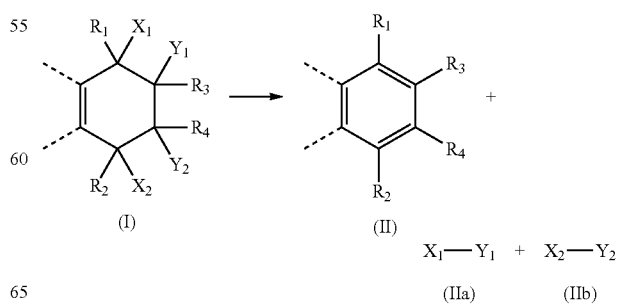

where a pair of $X_1$ and $X_2$ or a pair of $Y_1$ and $Y_2$ each represent a hydrogen atom; the other pair each represent a group selected from the group consisting of a halogen atom and a substituted or unsubstituted acyloxy group having one or more carbon atoms; a pair of the halogen atoms or the acyloxy groups represented by the pair of $X_1$ and $X_2$ or the pair of $Y_1$ and $Y_2$ may be identical or different, or may be bonded together to form a ring; and $R_1$ to $R_4$ each represent a hydrogen atom, a halogen atom or an organic group.

<20> The method for producing a π-electron conjugated compound according to <19>, wherein the substituent represented by A is at least one π-electron conjugated compound selected from the group consisting of (i) aromatic hydrocarbon rings, aromatic heterocyclic rings, compounds in which one or more aromatic hydrocarbon rings are ring-fused with one or more aromatic heterocyclic rings, compounds in which two or more aromatic hydrocarbon rings are ring-fused together, and compounds in which two or more aromatic heterocyclic rings are ring-fused together; and (ii) compounds in which one or more aromatic hydrocarbon rings are linked via a covalent bond with one or more aromatic heterocyclic rings, compounds in which two or more aromatic hydrocarbon rings are linked together via a covalent bond, and compounds in which two or more aromatic heterocyclic rings are linked together via a covalent bond.

<21> The method for producing a π-electron conjugated compound according to <19> or <20>, wherein the compound represented by A-(B)m has a solvent solubility, and the compound represented by A-(C)m and formed after the eliminating of the components has a solvent insolubility.

<22> The method for producing a π-electron conjugated compound according to any one of <19> to <21>, wherein the substituent represented by B contains a partial structure represented by the following General Formula (III), and the substituent represented by C contains a partial structure represented by the following General Formula (IV):

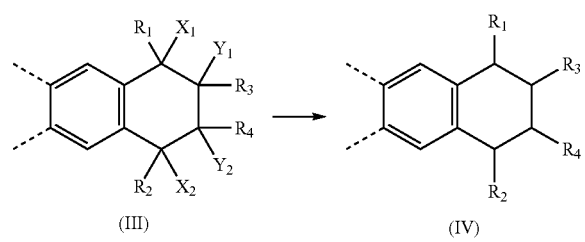

where a pair of $X_1$ and $X_2$ or a pair of $Y_1$ and $Y_2$ each represent a hydrogen atom; the other pair each represent a group selected from the group consisting of a halogen atom and a substituted or unsubstituted acyloxy group having one or more carbon atoms; a pair of the halogen atoms or the acyloxy groups represented by the pair of $X_1$ and $X_2$ or the pair of $Y_1$ and $Y_2$ may be identical or different, or may be bonded together to form a ring; and $R_1$ to $R_4$ each represent a hydrogen atom or a substituent.

<23> A π-electron conjugated compound obtained by the method according to any one of <19> to <22>.

The present invention can provide a leaving substituent-containing compound which is synthesized in a simple manner and has high solubility; and an organic semiconductor material having no unstable end substituents which is produced by eliminating the substituents from the leaving substituent-containing compound through elimination reaction.

Also, the present invention can provide an organic semiconductor film which is obtained through coating of a solution containing the leaving substituent-containing compound as an organic semiconductor precursor and through elimination reaction; and an organic electronic device containing the film (in particular, an organic thin-film transistor).

The production method of the present invention uses a solvent-soluble precursor (a raw material) of a π-electron conjugated compound, and thus, is suitably applicable to a wet process using a solution. In addition, by applying an external stimulus (such as heat and light) to the precursor so that the substituents imparting solvent solubility to the precursor are eliminated, a benzene ring-containing π-electron conjugated compound can be produced at high yield in a simple manner without generating unstable end substituents. Also, on the basis of this method, a π-electron conjugated compound having excellent properties and a thin film containing the π-electron conjugated compound in high purity can be produced.

DESCRIPTION OF EMBODIMENTS

Figure 1:
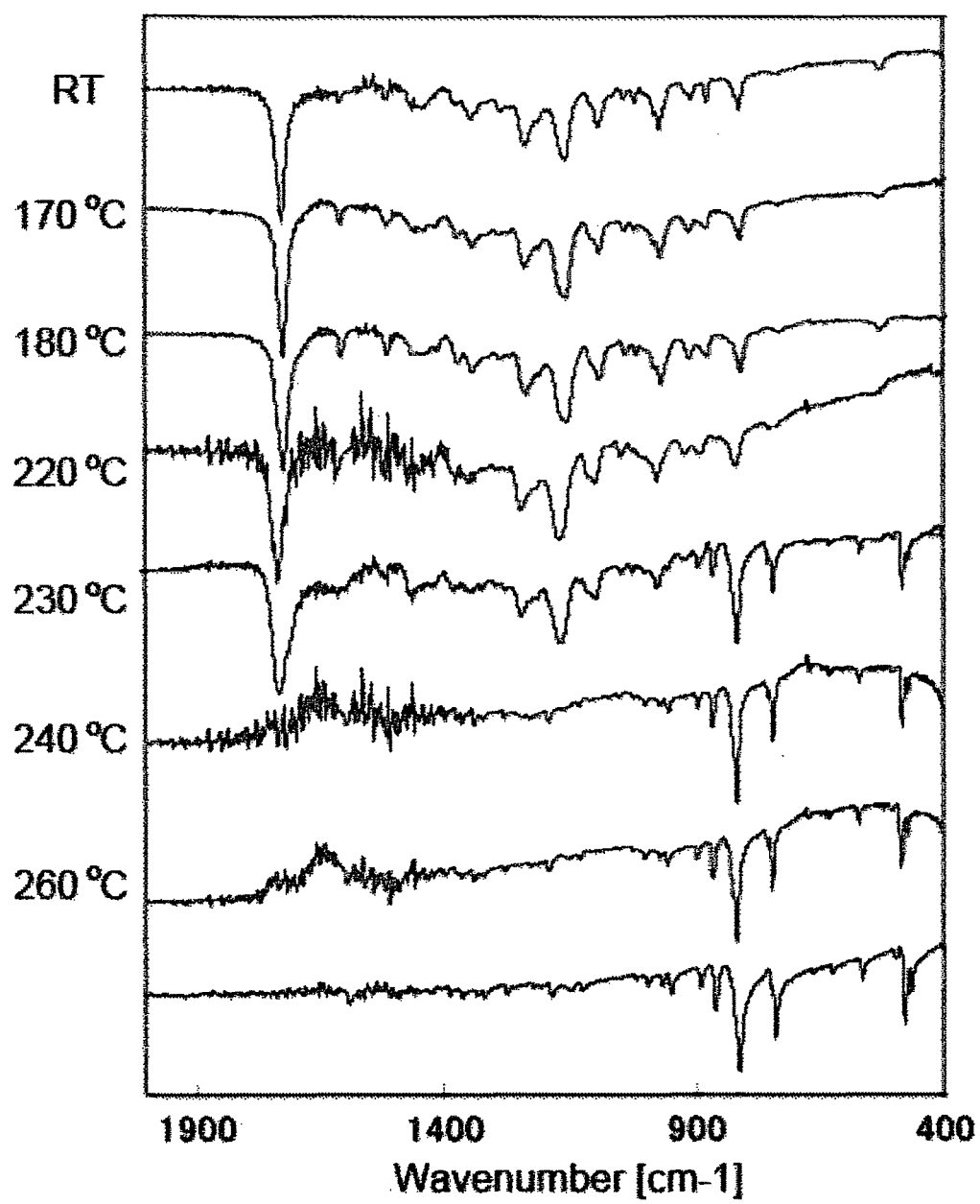
FIG. 1 illustrates IR spectra of Compounds 11 and 17 in which the horizontal axis indicates a wavenumber and the vertical axis indicates a transmittance (from up to bottom, spectra of Compound 11 before heating, and heated at 170° C., 180° C., 220° C., 230° C., 240° C. and 260° C.; and the spectrum of Compound 17).

Next, the present invention will be described referring to specific embodiments, which should not be construed as limiting the present invention thereto. The present invention can be variously made without departing the spirit and scope of the present invention.

(Leaving Substituent-Containing Compound and Compound Through Elimination Reaction)

A leaving substituent-containing compound of the present invention has specific solvent-soluble substituents. By applying an external stimulus to the leaving substituent-containing compound so as to eliminate the specific substituents, a compound of interest can be produced.

The specific solvent-soluble substituent (which is a substituent able to impart a solubility to a compound) has a cyclohexene structure represented by the following General Formula (I) or (III), which is substituted with halogen atoms or acyloxyl groups. Upon application of an external stimulus, specific leaving substituents (X₁, X₂) and (Y₁, Y₂) are eliminated from the solvent-soluble substituent in the form of components represented by General Formula (IIa) and (IIb), to thereby form a compound represented by General Formula (Ia) or (IIIa) in which the cyclohexene structure has been converted to a benzene ring.

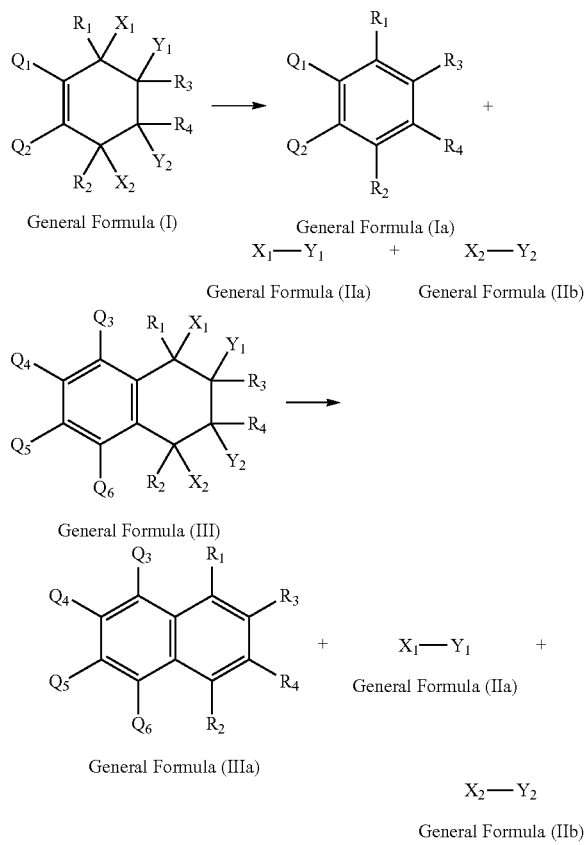

In General Formulas, a pair of X₁ and X₂ or a pair of Y₁ and Y₂ each represent a hydrogen atom; the other pair each represent a group selected from the group consisting of a halogen atom and a substituted or unsubstituted acyloxy group having one or more carbon atoms; a pair of the acyloxy groups represented by the pair of X₁ and X₂ or the pair of Y₁ and Y₂ may be identical or different, or may be bonded together to form a ring; R₁ to R₄ each represent a hydrogen atom, a halogen atom or an organic group; Q₁ to Q₆ each represent a monovalent organic group; Q₁ and Q₂ may be bonded together to form a ring; Q₃ and Q₄ may be bonded together to form a ring; Q₄ and Q₅ may be bonded together to form a ring; and Q₅ and Q₆ may be bonded together to form a ring;

Examples of the substituents represented by each of X₁, X₂, Y₁ and Y₂ include a hydrogen atom, a halogen atom and a substituted or unsubstituted acyloxy group having one or more carbon atoms.

Examples of the substituted or unsubstituted acyloxy group include a formyloxy group; those derived from linear or cyclic aliphatic carboxylic acids having two or more carbon atoms and optionally containing a halogen atom and carbonate half esters thereof; and those derived from carboxylic acids such as aromatic carboxylic acids having 4 or more carbon atoms and carbonate half esters thereof.

Specific examples of the acyloxy group include a formyloxy group, an acetoxy group, a propionyloxy group, a butylyloxy group, an isobutylyloxy group, a pivaloyloxy group, a pentanoyloxy group, a hexanoyloxy group, a lauroyloxy group, a stearoyloxy group, a chloroacetoxy group, a fluoroacetoxy group, a trifluoroacetyloxy group, 3,3,3-trifluoropropionyloxy group, a pentafluoropropionyloxy group, a cyclopropanoyloxy group, a cyclobutanoyloxy group, a cyclohexanoyloxy group, a benzoyloxy group, p-methoxyphenylcarbonyloxy group and a pentafluorobenzoyloxy group.

Additionally, there are exemplified carbonate structures derived from carbonate half esters corresponding to a structure in which an oxygen atom is introduced, in the above acyloxy groups, into between their carbonyl groups and their alkyl or aryl groups.

Also, in the present invention, examples of the monovalent organic group represented by each of R₁ to R₅ (R₅ will be referred to hereinbelow) and Q₁ to Q₆ include a hydrogen atom, a halogen atom (e.g., a fluorine atom, a chlorine atom, a bromine atom or an iodine atom) and an alkyl group. The alkyl group is a linear, branched or cyclic, substituted or unsubstituted alkyl group. The alkyl group include alkyl groups (preferably, substituted or unsubstituted alkyl groups having one or more carbon atoms such as a methyl group, an ethyl group, a n-propyl group, an i-propyl group, a t-butyl group, a s-butyl group, a n-butyl group, an i-butyl group, a pentyl group, a hexyl group, a heptyl group, an octyl group, a nonyl group, a decyl group, an undecyl group, a dodecyl group, a tridecyl group, a tetradecyl group, a pentadecane group, a hexadecyl group, a heptadecyl group, an octadecyl group, a 3,7-dimethyloctyl group, a 2-ethylhexyl group, a trifluoromethyl group, a trifluorooctyl group, a trifluorododecyl group, a trifluorooctadecyl group and a 2-cyanoethyl group) and cycloalkyl groups (preferably, substituted or unsubstituted alkyl groups having three or more carbon atoms such as a cyclopentyl group, a cyclobutyl group, a cyclohexyl group and a pentafluorohexyl group). The alkyl groups referred to in the below-described substituents refer to the above-described alkyl groups.

Examples of the monovalent organic group represented by each of R₁ to R₅ and Q₁ to Q₆ further include an alkenyl group. The alkenyl group is a linear, branched or cyclic, substituted or unsubstituted alkenyl group. The alkenyl group include alkenyl groups (preferably, substituted or unsubstituted alkenyl groups having two or more carbon atoms such as groups obtained by changing one or more carbon-carbon single bonds to a double bond in the above-exemplified alkyl groups having two or more carbon atoms (e.g., an ethenyl group (a vinyl group), a propenyl group (an allyl group), a 1-butenyl group, a 2-butenyl group, a 2-methyl-2-butenyl group, a 1-pentenyl group, a 2-pentenyl group, a 3-pentenyl group, a 1-hexenyl group, a 2-hexenyl group, a 3-hexenyl group, a 1-heptenyl group, a 2-heptenyl group, a 3-heptenyl group, a 4-heptenyl group, a 1-octenyl group, a 2-octenyl group, a 3-octenyl group, a 4-octenyl group and a 1,1,1-trifluoro-2-butenyl group)) and cycloalkenyl groups such as groups obtained by changing one or more carbon-carbon single bonds to a double bond in the above-exemplified cycloalkyl groups having two or more carbon atoms (e.g., a 1-cycloallyl group, a 1-cyclobutenyl group, a 1-cyclopentenyl group, a 2-cyclopentenyl group, a 3-cyclopentenyl group, a 1-cyclohexenyl group, a 2-cyclohexenyl group, a 3-cyclohexenyl group, a 1-cycloheptenyl group, a 2-cycloheptenyl group, a 3-cycloheptenyl group, a 4-cycloheptenyl group and a 3-fluoro-1-cyclohexenyl group)). When the alkenyl group has stereoisomers such as a trans (E) form and cis (Z) form, both the stereoisomers may be used, or a mixture containing them at any ratio may be used also.

Examples of the monovalent organic group represented by each of $R_1$ to $R_5$ and $Q_1$ to $Q_6$ further include an alkynyl group (preferably, substituted or unsubstituted alkynyl groups having two or more carbon atoms such as groups obtained by changing one or more carbon-carbon single bonds to a triple bond in the above-exemplified alkyl groups having two or more carbon atoms (e.g., an ethynyl group, a proparygyl group, a trimethylsilylethynyl group and a triisopropylsilylethynyl group)).

Examples of the monovalent organic group represented by each of $R_1$ to $R_5$ and $Q_1$ to $Q_6$ further include an aryl group (preferably, substituted or unsubstituted aryl groups having six or more carbon atoms (e.g., a phenyl group, an o-tolyl group, a m-tolyl group, a p-tolyl group, a p-chlorophenyl group, a p-fluorophenyl group, a p-trifluorophenyl group and a naphthyl group)).

Examples of the monovalent organic group represented by each of $R_1$ to $R_5$ and $Q_1$ to $Q_6$ further include a heteroaryl group (preferably, 5- or 6-membered substituted or unsubstituted, aromatic or non-aromatic heterocyclic groups (e.g., a 2-furyl group, a 2-thienyl group, a 3-thienyl group, a 2-thienothienyl group, a 2-benzothienyl group and a 2-pyrimidyl group)).

Examples of the monovalent organic group represented by each of $R_1$ to $R_5$ and $Q_1$ to $Q_6$ further include an alkoxyl group and a thioalkoxyl group (preferably, substituted or unsubstituted alkoxyl groups and thioalkoxyl groups such as groups obtained by introducing an oxygen atom or a sulfur atom into the above-exemplified alkyl, alkenyl and alkynyl groups.

Examples of the monovalent organic group represented by each of $R_1$ to $R_5$ and $Q_1$ to $Q_6$ further include an aryloxy group and a thioaryloxy group (preferably, substituted or unsubstituted aryloxy groups and thioaryloxy groups such as groups obtained by introducing an oxygen atom or a sulfur atom the above-exemplified aryl group.

Examples of the monovalent organic group represented by each of $R_1$ to $R_5$ and $Q_1$ to $Q_6$ further include a heteroaryloxy group and a heterothioaryloxy group (preferably, substituted or unsubstituted heteroaryloxy groups and heterothioaryloxy groups such as groups obtained by introducing an oxygen atom or a sulfur atom into the above-exemplified heteroaryl groups), a cyano group, a hydroxyl group, a nitro group, a carboxylic group, a thiol group, an amino group (preferably, an amino group, substituted or unsubstituted alkylamino groups, substituted or unsubstituted anilino groups such as an amino group, a methylamino group, a dimethylamino group, an anilino group, an N-methyl-anilino group and a diphenylamino group; an acylamino group (preferably, a formylamino group, a substituted or unsubstituted alkylcarbonylamino group and a substituted or unsubstituted arylcarbonylamino group (e.g., a formylamino group, an acetylamino group, a pivaloylamino group, a lauroylamino group, a benzoylamino group and a 3,4,5-tri-n-octyloxyphenylcarbonylamino group)) and an aminocarbonylamino group (preferably, a substituted or unsubstituted aminocarbonylamino group (e.g., a carbamoylamino group, an N,N-dimethylaminocarbonylamino group, an N,N-diethylaminocarbonylamino and a morpholinocarbonylamino group))).

As described above, the monovalent organic group represented by $Q_1$ or $Q_2$ may be the same group as represented by $R_1$ to $R_5$, but $Q_1$ or $Q_2$ preferably represents an aryl group or heteroaryl group which may have a substituent, more preferably the groups $Q_1$ and $Q_2$ are bonded to form a ring.

Examples of the ring formed by the groups $Q_1$ and $Q_2$ include the followings.

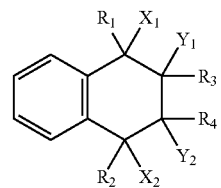

(1)

Example of ring structure of Q1, Q2

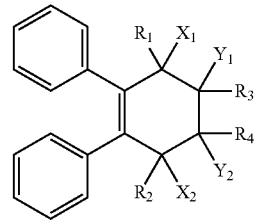

(2)

Example of ring structure of Q1, Q2

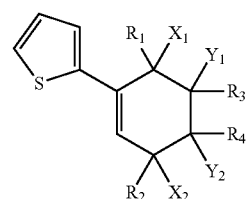

(3)

Example of ring structure of Q1, Q2

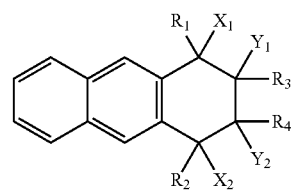

(4)

Example of ring structure of Q1, Q2

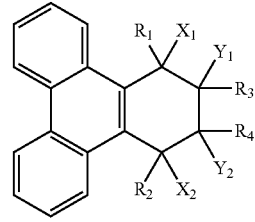

(5)

Example of ring structure of Q1, Q2

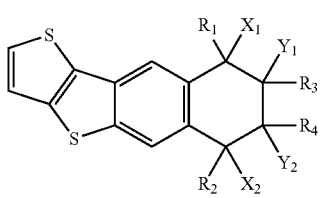

Example of ring
structure of Q1, Q2

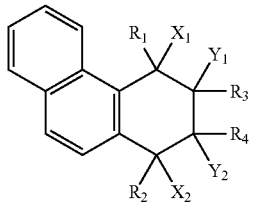

Example of ring
structure of Q1, Q2

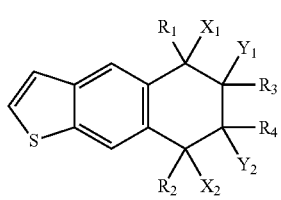

Example of ring
structure of Q1, Q2

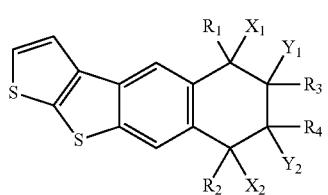

Example of ring
structure of Q1, Q2

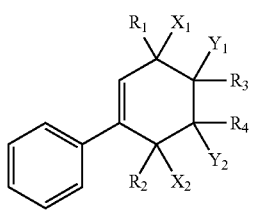

Example of ring
structure of Q1, Q2

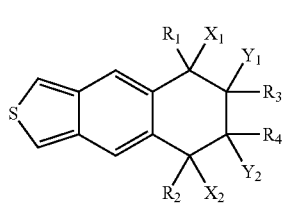

Example of ring
structure of Q1, Q2

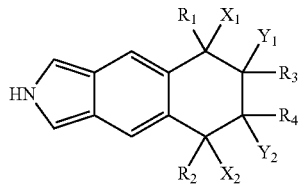

Example of ring
structure of Q1, Q2

The groups $Q_3$ to $Q_6$ may be the same groups as the groups $Q_1$ and $Q_2$. However, as shown in the following General Formulas (IV) and (V), preferably, one or more of $Q_3$ to $Q_6$ are the above-exemplified aryl group or heteroaryl group; or one or more pairs of $(Q_3, Q_4)$, $(Q_4, Q_5)$ and $(Q_5, Q_6)$ form a ring which is the above-exemplified aryl or heteroaryl group.

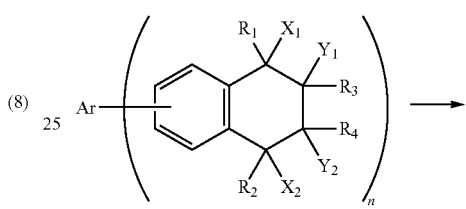

General Formula (IV)

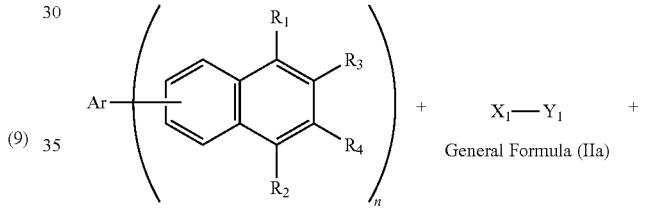

General Formula (IVa) + General Formula (IIa) + General Formula (IIb)

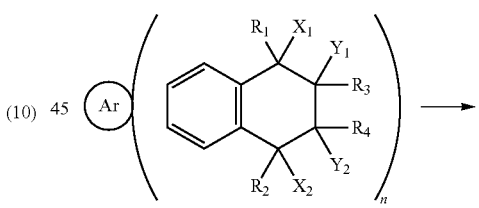

General Formula (V)

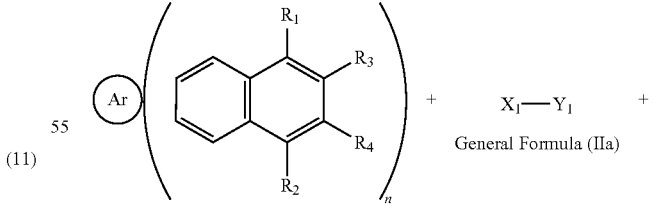

General Formula (Va) + General Formula (IIa) + General Formula (IIb)

In General Formulas (IV) and (V), Ar represents an aryl group or a heteroaryl group which may have a substituent. Preferred examples thereof include a benzene ring, a thiophene ring, a pyridine ring, a pyrazine ring, a pyrimidine ring, a triazine ring, a pyrrol ring, a pyrazole ring, an imidazole ring, a triazole ring, an oxazole ring, a thiazole ring, a furan ring, a selenophene ring and a silole ring. More preferably, Ar is at least one π-electron conjugated compound selected from the group consisting of (i) aromatic hydrocarbon rings, aromatic heterocyclic rings, compounds in which one or more aromatic hydrocarbon rings are ring-fused with one or more aromatic heterocyclic rings, compounds in which two or more aromatic hydrocarbon rings are ring-fused together, and compounds in which two or more aromatic heterocyclic rings are ring-fused together; and (ii) compounds in which one or more aromatic hydrocarbon rings are linked via covalent bond with one or more aromatic heterocyclic rings, compounds in which two or more aromatic hydrocarbon rings are linked together via a covalent bond, and compounds in which two or more aromatic heterocyclic rings are linked together via a covalent bond. Further, π electrons contained in the aromatic hydrocarbon rings or aromatic heterocyclic rings are preferably delocalized throughout the ring-fused or linked structure by the interaction as a result of ring-fused linkage or covalently bonding.

Here, the "covalent bond" may be, for example, a carbon-carbon single bond, a carbon-carbon double bond, a carbon-carbon triple bond, an oxyether bond, a thioether bond, an amide bond and an ester bond, with a carbon-carbon single bond, a carbon-carbon double bond and a carbon-carbon triple bond being preferred.

The number of the aromatic hydrocarbon rings or aromatic heterocyclic rings which are ring-fused or linked together via a covalent bond is preferably two or more. Specific examples thereof include naphthalene, anthracene, tetracene, chrycene and pyrene (the following General Formula Ar3), pentacene and thienothiophene, (the following General Formula thienodithiophene triphenylene, hexabenzocoronene and benzothiophene (the following General Formula Ar2), benzodithiophene and [1]benzothieno[3,2-b][1]benzothiophene (BTBT) (the following General Formula Ar4), dinaphto[2,3-b:2',3'-f][3,2-b]thienothiophene (DNTT) and benzodithienothiophene (TTPTT) (the following General Formula Ar5), fused polycyclic compounds such as naphthodithienothiophene (TTNTT) (the following General Formulas Ar6 and Ar7), and oligomers of aromatic hydrocarbon rings and aromatic heterocyclic rings such as biphenyl, terphenyl, quaterphenyl, bithiophene, terthiophene and quaterthiophene; phthalocyanines; and porphyrins.

Ar1

Ar2

Ar3

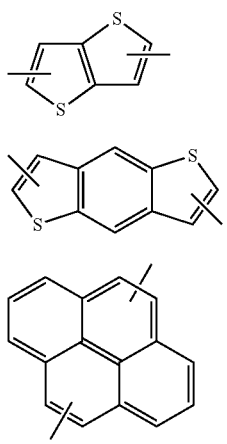

Ar4

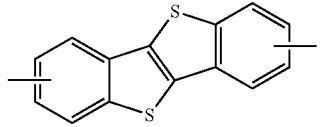

Ar5

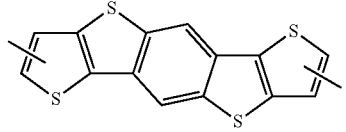

Ar6

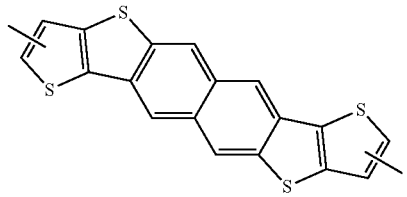

Ar7

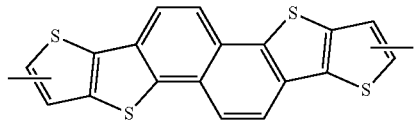

Also, in the above General Formulas, n is an integer of 1 or more and is the number of the solvent-soluble substituents linked to the group Ar. In General Formula (IV), n is the number of the solvent-soluble substituents linked via a covalent bond with the group Ar. Also, in General Formula (V), n is the number of the solvent-soluble substituents ring-fused with the group Ar.

Needless to say, n depends on the number of atoms able to be substituted or ring-fused in the group Ar. For example, an unsubstituted benzene ring has up to 6 positions at which it can be linked via a covalent bond with the solvent-soluble substituent(s), and has up to 6 sites at which it can ring-fused with the solvent-soluble substituent(s). However, the lower limit of n is preferably 2 considering the size of the compound (group) Ar itself, solubility, molecular symmetry and easy synthesis. When n is too large, the solvent-soluble substituents cause stearic hindrance between themselves, which is not preferred. In addition, a change in volume before or after elimination reaction may be large. Therefore, the upper limit of n is preferably 4 considering molecular symmetry, easy synthesis and appropriate solubility.

The acyloxy groups ($X_1$, $X_2$) or ($Y_1$, $Y_2$) preferably have a structure represented by the following General Formula (VI).

General Formula (VI)

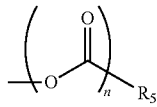

When n is 1, General Formula (VI) is the following General Formula (VI-1). And, the acyloxy groups ($X_1$, $X_2$) or ($Y_1$, $Y_2$) do not form a ring and are present independently.

General Formula (VI-1)

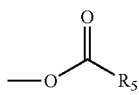

When n is 2, General Formula (VI) is the following General Formula (VI-2). And, the acyloxy groups ($X_1$, $X_2$) or ($Y_1$, $Y_2$) form a ring.

General Formula (VI-2)

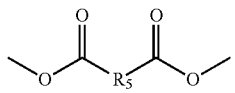

The group represented by $R_5$ is described above. In particular, $R_5$ preferably represents a hydrogen atom (excluding the case where n is 2 in General Formula (V)), a substituted or unsubstituted alkyl group, a substituted or unsubstituted alkenyl group, a substituted or unsubstituted alkynyl group, a substituted or unsubstituted alkoxyl group, a substituted or unsubstituted thioalkyl group, a substituted or unsubstituted aryl group, a substituted or unsubstituted heteroaryl group, a cyano group, with a hydrogen atom (excluding the case where n is 2 in General Formula (V)), a substituted or unsubstituted alkyl group, a substituted or unsubstituted alkoxyl group and a substituted or unsubstituted thioalkyl group being more preferred, with a substituted or unsubstituted alkyl group and a substituted or unsubstituted alkoxyl group being most preferred.

In addition to halogen atoms, eliminated components $X_1$-$Y_1$ and $X_2$-$Y_2$ may be, for example, carboxylic acids obtained by substituting the oxygen-containing bond of the above-exemplified acyloxy groups with a hydrogen atom and carbonate half esters thereof (e.g., formic acid, acetic acid, pyruvic acid, propionic acid, butylic acid, valeric acid, isovaleric acid, pivalic acid, caproic acid, lauric acid, stearic acid, monochloroacetic acid, monofluoroacetic acid, difluoroacetic acid, 2,2-difluoropropionic acid, trifluoroacetic acid, 3,3,3-trifluoropropionic acid, pentafluoropropionic acid, cyclopropanoic acid, cyclobutanoic acid, cyclohexanoic acid, benzoic acid, p-methoxybenzoic acid, pentafluorobenzoic acid, methyl hydrogencarbonate, ethyl hydrogencarbonate, isopropyl hydrogencarbonate and hexyl hydrogencarbonate). These carbonate half esters are generally unstable, and thus, may be decomposed into corresponding alcohols (e.g., mehtanol, ethanol, 2-propanol and hexanol) and carbon dioxide.

The group (substituent) represented by $R_5$ in General Formula (V) is not particularly limited. From the viewpoints of solvent solubility and film formability, it is advantageous that the substituent selected reduces intermolecular interaction to a certain extent and enhances affinity to a solvent. Meanwhile, when the volume before or after elimination of the substituents is considerably changed, there is a concern on problematic unevenness in coating of a thin film through elimination reaction. Therefore, the substituent used is preferably smaller in size to the greatest extent possible while maintaining appropriately solubility. Further, $R_5$ preferably represents an electron-attracting substituent (e.g., a halogen-containing alkyl group and a cyano group-containing group) with which the carbonyl oxygen is negatively charged to a larger extent, since elimination reaction can be efficiently performed (although the reason for this is still unclear).

As described above, the leaving substituent-containing compound of the present invention contains leaving solvent-soluble substituents which impart solvent solubility to the leaving substituent-containing compound.

In the present invention, the term "solvent solubility" means that a compound shows a solubility of 0.05% by mass or more, preferably 0.1% by mass or more, more preferably 0.5% by mass or more, most preferably 1.0% by mass, when a solvent to which the compound is added is heated under reflux and then cooled down to room temperature.

Also, the solvent solubility of the π-electron conjugated compound represented by A-(C)n varies with a combination of substituents A and B.

Here, the term "solvent insolubilization" means that the solvent solubility of a compound is reduced by one digit figure or more. Specifically, when a solvent to which the compound is added is heated under reflux and then cooled down to room temperature, it is preferable to reduce the solvent solubility from 0.05% by mass or more to 0.005% by mass or less; more preferably from 0.1% by mass or more to 0.01% by mass or less; particularly preferably from 0.5% by mass or more to less than 0.05% by mass; most preferably from 1.0% by mass or more to less than 0.1% by mass. And, the term "solvent insolubility" means that a compound shows a solubility of less than 0.01% by mass, preferably 0.005% by mass or less, more preferably 0.001% by mass or less, when a solvent to which the compound is added is heated under reflux and then cooled down to room temperature.

The type of the solvent used for measuring the "solvent solubility" and "solvent insolubility" is not particularly limited. An actually used solvent may be used at an actually set temperature for the measurement of the solvent solubility. In addition, THF, toluene, chloroform, methanol, other solvents may be used at 25° C. for the measurement of the solvent solubility.

Note that a solvent usable in the present invention should not be construed as being limited to these solvents.

The solubility greatly changes before or after conversion through elimination reaction. As a result, even when another film is immediately formed on the underlying film made of the compound exhibiting such solubility, the underlying film does not tend to be abraded by the solvent used for the formation of the another film. Thus, the compound of the present invention is useful in production processes for organic electronic devices such as organic thin-film transistors, organic EL elements and organic solar cells.

The following compounds will be given as specific examples of the leaving substituent-containing compound of the present invention. The leaving substituent-containing compound of the present invention should not be construed as being limited thereto. Also, it is easily supposed that there are several stereoisomers of the leaving substituent-containing compound depending on the steric configuration of the acyloxy groups, and that the following compounds are mixtures of such stereoisomers.

Exemplary compound 1
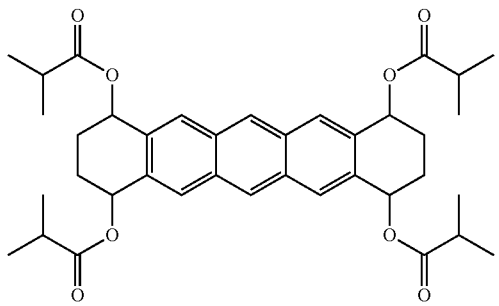
Exemplary compound 2
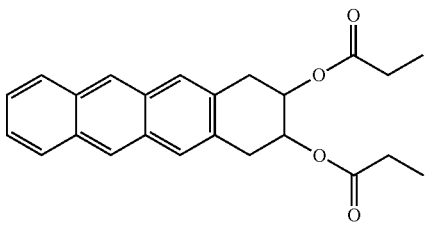
Exemplary compound 3
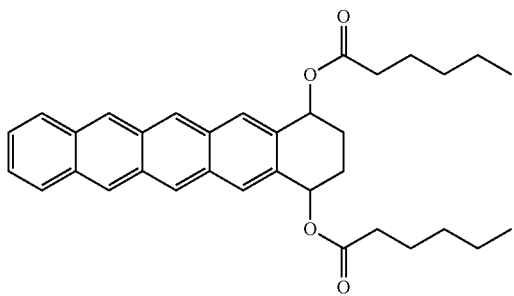
Exemplary compound 4
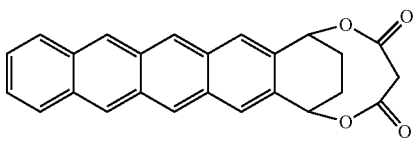
Exemplary compound 5
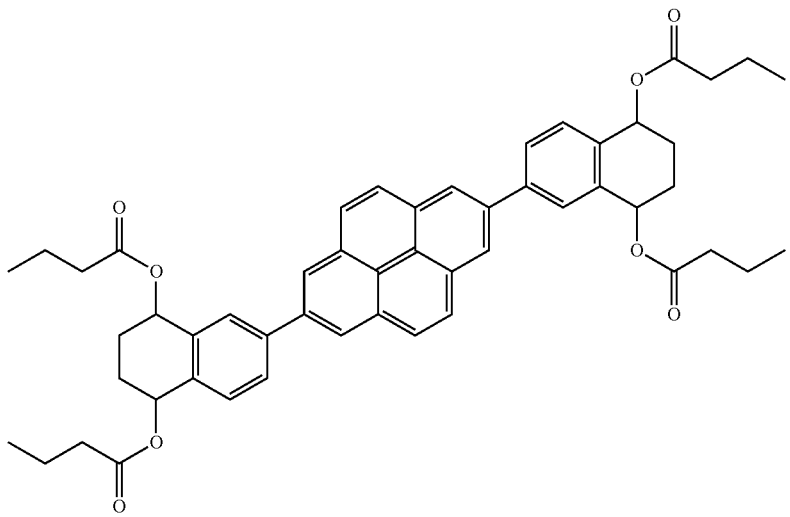
Exemplary compound 6
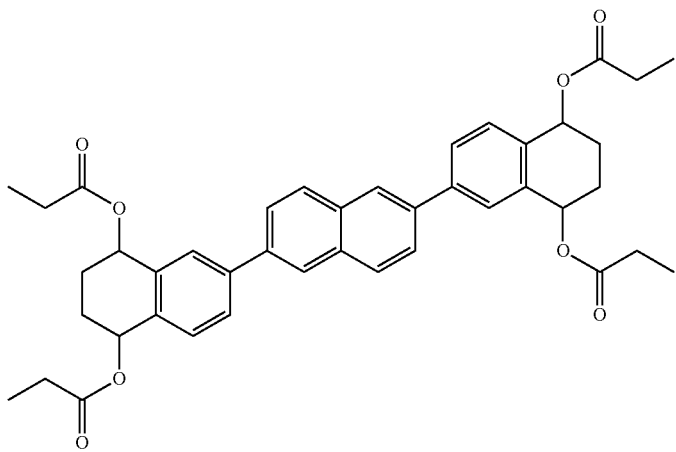

-continued
Exemplary compound 7
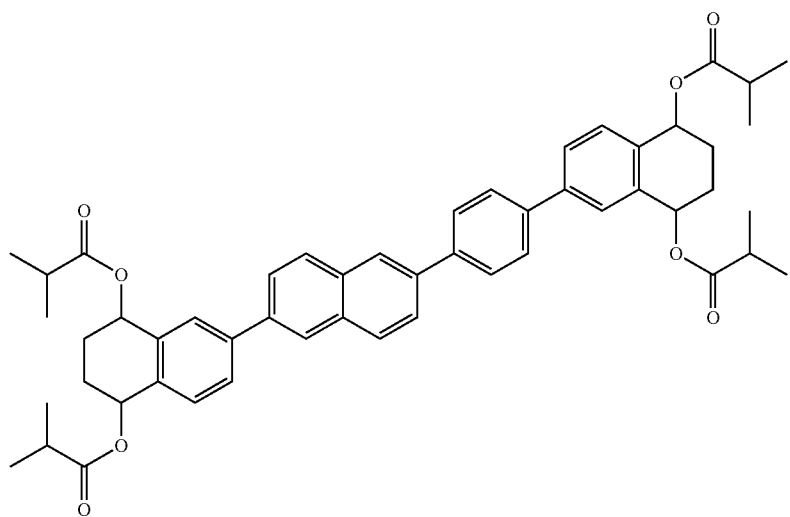
Exemplary compound 8
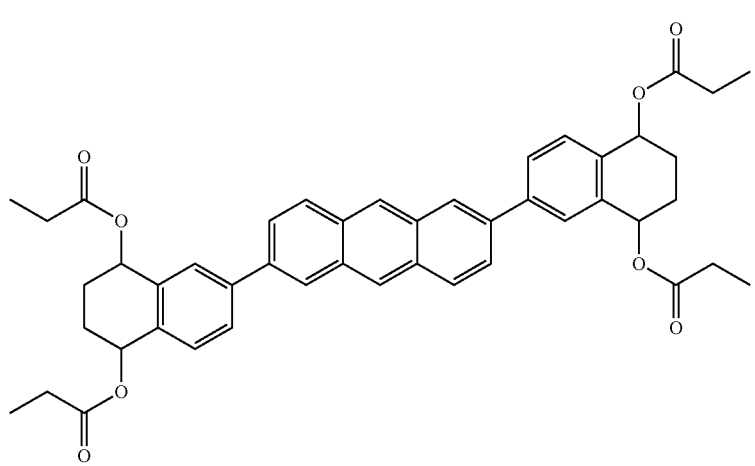
Exemplary compound 9
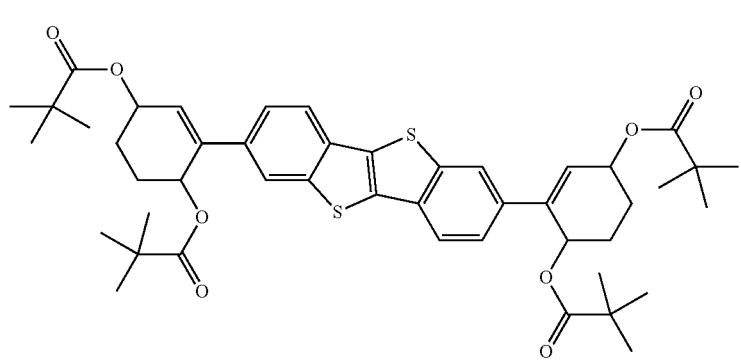
Exemplary compound 10
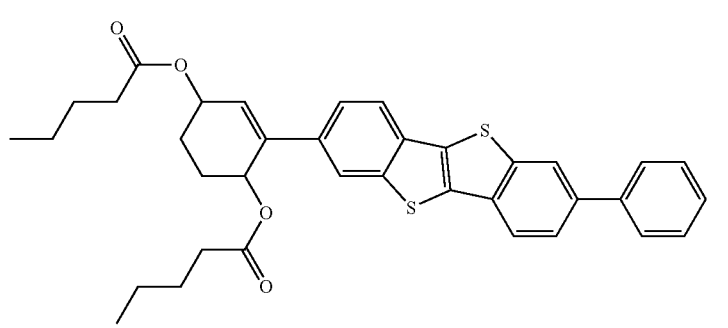

-continued
Exemplary compound 11
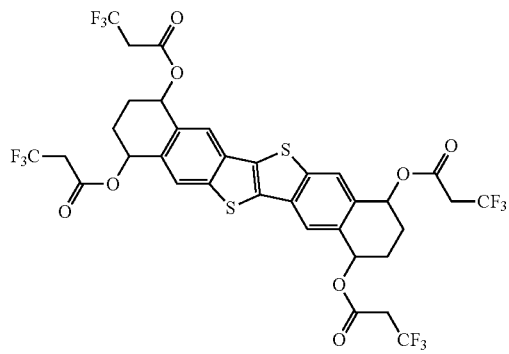
Exemplary compound 12
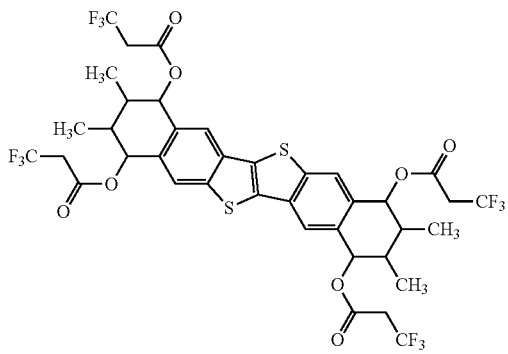
Exemplary compound 13
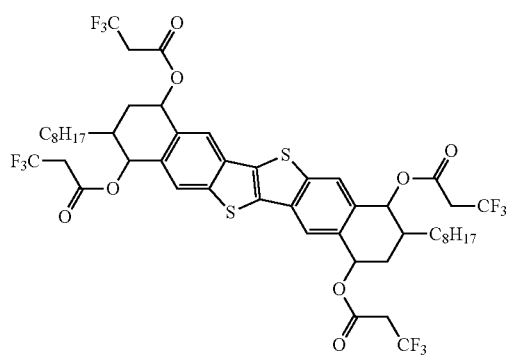
Exemplary compound 14
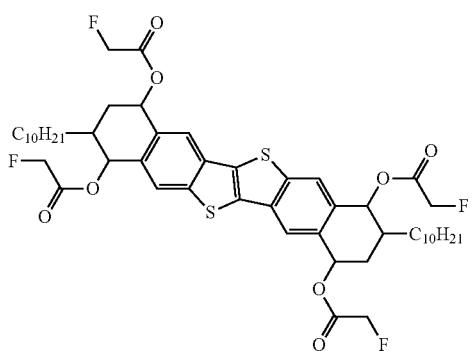
Exemplary compound 15
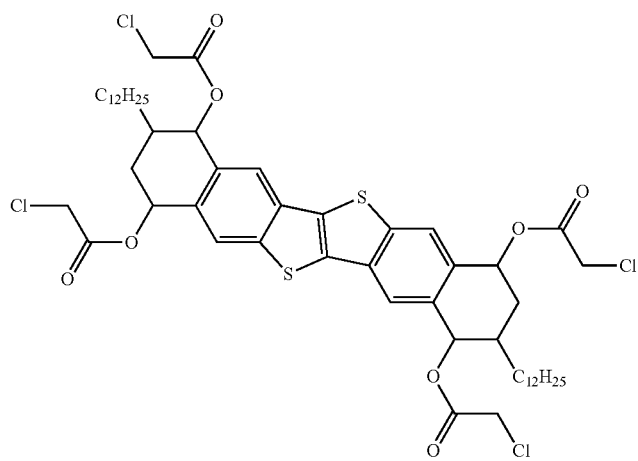
Exemplary compound 16
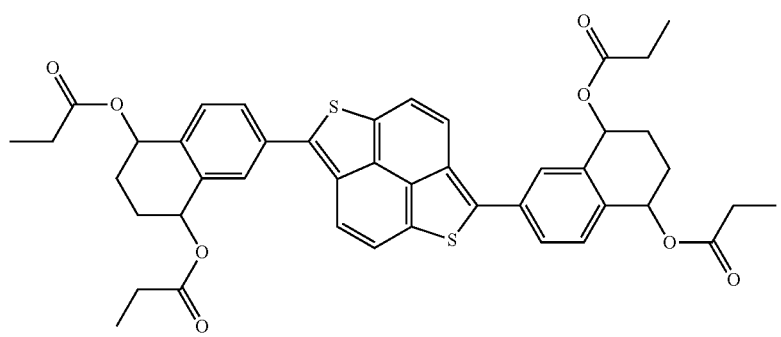

-continued
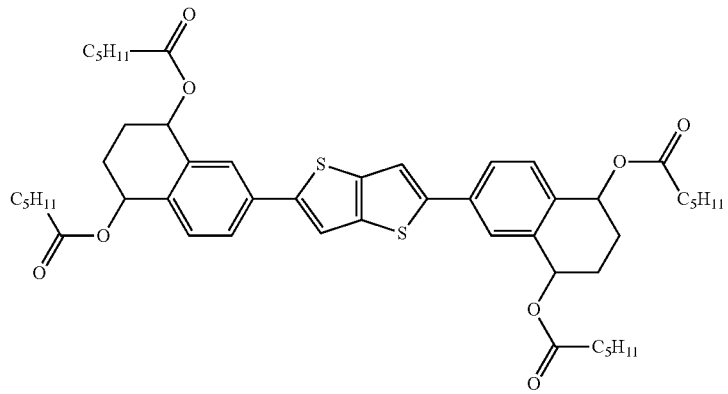
Exemplary compound 17
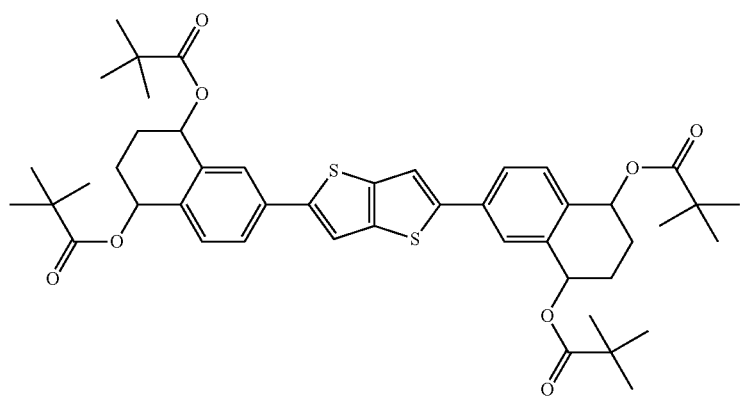
Exemplary compound 18
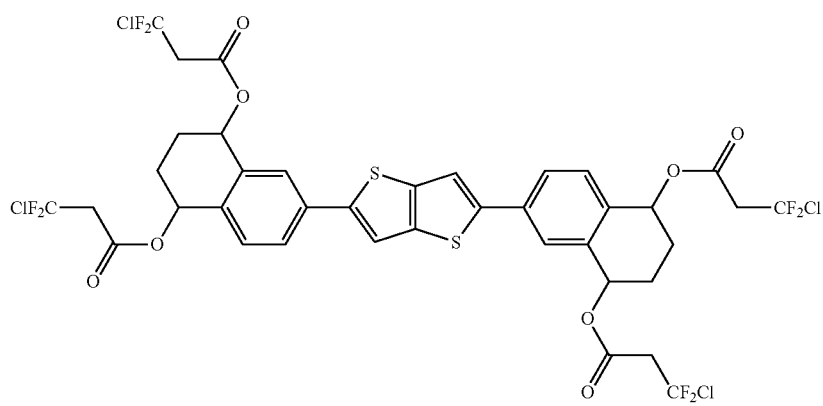
Exemplary compound 19
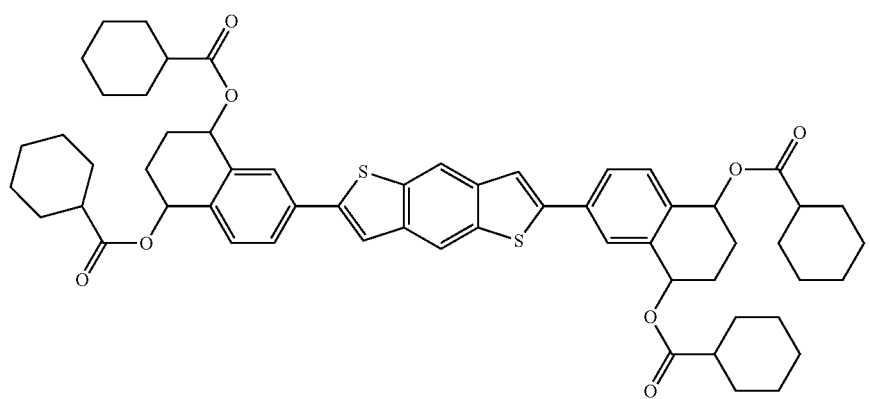
Exemplary compound 20

-continued
Exemplary compound 21
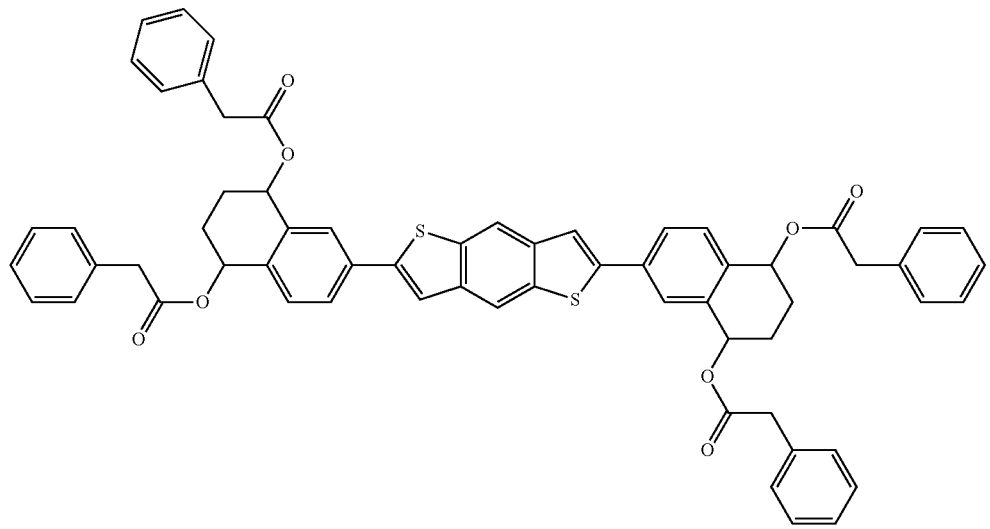
Exemplary compound 22
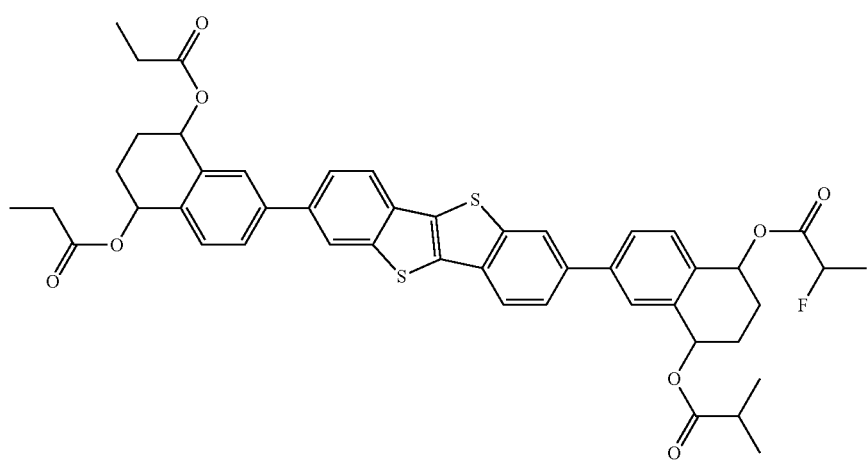
Exemplary compound 23
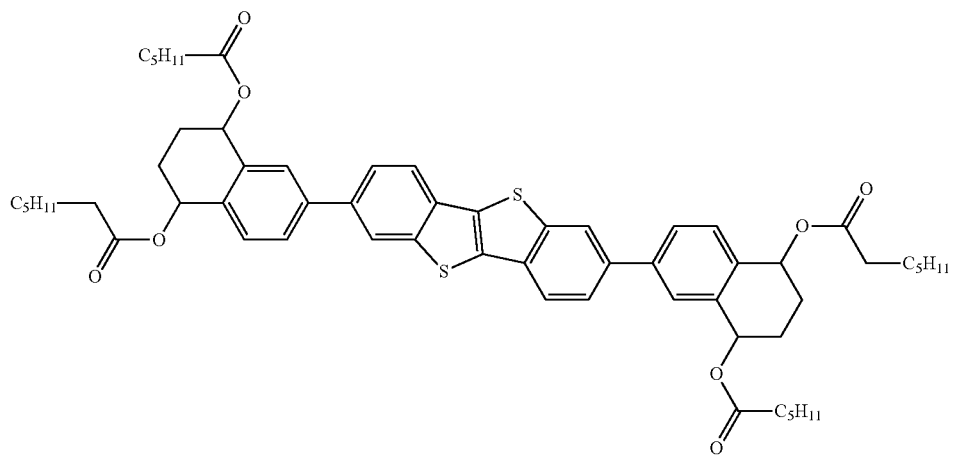

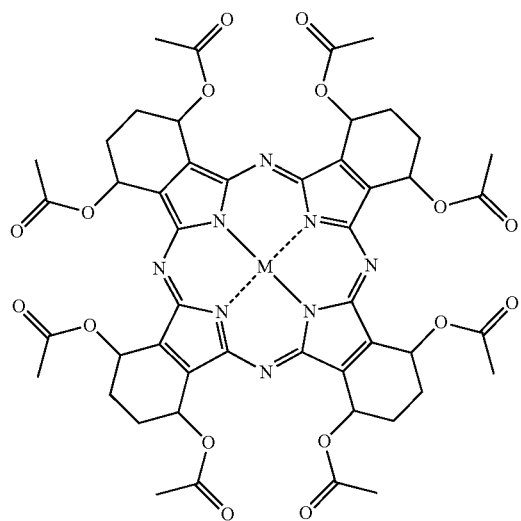
M = H₂: Exemplary compound 24
M = Cu: Exemplary compound 25
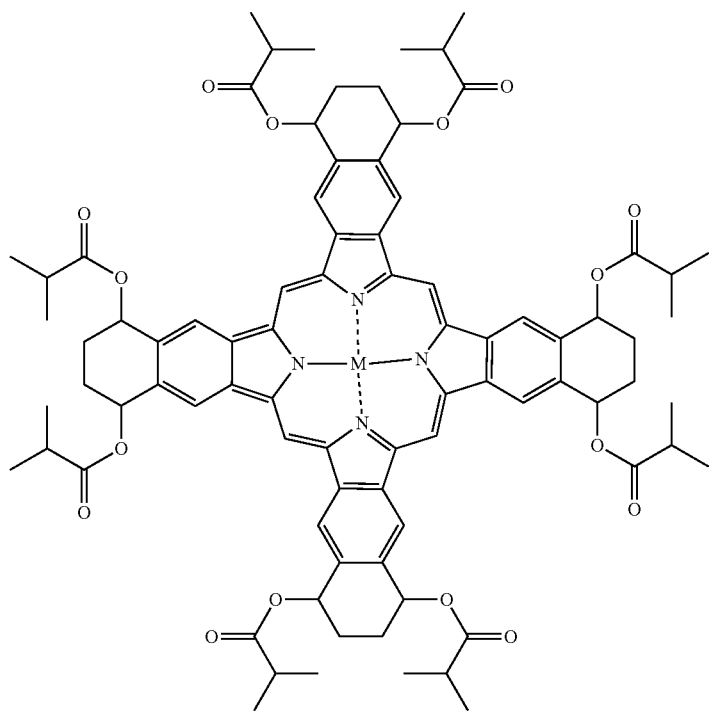
M = H₂: Exemplary compound 26
M = Cu: Exemplary compound 27

-continued
Exemplary compound 28
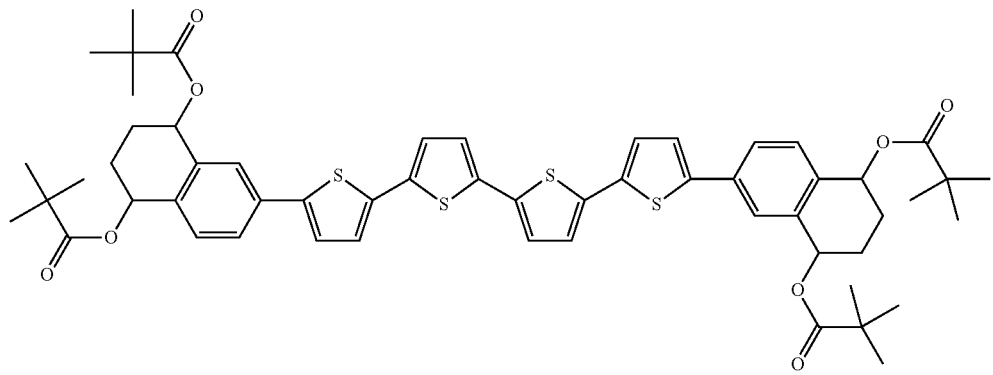
Exemplary compound 29
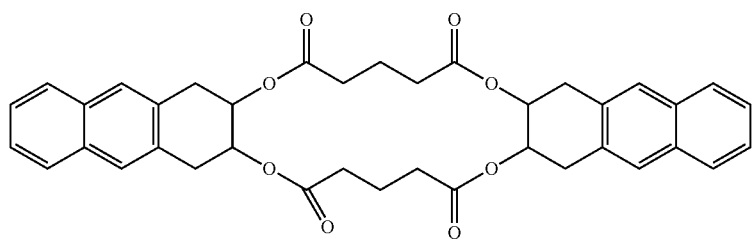
Exemplary compound 30
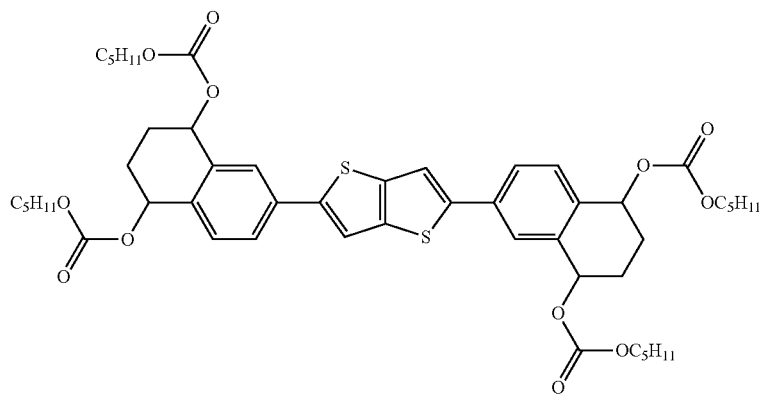
Exemplary compound 31
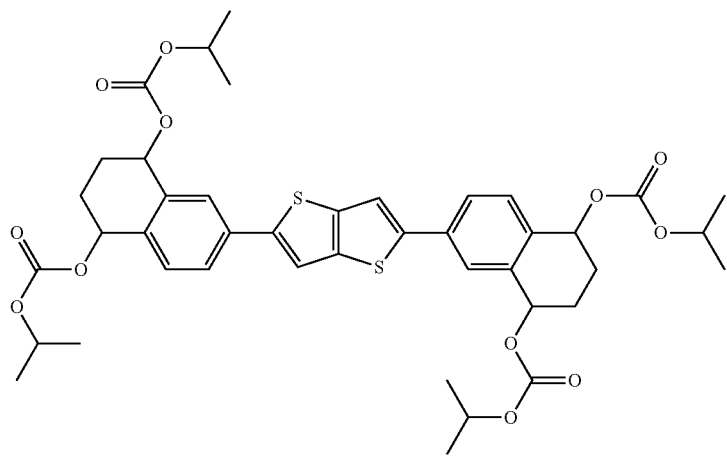

Exemplary compound 32
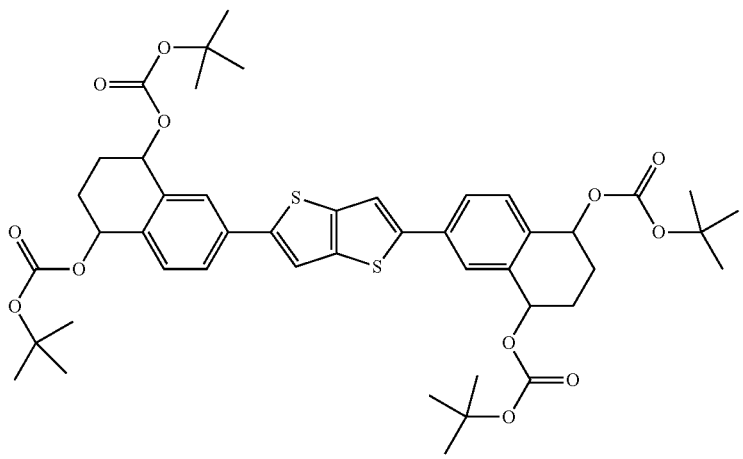
Exemplary compound 33
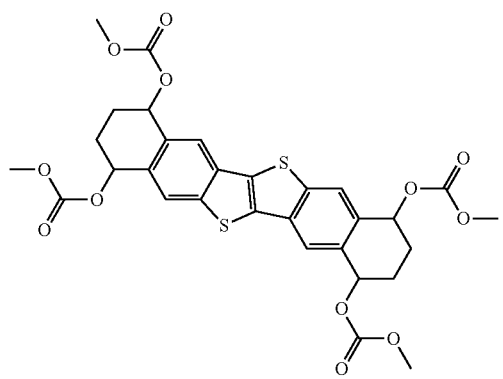
Exemplary compound 34
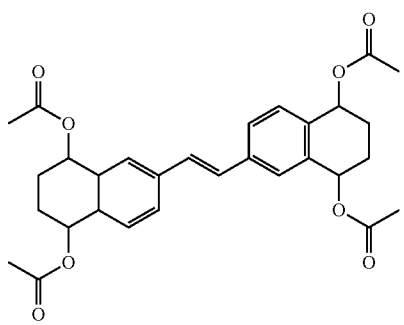
Exemplary compound 35
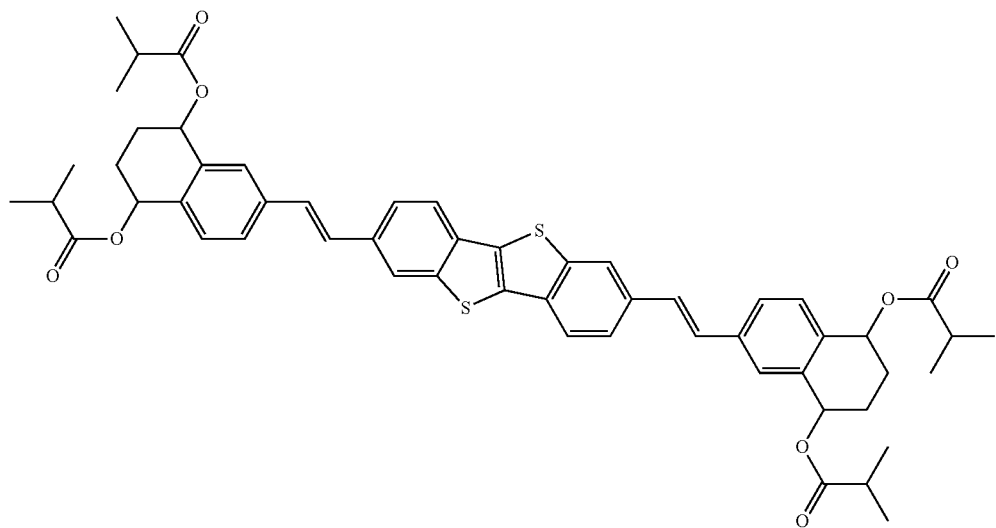

-continued
Exemplary compound 36
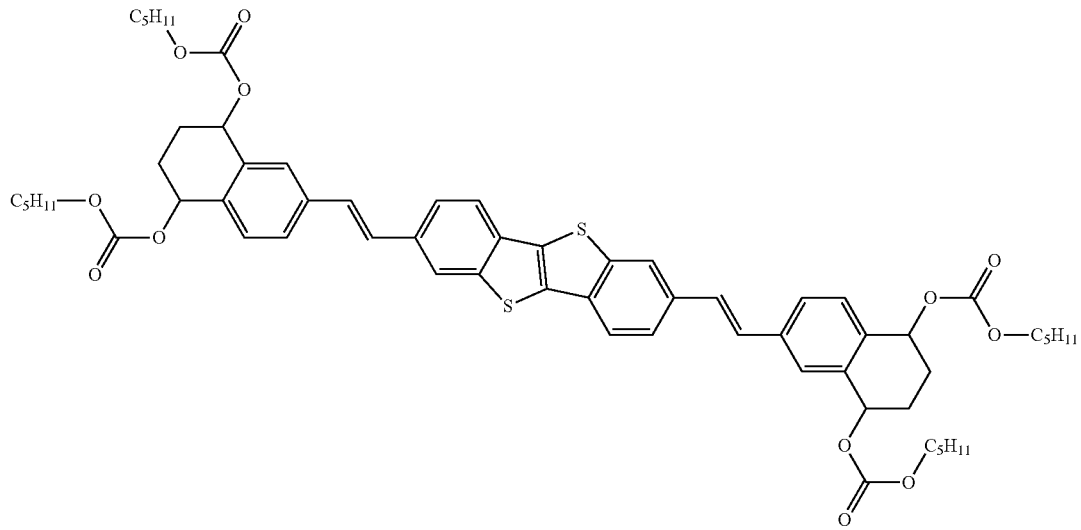
Exemplary compound 37
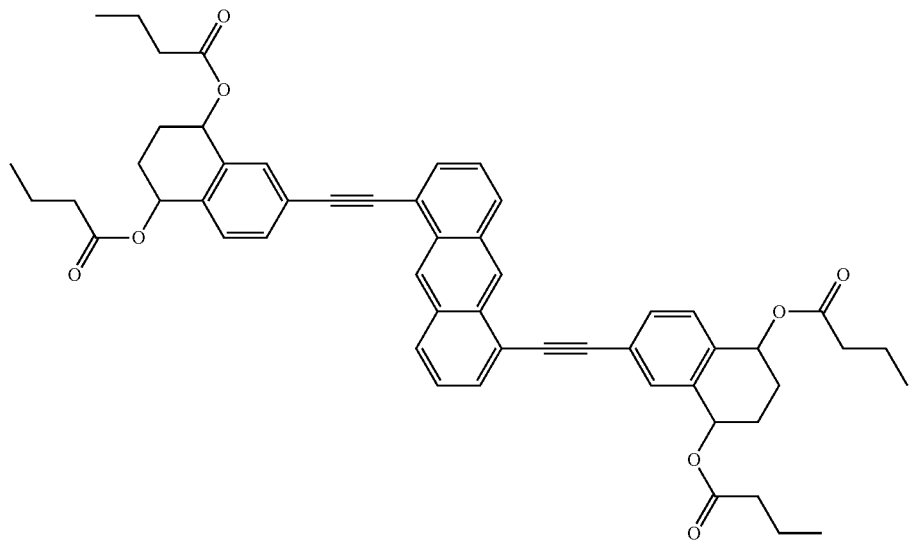
Exemplary compound 38
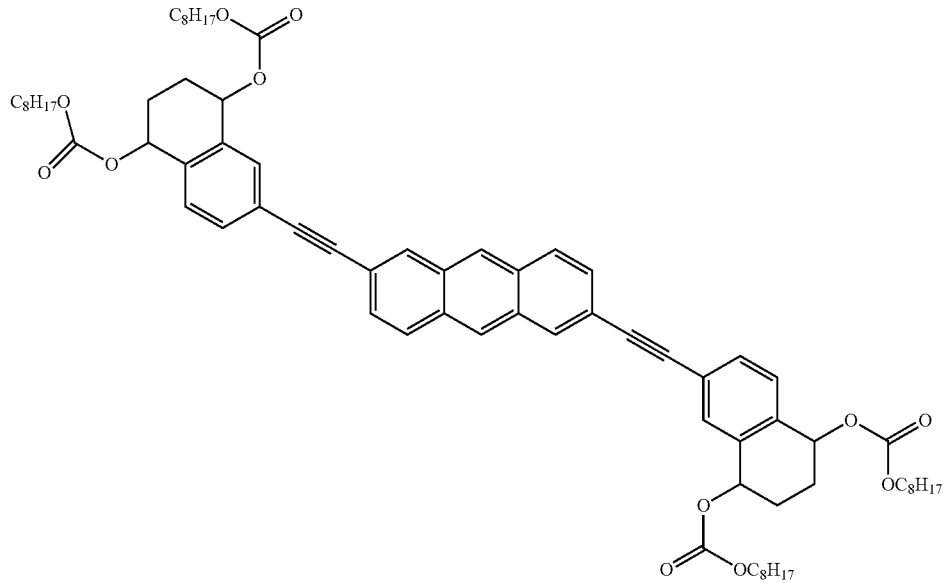

Exemplary compound 39

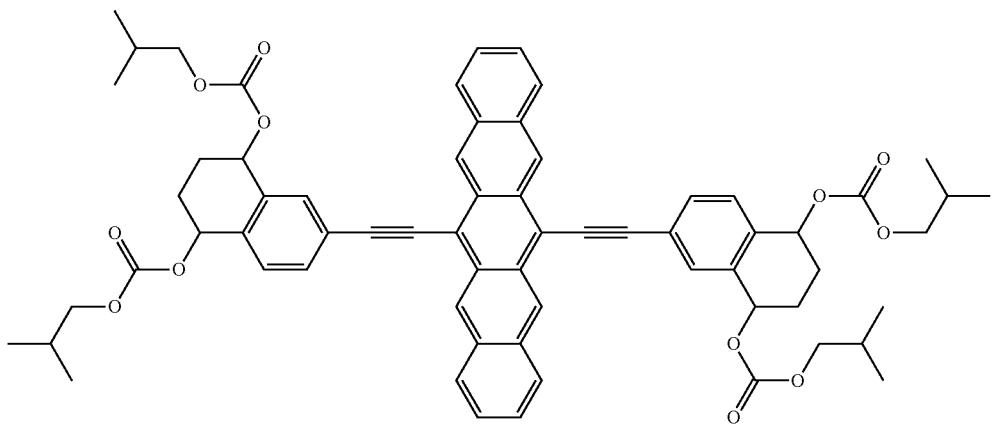

By applying energy (e.g., heat) to the leaving substituent-containing compound so that the specific substituents are eliminated through the below-described elimination reaction, a specific compound can be obtained.

Next will be given specific examples of the specific compound produced from the above-exemplified leaving substituent-containing compounds. The specific compound of the present invention should not be construed as being limited thereto.

Specific compound 1

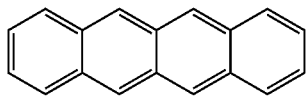

Specific compound 2

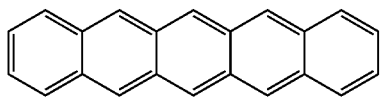

Specific compound 3

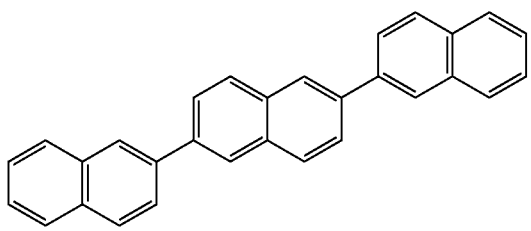

Specific compound 4

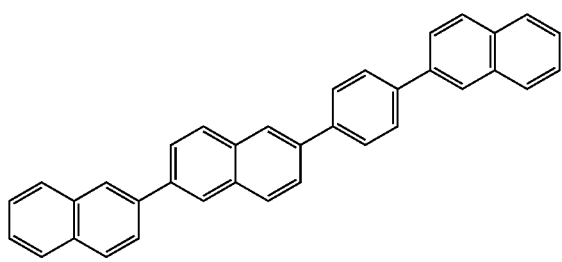

Specific compound 5

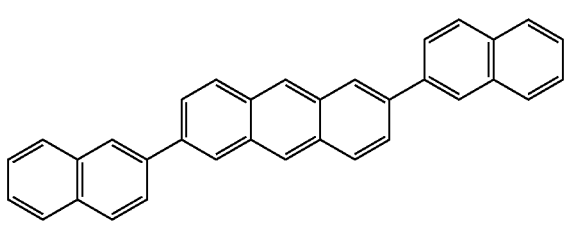

Specific compound 6

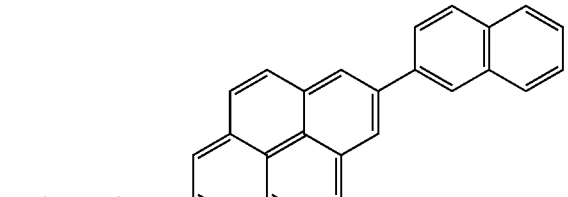

Specific compound 7

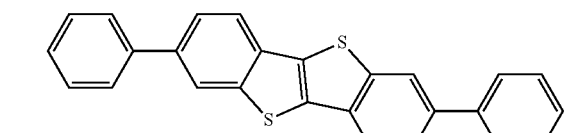

Specific compound 8

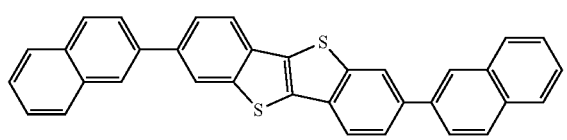

Specific compound 9
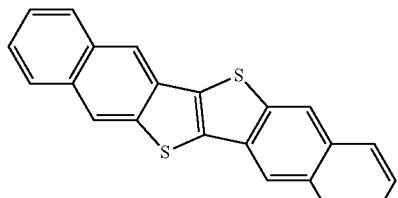
Specific compound 10
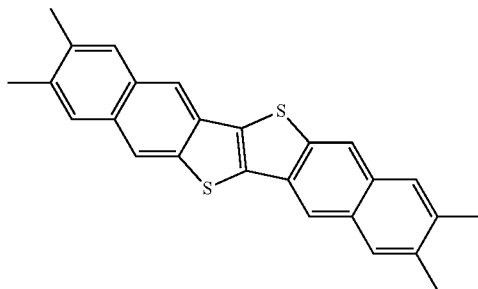
Specific compound 11
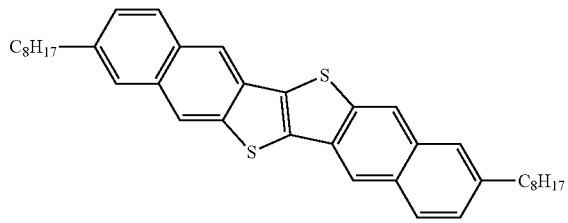
Specific compound 12
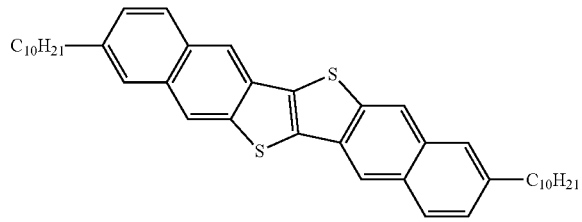
Specific compound 13
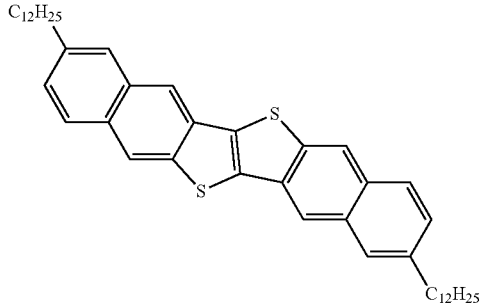
Specific compound 14
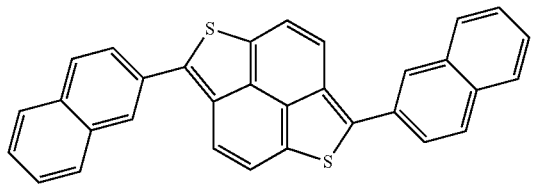
Specific compound 15
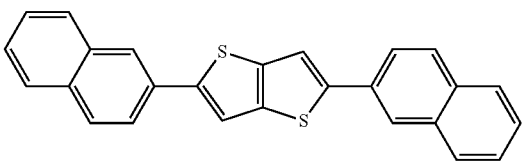
Specific compound 16
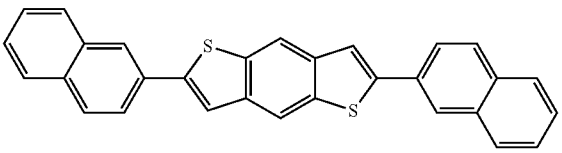
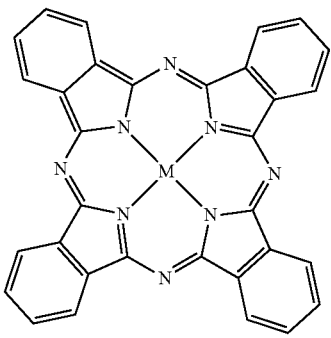
M = $H_2$: Specific compound 17
M = Cu: Specific compound 18
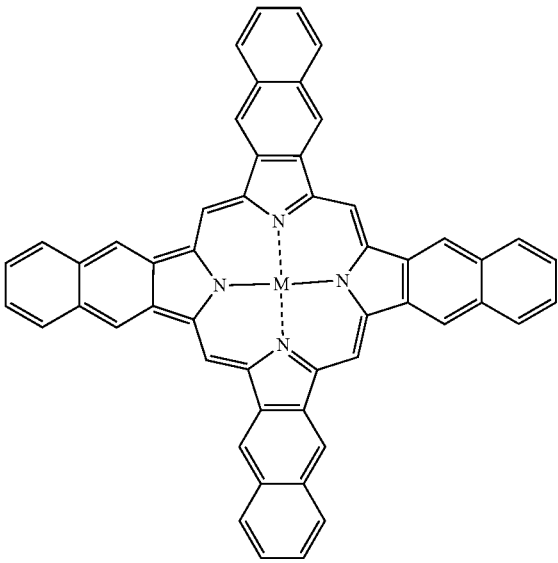
M = $H_2$: Specific compound 19
M = Cu: Specific compound 20
Specific compound 21
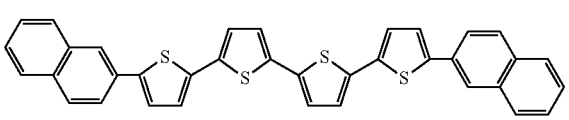

Specific compound 22

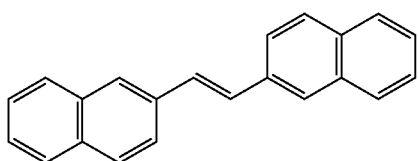

Specific compound 23

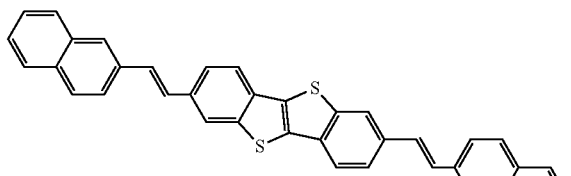

Specific compound 24

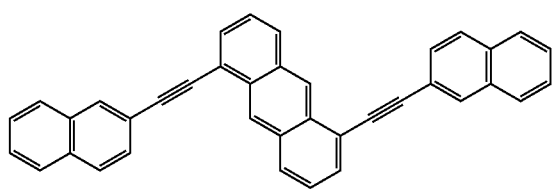

Specific compound 25

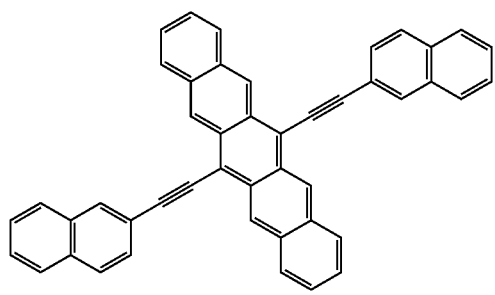

(Production Method of Specific Compound by Elimination Reaction of Leaving Substituent-Containing Compound)

Elimination reaction will be specifically described.

From a compound having a cyclohexene ring structure represented by General Formula (I), eliminating components represented by General Formulas (IIa) and (IIb) are eliminated, so that the compound having a cyclohexene ring structure is converted into a specific compound represented by General Formula (Ia).

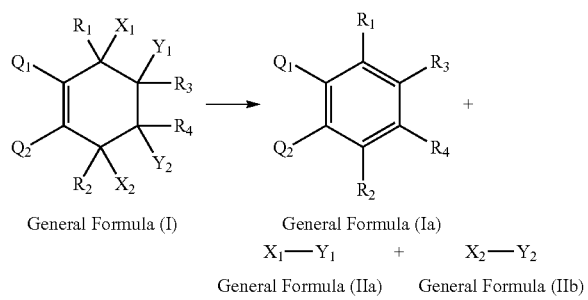

General Formula (I)    General Formula (Ia)

$X_1$—$Y_1$    +    $X_2$—$Y_2$

General Formula (IIa)    General Formula (IIb)

There are several isomers represented by General Formula (I) depending on the steric configuration of the substituents. However, these isomers are all converted into the specific compound represented by General Formula (Ia), and have the same eliminated components as in the compound represented by General Formula (I). It is preferred that $X_1$ and $Y_1$ or $X_2$ and $Y_2$ be located on the same side with respect to the cyclohexene ring plane, that is, form a so-called cis configuration, from the standpoints of efficiency of elimination reaction, conversion temperature, and reaction yield.

$(X_1, X_2)$ and $(Y_1, Y_2)$ which are groups eliminated from the compound represented by General Formula (I) are defined as leaving substituents, and $X_1$-$Y_1$ and $X_2$-$Y_2$ are defined as eliminated components. The eliminated components may be solid, liquid, or gas. In view of removal of the eliminated components to the outside of a system, the eliminated components are preferably liquid or gas, particularly preferably gas at normal temperature, or solid or liquid formed into gas at a temperature for performing elimination reaction.

A boiling point of the liquid eliminated component in an atmospheric pressure (1,013 hPa) is preferably 500° C. or lower. From the viewpoint of easiness of removal of the eliminated component to the outside of the system, and the temperature of decomposition and sublimation of a π-electron conjugated compound to be generated, the boiling point is more preferably 400° C. or lower, particularly preferably 300° C. or lower.

Hereinafter, one embodiment, in which $(X_1, X_2)$ represent the same acyloxy groups; $(Y_1, Y_2)$ and $R_1$ to $R_4$ represent hydrogen atoms; $R_6$ represents a substituted or unsubstituted alkyl group or a substituted or unsubstituted alkoxy group, will be described. However, the leaving substituent-containing compound of the present invention will not be limited thereto.

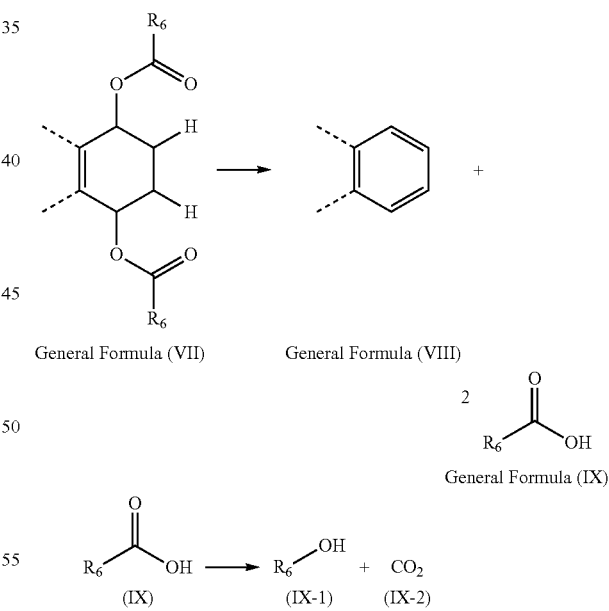

General Formula (VII)    General Formula (VIII)

General Formula (IX)

In the above reaction, from a cyclohexene ring structure represented by General Formula (VII), two carboxylic acids each having an alkyl chain represented by General Formula (IX) are eliminated as the eliminated components, to thereby be converted into a structure having a benzene ring represented by General Formula (VIII). In the case where $R_6$ is a substituted or unsubstituted alkoxy group, carbonate half ester (IX) is unstable, and may be decomposed to alcohol (IX-1) and carbon dioxide (IX-2) as shown above. An outline of a mechanism of the eliminating component eliminated from the compound represented by General Formula (VII) will be described below.

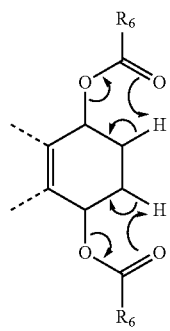

General Formula (VII)

As shown in General Formula (VII), a six-membered cyclic transition state is established, and 1,5-transposition of a hydrogen atom on β-carbon to an oxygen atom on carbonyl occurs, thereby causing concerted elimination reaction. A carboxylic acid is eliminated from the cyclohexene ring structure, and the cyclohexene ring structure is converted into a benzene ring structure represented by General Formula (VIII). In the case where several stereoisomers are present, the above described reaction proceeds even though the reaction rates varied depending on the stereoisomers.

However, it is preferred that an acyloxy group and a hydrogen atom are located on the same side with respect to the cyclohexene ring plane, namely, form cis configuration from the standpoints of efficiency of elimination reaction, conversion temperature, and reaction yield.

Since removal and transition of the hydrogen atom on the β-carbon are the first step of the reaction, the higher the degree of the negative polarization of an oxygen atom is, the easier the reaction occurs. Thus, the force of removing a hydrogen atom becomes larger, possibly thereby reducing necessary energy for causing elimination reaction. The degree of the negative polarization of an oxygen atom is changed, for example, according to the type of the alkyl chain in the side chain, or by replacing the oxygen atom with a chalcogen atom such as selenium, tellurium, and polonium which belong to the same group 16 as the oxygen atom does.

Examples of the energies applied for performing elimination reaction include heat, light and electromagnetic wave. Heat or light is preferred in terms of reactivity, yield or post treatment. Particularly preferred is heat. Alternatively, heat and light can be used in combination. When heat and light are used in combination, these may be used at the same time, or sequentially. Alternatively, in the presence of acid or base, the aforementioned energies may be applied.

Generally, elimination reaction depends on the structure of a functional group. However, most cases of elimination reaction need heating from the standpoints of reaction speed and reaction ratio.

Examples of heating methods for performing elimination reaction include, but not limited thereto, a method for heating on a support, a method for heating in an oven, a method for irradiation with microwave, a method for heating by converting light to heat using a laser beam, and a method using a photothermal conversion layer.

Heating temperature for performing elimination reaction may be a room temperature (approximately 25° C.) to 500° C. In consideration of thermal stability of the materials and a boiling point of the eliminated components as to the lower limit of the temperature, and in consideration of energy efficiency, percentage of the presence of unconverted molecule, and the decomposition of π-electron conjugated compound after conversion as to the upper limit of the temperature, the temperature is preferably 40° C. to 500° C. Moreover, in consideration of thermal stability of synthesis of the precursor, the decomposition and sublimation temperatures of π-electron conjugated compound after conversion, the temperature is more preferably 80° C. to 400° C., and particularly preferably 80° C. to 300° C.

Here, the sublimation temperature is defined as a temperature at which the mass reduction of 5%, preferably 3% or less, and more preferably 1.0% from initial mass in TG-DTA is observed.

As to the heating time, the higher the temperature is, the shorter the reaction time becomes. The lower the temperature is, the longer the time required for elimination reaction becomes.

Heating time depends on the reactivity and amount of the leaving substituent-containing compound, and is generally 0.5 min to 120 min, preferably 1 min to 60 min, and particularly preferably 1 min to 30 min.

In the case where light is used as the external stimulus, for example, infrared lamp or irradiation of light of wavelength absorbed by a compound (for example, exposure to light of wavelength 405 nm or less) may be used. On this occasion, a semiconductor laser may be used. Examples of semiconductor laser beam include a near-infrared region laser beam (generally, a laser beam of wavelength around 780 nm), a visible laser beam (generally, a laser beam of wavelength in the range of 630 nm to 680 nm), and a laser beam of wavelength of 390 nm to 440 nm. Particularly preferable laser beam is a laser beam having a wavelength region of 390 nm to 440 nm, and a semiconductor laser beam having a laser emission wavelength of 440 nm or less is preferably used. Among these semiconductor laser beam, examples of preferable light sources include a bluish-violet semiconductor laser beam having an emission wavelength region of 390 nm to 440 nm (more preferably from 390 nm to 415 nm), and a bluish-violet SHG laser beam having a center emission wavelength of 425 nm that has been converted to a half wavelength of the infrared semiconductor laser beam having a center emission wavelength of 850 nm by using an optical waveguide element.

The above described acid or base serves as a catalyst of elimination reaction, and conversion can be performed at lower temperature. A method of using the acid or base is not particularly limited. Examples of the method include a method in which the acid or base may be directly added to the leaving substituent-containing compound, a method in which the acid or base is dissolved in any solvent to form a solution, and the solution is added to the leaving substituent-containing compound, a method in which the vaporized acid or base is heated to add the leaving substituent-containing compound, and a method in which a photoacid generator and a photobase generator are used, and followed by light irradiation, to thereby obtain an acid and base in the reaction system.

Examples of the acids include, but not limited thereto, hydrochloric acid, nitric acid, sulfuric acid, acetic acid, trifluoroacetic acid, trifluoromethanesulfonic acid, 3,3,3-trifluoropropionic acid, formic acid, phosphoric acid and 2-butyl octanoic acid. Particularly preferred are volatile acids having high acidity, such as hydrochloric acid, nitric acid, trifluoroacetic acid, and trifluoromethanesulfonic acid.

Examples of the photoacid generators include ionic photoacid generators such as sulfonium salt, and an iodonium salt; and nonionic photoacid generators such as imide sulfonate, oxime sulfonate, disulfonyl diazomethane, and nitrobenzyl sulfonate.

Examples of the bases include, but not limited thereto, hydroxides such as sodium hydrate, potassium hydrate, carbonates such as sodium hydrogen carbonate, sodium carbonate, potassium carbonate, amines such as triethylamine and pyridine, and amidines such as diazabicycloundecene, diazabicyclononene.

Examples of photobase generators include carbamates, acyloximes, and ammonium salts.

Elimination reaction is preferably performed in a volatile acid or base atmosphere from the standpoint of easiness of removal of the acid or base to the outside of the system after reaction.

Elimination reaction can be performed in an ambient atmosphere regardless of the absence or presence of the catalyst. Elimination reaction is preferably performed in an inert gas atmosphere or reduced pressure in order to reduce any influence of side reaction such as oxidation or influence of moisture, and to promote removal of an eliminated component to outside the system. In addition to the aforementioned carboxylate, examples of the leaving substituents include, but not limited thereto, a halogen atom, esters such as carbonate, xanthate ester, sulfonate, phosphate, amine oxide, sulfoxide, and selenoxide having β-hydrogen.

In addition to the method of obtaining carboxylate by reacting the alcohol described below with carboxylic acid chloride or carboxylic acid anhydride, or through exchange reaction between a halogen atom and silver carboxylate or carboxylic acid-quaternary ammonium salt, examples of methods for forming the leaving substituents include, but not limited thereto, a method in which phosgene is reacted with alcohol so as to obtain carbonate, a method in which alcohol is reacted with carbonate half esters such as alkyl chloroformate, etc. so as to obtain carbonate, a method in which carbon disulfide is added in alcohol, and alkyl iodide is reacted therewith to obtain xanthate ester, a method in which tertiary amine is reacted with hydrogen peroxide or carboxylic acid so as to obtain amine oxide, and a method in which ortho selenocyano nitrobenzene is reacted with alcohol so as to obtain selenoxide.

(Method for Producing Leaving Substituent-Containing Compound)

The leaving substituent-containing compound of the present invention is characterized by having a cyclohexene skeleton and an acyloxy group (this structural portion is called as a soluble substituent). Since the soluble substituent is sterically bulky but not stiff, the crystallinity is poor. Thus, a molecule having such structure excels in solubility, and has properties of easily obtaining a film having low crystallinity (amorphous), when a solution containing this structure is applied.

Next, a method for forming a halogen atom and an acyloxy group in the cyclohexene skeleton of the soluble substituent will be specifically described.

The leaving substituent-containing compound can be derived from a compound having the cyclohexene skeleton represented by General Formula (X), which can be produced by the conventional method and used as a raw material. From the viewpoint of elimination reaction mode of the present invention, it is preferred that at least one hydrogen atom be located at positions 1 and 4 and/or positions 2 and 3.

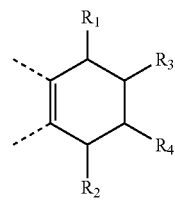

General Formula (X)

in General Formula (X), $R_1$ to $R_4$ are the same as described above.

Next, as shown in General Formula ($X_1$), by using a brominating agent, positions 1 and 4 and/or positions 2 and 3 are selectively halogenated. From the viewpoint of reactivity in the post step, an atom to be halogenated is preferably an iodine atom, a bromine atom, and a chlorine atom, and particularly preferably a bromine atom. Examples of the brominating agent include N-bromosuccinimide, N-iodosuccinimide, and N-chlorosuccinimide. The brominating agent is preferably used in combination with a radical initiator, such as azobisisobutyronitrile, benzoyl peroxide, or the like.

A solvent is not necessarily used, but various organic solvents can be used. Particularly, benzene, carbon tetrachloride are preferably used.

The reaction temperature may be appropriately selected from room temperature to a reflux temperature of a solvent.

The thus obtained halogenated product may be used as the leaving substituent-containing compound.

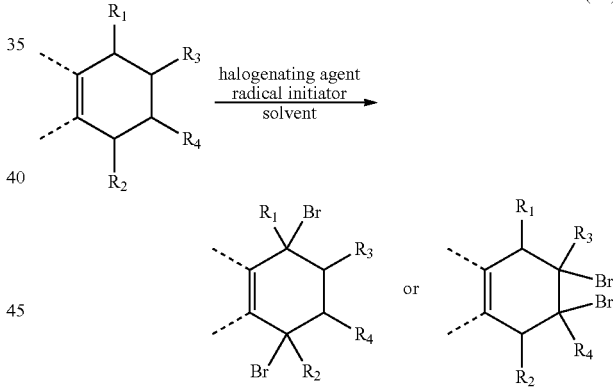

General Formula (XI)

Next, as shown in General Formula (XII), to a dihalogenated product obtained by the above reaction, two equivalents of silver carboxylate or carboxylic acid quaternary ammonium salt is made to act on, so as to obtain a compound of interest in which positions 1 and 4 and/or positions 2 and 3 are acyloxylated.

Alternatively, one equivalent of silver carboxylate or one equivalent of carboxylic acid quaternary ammonium salt is alternately made to act on a dihalogenated product so as to obtain an unsymmetrical compound.

However, since there is a possibility that the reaction speed in elimination reaction may largely vary, the carboxylic acids used are preferably the same.

A plurality of stereoisomers can be generated depending on the reaction conditions or the structure of carboxylic acid used. Specifically, a racemic mixture and a meso form may be obtained at any ratio, depending on a steric configuration of an acyloxy group bonded with a cyclohexene ring. Elimination reaction may be outstandingly retarded, depending on a steric configuration of an acyloxy group and a hydrogen atom at positions 1 and 4 and/or positions 2 and 3. Thus, preferred configuration is a configuration for accelerating the reaction as fast as possible. That is, the positional relation between the substituents at positions 1 and 4 and/or positions 2 and 3 are preferably in a cis form, in which the substituents are located on the same side of the cyclohexene plane. On the other hand, even though the substituents are in a trans form, the reaction proceeds, but reaction speed is very slow. Thus, applicability of the trans form is low.

The isomers can be separated by chromatography by recrystallization or using an optically active fixed bed. Examples of the silver carboxylate salt include silver acetate, silver trifluoroacetate, a 3,3,3-trifluoropropionic acid silver salt. Examples of carboxylic acid quaternary ammonium salt include salt formed by tetramethylammonium hydroxide pentahydrate and the aforementioned carboxylic acid (for example, acetic acid, lactic acid, valeric acid, propionic acid, pivalic acid, caproic acid, stearic acid, trifluoroacetic acid, 3,3,3-trifluoropropionic acid). As a solvent, various organic solvents, such as dimethylformamide, dimethyl sulfoxide, tetrahydrofuran, acetone, toluene, and the like can be used. From the viewpoint of reaction speed and prevention of secondary reaction, anhydrous solvents are preferably used.

The reaction temperature may be room temperature to a reflux temperature of a solvent. In order to prevent secondary reaction, such as elimination reaction, the reaction temperature is preferably 50° C. or lower, more preferably 25° C. (room temperature) or lower.

General Formula (XII)

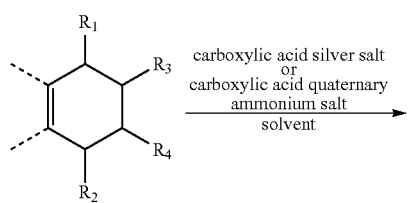

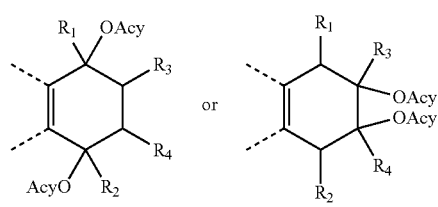

in General Formula (XII), Acy denotes an acyl group; $R_1$ to $R_4$ are the same as described above.

When the carbonate structure is synthesized, it is easy to use alkyl chloroformate in terms of material relation. As shown in General Formula (XV), the acyloxy compound is preferably converted into diol which has been hydrolyzed with bases or the like. An acyl group used in the present invention is preferably acetate or propionate, which are easily hydrolyzed.

General Formula (XV)

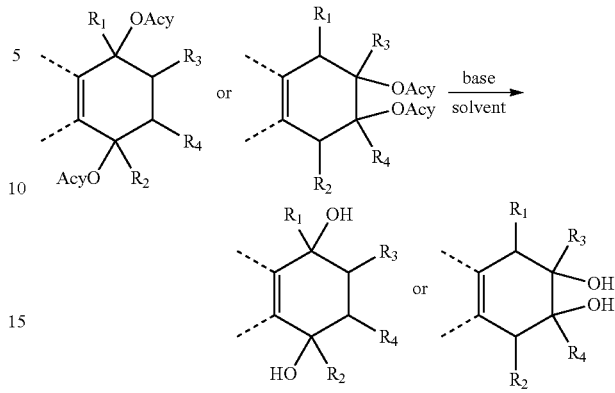

In General Formula (XV), as the solvent, alcohol, acetone, dimethylformamide or the like are preferably used. As the base, strong base, such as lithium hydroxide, sodium hydroxide, potassium hydroxide, potassium carbonate, sodium hydride, sodium methoxide, or the like are preferably used. The reaction temperature is preferably 0° C. to approximately room temperature in order to prevent secondary reaction.

Thereafter, as shown in General Formula (XVI), a hydroxyl group is acylated.

General Formula (XVI)

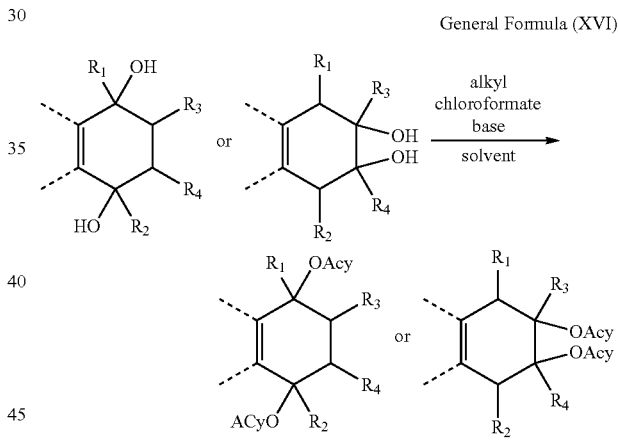

In General Formula (XVI), the solvent is not particularly limited as long as it does not react with alkyl chloroformate and sufficiently dissolves a reactant. Examples thereof include tetrahydrofuran, pyridine, dichloromethane, chloroform, and toluene. Sufficiently dehydrated thereof are preferably used.

Moreover, a base is preferably added to the solvent in order to remove hydrogen chloride generated upon reaction.

Examples of the base include pyridine, triethylamine, diisopropylamine, diisopropylethylamine, and N,N-dimethylaminopyridine. These may be used as a solvent, or used in combination thereof. As one example, the combination of pyridine or triethylamine with N,N-dimethylaminopyridine is preferable.

Examples of alkyl chloroformate include methyl chloroformate, ethyl chloroformate, propyl chloroformate, isopropyl chloroformate, and isobutyl chloroformate.

The reaction temperature is preferably 0° C. to approximately room temperature from the standpoints of reactivity and selectivity.

Thus, the carbonate structure can be formed.

The thus obtained soluble substituent is ring-fused by various conventional methods, so as to synthesize a leaving substituent-containing compound. When the leaving substituent-containing compound is used as an organic semiconductor precursor compound, for example, heteroacenes are ring-fused in the following scheme according to a method described in J. Am. Chem. Soc. 2007, 129, pp. 2224-2225.

1,4-Diacyloxy-6-iodo-1,2,3,4-tetrahydronaphthalene can be synthesized according to Synthesis Example.

As a first step, a Grignard exchange reaction is performed between an iodine atom and a Grignard reagent. Because of cryogenic reaction temperature and high reactivity of iodine, the Grignard exchange reaction selectively occurs so as to obtain a Grignard reagent.

To the Grignard reagent, a formylation agent, such as dimethylformamide or morpholine, is added so as to perform formylation.

The second step is ortho-lithiation of a formyl group. Since amine and lithium added at the same time form a complex with the formyl group, the ortho position (position 7 of tetrahydronaphthalene) is selectively lithiated without impairing other functional groups. To the lithiated formyl group, dimethyl sulfide is added, so as to form a SMe group.

Thereafter, in the third step, the formyl groups are subjected to McMurry Coupling reaction. The reaction is performed in the presence of zinc and titanium tetrachloride. Therefore, the formyl groups are coupled to form an olefin structure.

In the final step, ring-closing reaction with iodine is performed. Iodine is attached to a double bond portion, reacted with the SMe group, and eliminated in the form of MeI, to thereby form two thiophene rings. Thus, a desired ring-fused compound can be obtained.

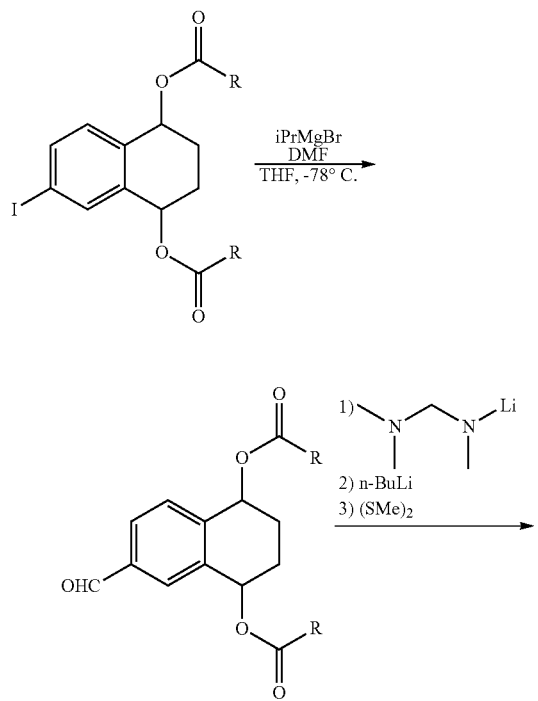

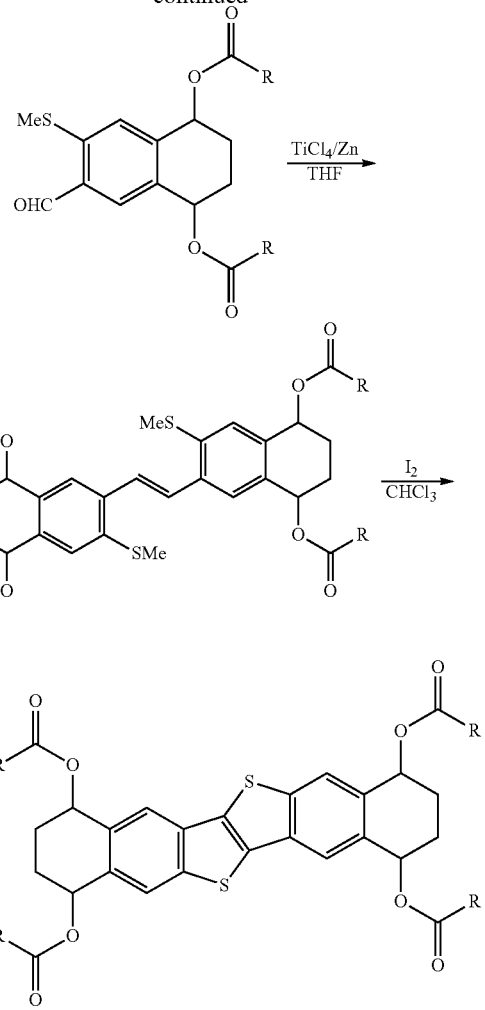

Pentacene is ring-fused in accordance with the method described in J. Am. Chem. Soc., 129, 2007, pp. 15752. In the case of phthalocyanines, ring formation reaction can be performed in accordance with "Phthalocyanine—chemical and function—", Hirofusa Shirai, Nagao Kobayashi, 1997, (IPC) pp. 1 to 62, and "Phthalocyanine as a functional dye" Ryo Hirohashi, Keiichi Sakamoto, Eiko Okumura, 2004 (IPC) pp. 29 to 77. Porphyrins are ring-fused in accordance with the method described in JP-A No. 2009-105336.

The leaving substituent-containing compound of the present invention is bonded via a covalent bond to other skeletons of the solvent-soluble substituents (B in General Formula (XIV)) by known methods for coupling reaction. Examples of the known coupling reactions include Suzuki coupling reaction, Stille coupling reaction, Kumada coupling reaction, Negishi coupling reaction, Hiyama coupling reaction, Sonogashira reaction, Heck reaction and Wittig reaction. Of these, Suzuki coupling reaction and Stille coupling reaction are particularly preferred in terms of easy derivatization of an intermediate, reactivity and yield. For formation of carbon-carbon double bond, Heck reaction, and Wittig reaction are preferable in addition to the above-described reactions. For formation of carbon-carbon triple bond, Sonogashira reaction is preferable in addition to the above-described reactions.

Hereinafter, an embodiment in which a carbon-carbon bond is formed by Suzuki coupling reaction and Stille coupling reaction will be described.

The reaction is performed using a combination of a halogenated product with a trifluoro triflate product, or a combination of a boronic acid derivative with an organotin derivative. However, in the case where the compounds represented by General Formula (XV) and (XVI) are both a halogenated product and a triflate product, or a boronic acid derivative and an organotin derivative, coupling reaction does not occur. Such cases are excluded.

In the mixture described above, base is further added only in the case of Suzuki coupling reaction, and the mixture is reacted in the presence of a palladium catalyst.

$$Ar\text{-}(A)_l \qquad \text{General Formula (XIII)}$$

in General Formula (XIII), Ar denotes an aryl group or a heteroaryl group, as described above; A denotes a halogen atom (a chlorine atom, a bromine atom, or an iodine atom), a triflate (trifluoromethanesulfonyl) group, boronic acid or ester thereof, or an organotin functional group; l denotes an integer of 1 or more.

$$B\text{-}(C)_k \qquad \text{General Formula (XIV)}$$

in General Formula (XIV), B denotes a solvent soluble substituent as described above; C denotes a halogen atom (a chlorine atom, a bromine atom, or an iodine atom), a triflate (trifluoromethanesulfonyl) group, boronic acid or ester thereof, or an organotin functional group; k denotes an integer of 1 or more.

In the synthesis method by Suzuki coupling reaction, Stille coupling reaction, among halogenated products or triflate products in General Formulas (XIII) and (XIV), iodine products, bromine products, and triflate products are preferable, from the standpoint of reactivity.

As the organotin functional group in General Formulas (XIII) and (XIV), a derivative having an alkyl tin group such as a $SnMe_3$ group or a $SnBu_3$ group can be used. The derivatives can be easily obtained in such a manner that hydrogen or a halogen atom in a desired position is replaced with lithium or a Grignard reagent using an organic metal reagent such as n-butyllithium, followed by quenching using trimethyltin chloride or tributyltin chloride.

As the boronic acid derivative, in addition to a boronic acid, a boronic ester derivative may be used. The boronic ester derivative is synthesized from a halogenated derivative using bis(pinacolato)diboron which has thermal stability and is easily handled in air, or synthesized by protecting boronic acid with diol such as pinacol.

As described above, either the substituent A or the substituent B may be halogen and a triflate product, or a boronic acid derivative and an organotin derivative. From the standpoints of easiness of derivatization and reduction of secondary reaction, it is preferred that the substituent A be a boronic acid derivative and an organotin derivative.

For the Stille coupling, reaction base is not necessary, while for the Suzuki coupling reaction base is necessary, and a relatively weak base, such as $Na_2CO_3$, or $NaHCO_3$ contributes to a good result. In the case where steric hindrance effects on the reaction, a strong base such as $Ba(OH)_2$, $K_3PO_4$ or $NaOH$ is effective. Additionally, caustic potash and metal alkoxides, such as potassium t-butoxide, sodium t-butoxide, lithium t-butoxide, potassium 2-methyl-2-butoxide, sodium 2-methy-2-butoxide, sodium methoxide, sodium ethoxide, potassium ethoxide and potassium methoxide may be also used as the bases. Moreover, organic bases such as triethylamine may be also used.

Examples of the palladium catalysts include palladium bromide, palladium chloride, palladium iodide, palladium cyanide, palladium acetate, palladium trifluoroacetate, palladium acetyl acetonato[$Pd(acac)_2$], diacetate bis(triphenylphosphine)palladium[$Pd(OAc)_2(PPh_3)_2$], tetrakis(triphenylphosphine)palladium[$Pd(PPh_3)_4$], dichloro bis(acetonitrile)palladium[$Pd(CH_3CN)_2Cl_2$], dichloro bis(benzonitrile)palladium[$Pd(PhCN)_2Cl_2$], dichloro[1,2-bis(diphenylphosphino)ethane]palladium[$Pd(dppe)Cl_2$], dichloro[1,1-bis(diphenylphosphino)ferrocene]palladium [$Pd(dppf)Cl_2$], dichloro bis(tricyclohexylphosphine)palladium[$Pd[P(C_6H_{11})_3]_2Cl_2$], dichloro bis(triphenylphosphine)palladium[$Pd(PPh_3)_2Cl_2$], tris(dibenzylideneacetone)dipalladium[$Pd_2(dba)_3$], and bis(dibenzylideneacetone)palladium[$Pd(dba)_2$]. Of these, phosphine catalysts such as tetrakis(triphenylphosphine)palladium[$Pd(PPh_3)_4$], dichloro[1,2-bis(diphenylphosphino)ethane]palladium [$Pd(dppe)Cl_2$], dichloro bis(triphenylphosphine)palladium[$Pd(PPh_3)_2Cl_2$] are preferred.

In addition to the above-described palladium catalysts, a palladium catalyst synthesized by reaction of a palladium complex and a ligand in a reaction system can be also used. Example of the ligands include triphenylphosphine, trimethylphosphine, triethylphosphine, tris(n-butyl)phosphine, tris(tert-butyl)phosphine, bis(tert-butyl)methylphosphine, tris(i-propyl)phosphine, tricyclohexylphosphine, tris(o-tolyl)phosphine, tris(2-furyl)phosphine, 2-dicyclohexylphosphinobiphenyl, 2-dicyclohexylphosphino-2'-methylbiphenyl, 2-dicyclohexylphosphino-2',4',6'-triisopropyl-1,1'-biphenyl, 2-dicyclohexylphosphino-2',6'-dimethoxy-1,1'-biphenyl, 2-dicyclohexylphosphino-2'-(N,N'-dimethylamino)biphenyl, 2-diphenylphosphino-2'-(N,N'-dimethylamino)biphenyl, 2-(di-tert-butyl)phosphine-2'-(N,N'-dimethylamino)biphenyl, 2-(di-tert-butyl)phosphinobiphenyl, 2-(di-tert-butyl)phosphino-2'-methylbiphenyl, diphenylphosphino ethane, diphenylphosphino propane, diphenylphosphino butane, diphenylphosphino ethylene, diphenylphosphino ferrocene, ethylenediamine, N,N',N'',N'''-tetramethylethylenediamine, 2,2'-bipyridyl, 1,3-diphenyldihydro imidazolylidene, 1,3-dimethyl dihydroimidazolylidene, diethyl dihydroimidazolylidene, 1,3-bis(2,4,6-trimethylphenyl)dihydroimidazolylidene and 1,3-bis(2,6-diisopropylphenyl)dihydroimidazolylidene. A palladium catalyst in which any of these ligands coordinates can be used as a cross coupling catalyst.

A reaction solvent preferably has no functional group reactive with a raw material and can appropriately dissolve the raw material. Examples thereof include: water; alcohols and ethers such as methanol, ethanol, isopropanol, butanol, 2-methoxyethanol, 1,2-dimethoxyethane, bis(2-methoxyethyl)ether; cyclic ethers such as dioxane, tetrahydrofuran; benzene; toluene; xylene; chlorobenzene; dichlorobenzene; dimethyl sulfoxide (DMSO); N,N-dimethylformamide (DMF); N,N-dimethylacetamide; N-methylpyrrolidone; and 1,3-dimethyl-2-imidazolidinone. These solvents may be used alone or in combination. Moreover, it is preferred that these solvents be preliminarily dried and deaerated.

The temperature of the above-described reaction may be appropriately set depending on the reactivity of a raw material used or a reaction solvent. It is generally 0° C. to 200° C. However, the upper limit of the temperature is preferably a boiling point or lower of the solvent in any case. Additionally, the temperature is preferably set at a temperature at which elimination reaction occurs or lower in terms of yield.

The lower limit of the temperature may be a melting point of the solvent. However, when the temperature is excessively low, the reaction speed is outstandingly lowered, and it is not preferable. Specifically, it is preferably 0° C. to 150° C., more preferably 0° C. to 100° C., and particularly preferably room temperature to 80° C.

The reaction time of the above reaction may be approximately set depending on the reactivity of a raw material used. It is preferably 1 hour to 72 hours, and more preferably 1 hour to 24 hours.

The thus obtained leaving substituent-containing compound represented by Ar—(B)m (m is an integer of 1 or more) is used by removing impurities such as the catalyst used for reaction, unreacted raw materials, or by-products generated upon reaction such as boronic acid salts, organotin derivatives or the like. For the purification, conventionally known methods may be used, for example, reprecipitation, column chromatography, adsorption, extraction (including Soxhlet extraction), ultrafiltration, dialysis, use of scavenger for removing a catalyst, or the like. Like the compound of the present invention, materials having excellent solubility reduce limitation of these purification method. As a result, such materials favorably effect on device properties.

In order to deposit a thin film from the leaving substituent-containing compound obtained by the above-described production method, conventionally known film deposition methods may be used, for example, spin coating, casting, dipping, inkjetting, doctor blade casting, screen printing, vacuum deposition, or sputtering. Any of these methods enables to deposit a good thin film having excellent strength, toughness, durability and the like without cracks. Moreover, an external stimulus is applied to the film of the leaving substituent-containing compound of the present invention deposited by the film deposition method, so as to eliminate a soluble substituent, thereby depositing an organic semiconductor film. The leaving substituent-containing compound may be used as various materials for functional elements such as photoelectric conversion elements, thin-film transistor elements, light-emitting elements and the like, (Application of Leaving Substituent-Containing Compound to Device)

An organic semiconductor compound produced from the leaving substituent-containing compound of the present invention can be used in an electronic device. Examples of the electronic devices include devices having two or more electrodes in which current and voltage between the electrodes are controlled by electricity, light, magnetism, chemical materials or the like; and apparatuses for generating light, electrical field, or magnetic field by application of voltage or current. Moreover, examples thereof include elements for controlling current or voltage by application of voltage or current, elements for controlling voltage or current by application of magnetic field, and elements for controlling voltage or current by action of a chemical material. For control, rectification, switching, amplification, oscillation or the like are used.

As a device currently realized using an inorganic semiconductor such as silicon or the like, resistors, rectifiers (diode), switching elements (transistor, thyristor), amplifying elements (transistor), memory elements, chemical sensors or the like, combinations of these elements, integrated devices, or the like are exemplified. Additionally, solar batteries in which electromotive force generated by light, photodiodes for generating photocurrent, photoelements such as phototransistors or the like are used.

As an electronic device, to which the leaving substituent-containing compound of the present invention and the organic semiconductor compound produced by using the leaving substituent-containing compound are applied, an organic thin-film transistor, namely organic field effect transistor (OFET) is exemplified. Hereinafter, field effect transistor (FET) will be specifically described.

Structure of Transistor

FIGS. 4A to 4D show schematic structures of organic thin-film transistors of the present invention. An organic semiconductor layer 1 of the organic thin-film transistor contains the organic semiconductor compound. The organic thin-film transistor of the present invention includes a first electrode (source electrode 2), a second electrode (drain electrode 3) and a third electrode (gate electrode 4), which are provided on a support (substrate) (not shown) with being separated each other. A gate insulating film 5 may be provided between the gate electrode 4 and the organic semiconductor layer 1. The organic thin-film transistor is configured to control the current flowing through the organic semiconductor layer 1 between the source electrode 2 and the drain electrode 3 by applying voltage to the gate electrode 4. It is important for a switching element to largely modulate the amount of the current flowing between the source electrode 2 and the drain electrode 3 by the conditions of applying voltage from the gate electrode 4. This means that large current flows depending on the drive state of the transistor, and no current flows in non drive state of the transistor.

The organic thin-film transistor of the present invention may be formed on the substrate. As the substrate, a typical substrate formed of, for example, glass, silicon, plastic or the like may be used. A conductive substrate can be used to serve as the gate electrode. The gate electrode and the conductive substrate may be layered. However, a plastic sheet is preferably used as the substrate in case where a device, to which the organic thin-film transistor is applied, is expected to have properties such as flexibility, lightweight, lower production cost and shock resistance.

Examples of the plastic sheets include films of polyethylene terephthalate, polyethylene naphthalate, polyether sulfone, polyetherimide, polyether ether ketone, polyphenylene sulfide, polyarylate, polyimide, polycarbonate, cellulose triacetate, and cellulose acetate propionate.

Film Deposition Method: Organic Semiconductor Layer

Additionally, the leaving substituent-containing compound of the present invention is used as an organic semiconductor precursor, and the organic semiconductor precursor is dissolved in a solvent such as dichloromethane, tetrahydrofuran, chloroform, toluene, chlorobenzene, dichlorobenzene and/or xylene, and applied on a substrate so as to deposit a thin film. The application of an energy to the thin film formed of the organic semiconductor precursor, to thereby converted into an organic semiconductor film.

The leaving substituent-containing compound of the present invention has a cyclohexane structure and an acyloxy group, which is sterically bulky, and poor crystallinity. A molecule having such structure excels in solubility and has properties of easily obtaining a film having low crystallinity (amorphous), when a solution containing the molecule is applied.

Examples of methods for depositing the thin films include spray coating, spin coating, blade coating, dipping, casting, roll coating, bar coating, dye coating, inkjetting and dispensing; printing methods such as screen printing, offset printing, relief printing, flexographic printing; soft lithography such as a micro contact printing. Moreover, these methods may be used in combination.

From the above-described deposition methods and solvents, a deposition method and solvent may be appropriately selected according to materials. The organic semiconductor material which has been thermally converted can deposit a film through vapor phase, such as vacuum deposition.

In the organic thin-film transistor of the present invention, the thickness of the organic semiconductor layer is not particularly limited, and the thickness of the organic semiconductor layer is so selected as to deposit a uniform thin film, namely, a thin film having no gaps and holes that adversely affect the carrier transportation characteristics of the organic semiconductor layer.

The thickness of the organic semiconductor layer is generally 1 µm or less, and particularly preferably 5 nm to 100 nm. In the organic thin-film transistor of the present invention, the organic semiconductor layer deposited from the above mentioned compounds is formed in contact with the source electrode, the drain electrode, and the insulating film.

Film Deposition Method: Post Treatment of Organic Semiconductor Film

The properties of the organic semiconductor film converted from the precursor-containing thin film can be improved by post treatment. For example, deformation of the film caused during film deposition can be reduced by heat treatment. This heat treatment enhances the crystallinity, and the properties are improved and stabilized. Moreover, the organic semiconductor film is placed in an organic solvent (such as toluene and chloroform), so that the deformation of the film can be reduced in the same manner as in heat treatment, and the crystallinity can be further enhanced.

Moreover, by exposing the organic semiconductor film to oxidizing or reducing air and/or liquid, such as oxygen, hydrogen, etc. properties can be changed by oxidization or reduction. The oxidization or reduction is used for the purpose of increasing or decreasing the density of carrier in the film.

Electrode

The materials of the gate electrode and the source electrode used in the organic thin-film transistor of the present invention are not particularly limited, as long as conductive materials are used. Examples thereof include platinum, gold, silver, nickel, chromium, copper, iron, tin, antimony, lead, tantalum, indium, aluminum, zinc, magnesium, and alloys thereof; conductive metal oxides such as indium/tin oxides; organic and inorganic semiconductors in which conductivity is improved by doping, etc., such as a silicon single crystal, polysilicon, amorphous silicon, germanium, graphite, polyacetylene, polyparaphenylene, polythiophene, polypyrrol, polyaniline, polythienylene vinylene, polyparaphenylene vinylene, complexes consisting of polyethylene dioxythiophene and polystyrene sulfonic acid.

Of the conductive materials described above, materials having a low electric resistance at the surface in contact with the semiconductor layer are preferred for the source electrode and drain electrode.

Examples of methods for forming an electrode include a method in which a conductive thin film, which has been deposited using the material mentioned above by deposition or sputtering, is formed into an electrode by a known method such as a photolithographic method or liftoff technology; and a method in which an electrode is formed by etching a resist on a metal foil of, for example, aluminum and copper, by thermal transfer, inkjet or the like. In addition, an electrode may be formed by directly patterning by inkjet printing using a solution or dispersion liquid of a conductive polymer or a dispersion liquid of conductive particles, or may be formed from a coated layer by lithography or laser ablation. It is also possible to use a method in which an ink, conductive paste, etc. containing conductive polymers or conductive particles are patterned by a printing method such as relief printing, intaglio printing, planographic printing or screen printing.

The organic thin-film transistor of the present invention can have an extraction electrode from each electrode if necessary.

Insulating Film

The insulating film used in the organic thin-film transistor of the present invention is formed of various materials for insulating film. Examples thereof include the inorganic insulating materials such as silicon oxide, silicon nitride, aluminum oxide, aluminum nitride, titanium oxide, tantalum oxide, tin oxide, vanadium oxide, barium-strontium-titanium oxide, barium-titanium-zirconium oxide, lead-zirconium-titanium oxide, lead lanthanum titanate, strontium titanate, barium titanate, barium magnesium fluoride, bismuth-niobium-tantalum oxide and yttrium trioxide.

Additionally, examples thereof include polymer compounds such as polyimides, polyvinyl alcohols, polyvinyl phenols, polyesters, polyethylene, polyphenylenesulfides, unsubstituted or halogen atom substituted polyparaxylylene, polyacrylonitrile and cyanoethylpullulan.

These insulating materials may be used in combination. The insulating material is not particularly limited, and it is preferred to select an insulating material having a high dielectric constant and a low conductivity.

Examples of the methods of depositing the insulating film using the insulating materials include dry deposition processes such as a chemical vacuum deposition (CVD), a plasma CVD, a plasma polymerization and vapor deposition; and wet coating processes such as spray coating, spin coating, dip coating, inkjetting, casting, blade coating and bar coating.

Modification of Interface between Organic Semiconductor and Insulating Film (HMDS, etc.)

In the organic thin-film transistor of the present invention, the organic thin film may be provided between the insulating film, electrode and the organic semiconductor layer to improve adhesiveness thereof, decrease gate voltage and reduce leak current. The organic thin film is not particularly limited as long as the organic thin film does not have a chemical effect on an organic semiconductor layer. For example, an organic molecular film and a polymer thin film can be used.

In the case of the organic molecular film, coupling agents such as octyltrichlorosilane, octadecyl trichlorosilane, hexamethylene disilazane and phenyltrichlorosilane, benzenethiol, trifluorobenzenethiol, perfluorobenzenethiol, perfluorodecanethiol, etc. may be used. In addition, as the polymer thin film, the aforementioned polymer insulating materials can be used, and these may function as a sort of the insulating film. This organic thin film may be subject to an anisotropic treatment by rubbing or the like.

Protective Layer

The organic thin-film transistor of the present invention can be stably driven in the atmosphere. If necessary, a protective layer can be provided in terms of protection from mechanical destruction and moisture and/or gas, and protection for integration of a device for convenience.

Applied Device

The organic thin-film transistors of the present invention can be utilized as an element for driving various known image display elements such as liquid crystal, electroluminescence, electrochromic, and electrophoretic migration. When such elements are integrated, it is possible to produce a display referred to as "electronic paper".

The display device includes liquid crystal display elements in the case of a liquid display device, organic or inorganic electroluminescence display elements in the case of an EL display device, and electrophoresis display elements in the case of an electrophoresis display device, and a plurality of such display elements are aligned in the form of matrix in X direction and Y direction to construct the display device using the aforementioned display element as one display picture element (i.e. one pixel). The display element is equipped with the organic thin film transistor of the present invention as a switching element for applying voltage or supplying a current to the display element. The display device includes the same number of the switching elements to the number of the display element, i.e. the number of the display picture elements (i.e., the pixels).

The display element contains, other than the switching elements, members such as a substrate, an electrode (e.g., a transparent electrode), a polarizer, and a color filter. These members are suitably selected from those known in the art depending on the intended purpose without any restriction.

When the display device forms a certain image, only certain switching elements selected from all the switching elements provided in the matrix form turn on or off for applying voltage or a current to the corresponding display elements. When voltage or a current is not applied to the display elements, all the switching elements remain the state of OFF or ON. The display device can display the image at high speed and high contrast by having such configuration. Note that, the display device displays an image by the conventional display operation known in the art.

For example, in the case of the liquid display element, the molecule alignments of the liquid crystals are controlled by applying voltage to the liquid crystals, to thereby display an image or the like. In the case of the organic or inorganic electroluminescence display element, a current is supplied to a light-emitting diode formed of an organic material or inorganic material to emit the organic or inorganic film, to thereby display an image or the like. In the case of the electrophoresis display element, voltage is applied to white coloring particles and black coloring particles each charged with the opposite polarity to each other to make the coloring particles electrically migrate in a certain direction. As a result, an image or the like is displayed.

The display device can be produced by a simple process, such as a process of coating or printing the switching element, can use as a substrate, and a plastic substrate or paper that does not have sufficient resistance to a high temperature processing. Moreover, the display device having a large area can be produced at low energy and cost, as the switching elements can be formed at low energy and cost.

Moreover, it is also possible to use an IC in which the organic thin-film transistors of the present invention are integrated as a device such as an IC tag.

(π-Electron Conjugated Compound and Film-Like Product Obtained from π-Electron Conjugated Compound Precursor by a Production Method of the Present Invention)

In methods of the present invention for producing a film-like product and a π-electron conjugated compound, an external stimulus is applied to a "π-electron conjugated compound precursor" having specific solvent-soluble substituents, so that the specific solvent-soluble substituents are removed, thereby producing a film-like product and a π-electron conjugated compound of interest. The above "π-electron conjugated compound precursor" is represented by A-(B)m, where A denotes a π-electron conjugated substituent, B denotes a solvent-soluble substituent having a structure represented by the following General Formula (I-2) as at least a partial structure, and m is a natural number. Notably, in the structure represented by General Formula (I-2), the solvent-soluble substituent represented by B is linked via a covalent bond with the π-electron conjugated substituent represented by A via a carbon atom which is present on the solvent-soluble substituent represented by B and is other than those having substituents represented by $X_1$, $X_2$, $Y_1$ and $Y_2$; or is ring-fused with the π-electron conjugated substituent represented by A via the carbon atoms which are present on the solvent-soluble substituent represented by B and are other than those having substituents represented by $X_1$, $X_2$, $Y_1$ and $Y_2$.

By applying an external stimulus to the π-electron conjugated compound precursor, specific leaving substituents ($X_1$, $X_2$) and ($Y_1$, $Y_2$) are eliminated in the form of $X_1$-$Y_1$ and $X_2$-$Y_2$, and the solvent-soluble substituent B is converted to substituent C having a benzene ring structure, to thereby obtain a π-electron conjugated compound A-(C)m represented by the following General Formula (II-2). In addition, a film-like product containing this compound is obtained.

As described above, the π-electron conjugated compound precursor used in the present invention has a structure in which the π-electron conjugated substituent A is bonded to the solvent-soluble substituent B.

Here, the solvent-soluble substituent B is represented by General Formula (I-2), and the substituent C is represented by General Formula (II-2).

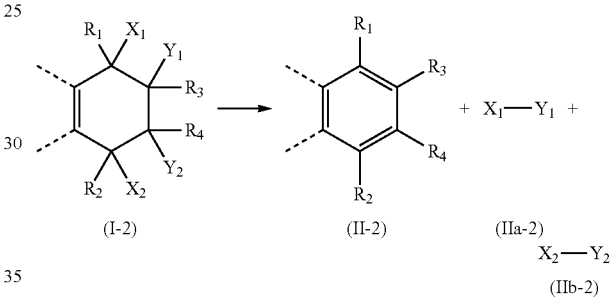

In General Formulas (I-2) and (II-2), ($X_1$, $X_2$), ($Y_1$, $Y_2$) and R1 to R4 are the same as described in relation to the leaving substituent-containing compound and the compound obtained through elimination reaction.

As described above, the π-electron conjugated compound precursor A-(B)m used in the present invention is composed of the π-electron conjugated substituent A and the solvent-soluble substituent B. In the structure represented by General Formula (I-2), the solvent-soluble substituent represented by B is linked via a covalent bond with the π-electron conjugated substituent represented by A via a carbon atom which is present on the solvent-soluble substituent represented by B and is other than those having substituents represented by $X_1$, $X_2$, $Y_1$ and $Y_2$; or is ring-fused with the π-electron conjugated substituent represented by A via the carbon atoms which are present on the solvent-soluble substituent represented by B and are other than those having substituents represented by $X_1$, $X_2$, $Y_1$ and $Y_2$.

In the methods of the present invention for producing the π-electron conjugated compound and the film-like product containing the π-electron conjugated compound, specific components $X_1Y_1$ and $X_2Y_2$ are eliminated from the precursor, so that the solvent-soluble substituent B is converted to the substituent C having a benzene ring, whereby the π-electron conjugated compound A-(C)m is obtained.

Also, solubility of the π-electron conjugated compound A-(C)m to a solvent varies with a combination of substituent A and substituent B.

The π-electron conjugated substituent A is not particularly limited, so long as it has a π-electron conjugated plane. Preferred examples thereof include a benzene ring, a thiophene ring, a pyridine ring, a pyrazine ring, a pyrimidine ring, a triazine ring, a pyrrole ring, a pyrazole ring, an imidazole ring, a triazole ring, an oxazole ring, a thiazole ring, a furan ring, a selenophene ring and a silole ring. More preferably, Ar is at least one π-electron conjugated compound selected from the group consisting of (i) aromatic hydrocarbon rings, aromatic heterocyclic rings, compounds in which one or more aromatic hydrocarbon rings are ring-fused with one or more aromatic heterocyclic rings, compounds in which two or more aromatic hydrocarbon rings are ring-fused together, and compounds in which two or more aromatic heterocyclic rings are ring-fused together; and (ii) compounds in which one or more aromatic hydrocarbon rings are linked via covalent bond with one or more aromatic heterocyclic rings, compounds in which two or more aromatic hydrocarbon rings are linked together via a covalent bond, and compounds in which two or more aromatic heterocyclic rings are linked together via a covalent bond. Further, π electrons contained in the aromatic hydrocarbon rings or aromatic heterocyclic rings are preferably delocalized throughout the ring-fused or linked structure by the interaction as a result of ring-fused linkage or covalently bonding.

The number of aromatic hydrocarbon rings and/or aromatic heterocyclic rings ring-fused or linked together via a covalent bond is preferably two or more. Specific examples thereof include fused polycyclic compounds such as naphthalene, anthracene, tetracene, chrycene, pyrene, pentacene, thienothiophene, thienodithiophene, triphenylene, hexabenzocoronene, benzothiophene, benzodithiophene, [1]benzothieno[3,2-b][1]benzothiophene (BTBT), dinaphto[2,3-b:2',3'-f][3,2-b]thienothiophene (DNTT) and benzodithienothiophene (TTPTT); oligomers of aromatic hydrocarbon rings and aromatic heterocyclic rings such as biphenyl, terphenyl, quaterphenyl, bithiophene, terthiophene and quaterthiophene; phthalocyanines; and porphyrins.

The structure of the solvent-soluble substituent B is not particularly limited, so long as it has as a partial structure a cyclohexene ring structure represented by General Formula (I-2). The following structures are exemplified.

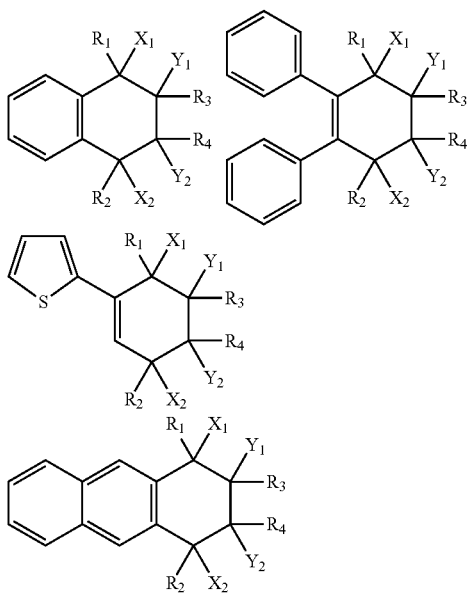

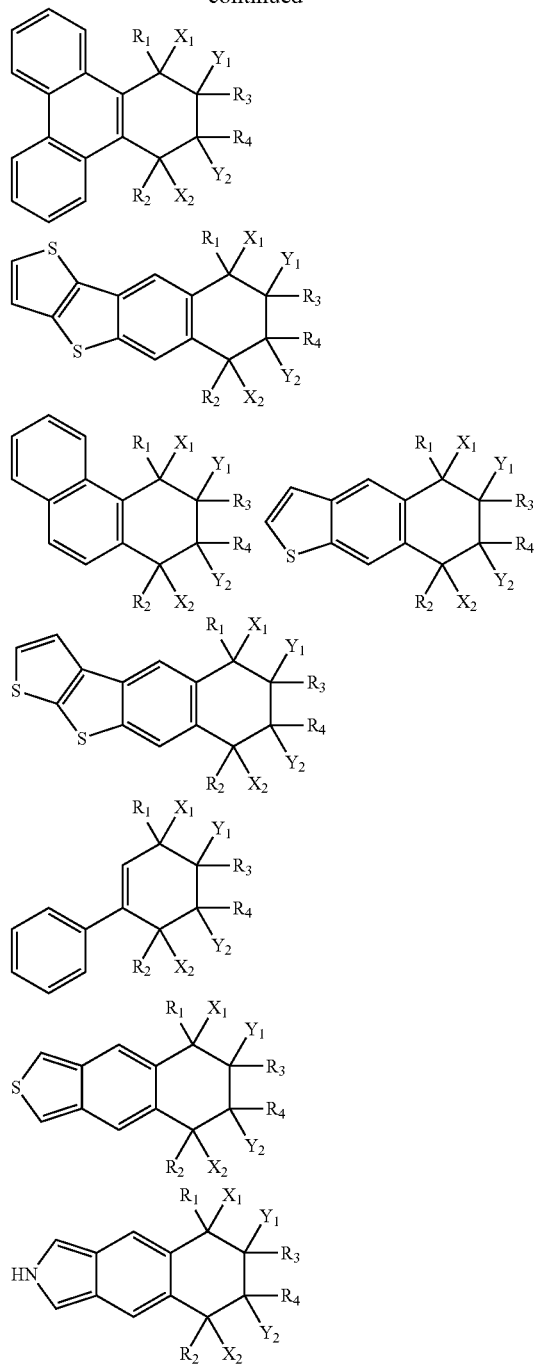

Each of the above-exemplified structures can be ring-fused with or linked via a covalent bond with the π-electron conjugated substituent A via other atoms than those having substituents $R_1$ to $R_4$, $(X_1, X_2)$ and $(Y_1, Y_2)$.

The compounds represented by A-(B)m, which are formed by combining the π-electron conjugated substituent A with the solvent-soluble substituent B, are exemplified as follows. However, the π-electron conjugated compound precursor in the present invention should not be construed as being limited thereto. Also, it is easily supposed that there are several stereoisomers of the solvent-soluble substituent B depending on the steric configuration of acyloxy groups, and that the following compounds are mixtures of such stereoisomers.

Exemplary compound 1
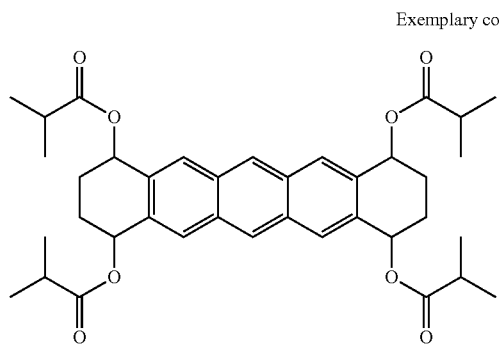
Exemplary compound 2
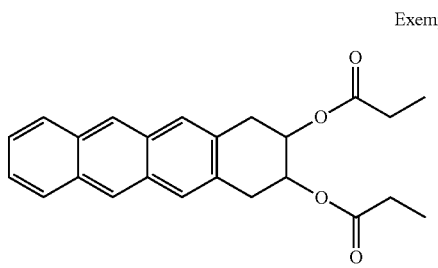
Exemplary compound 3
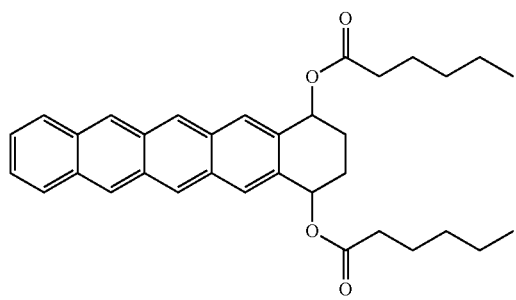
Exemplary compound 4
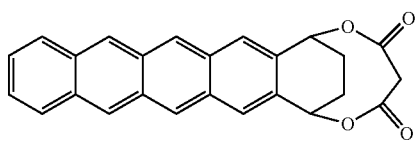
Exemplary compound 5
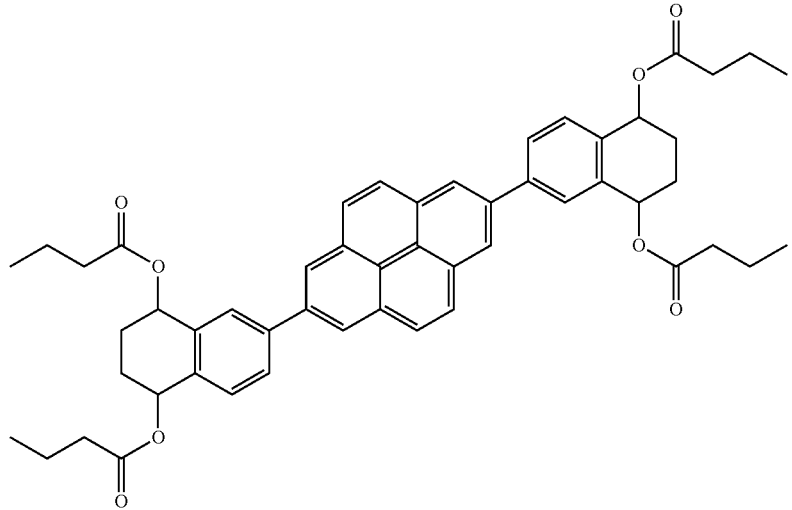
Exemplary compound 6
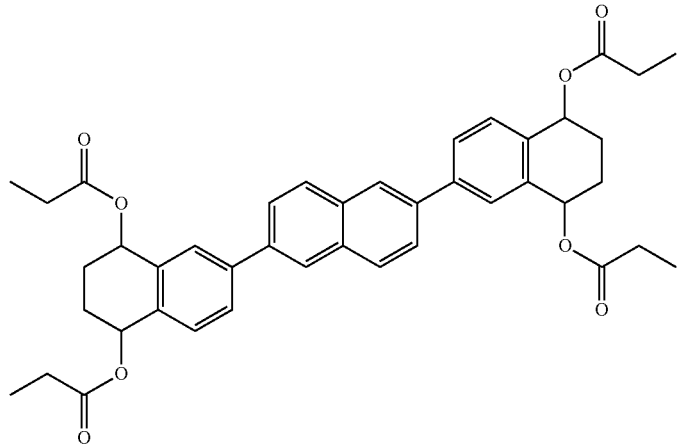

-continued
Exemplary compound 7
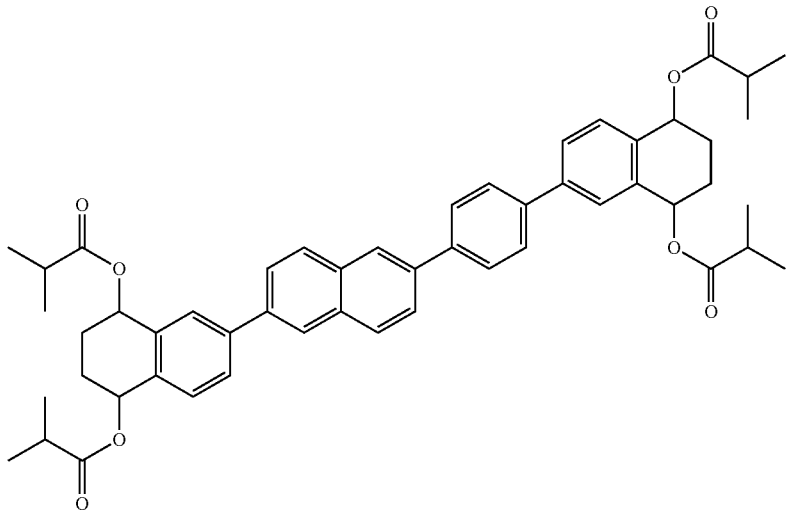
Exemplary compound 8
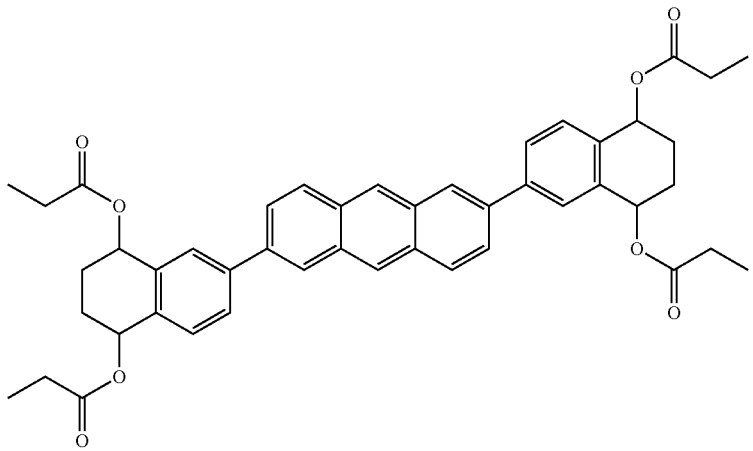
Exemplary compound 9
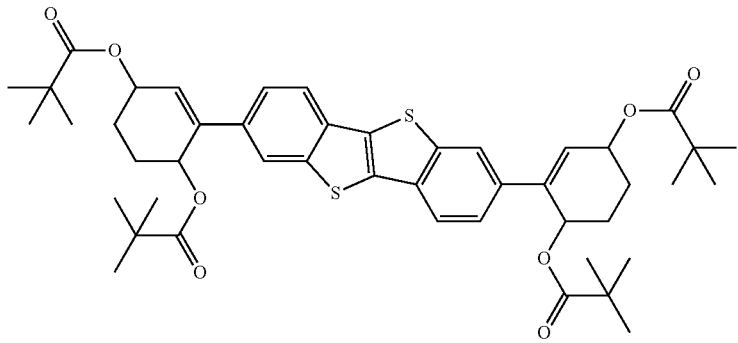
Exemplary compound 10
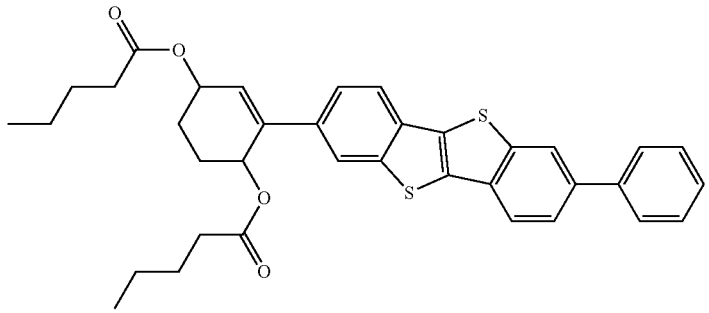

-continued
Exemplary compound 11
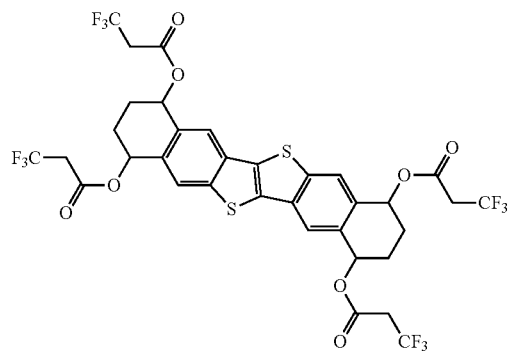
Exemplary compound 12
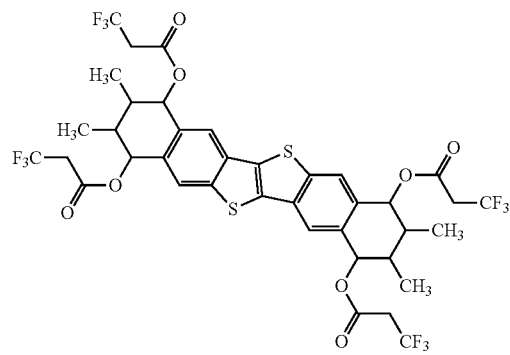
Exemplary compound 13
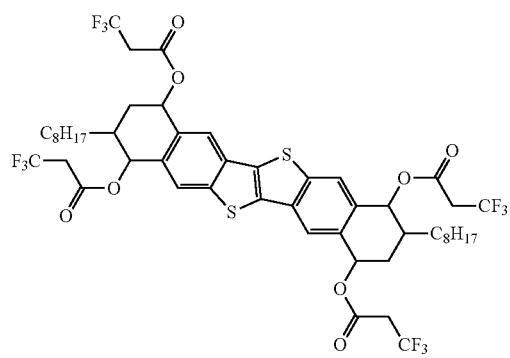
Exemplary compound 14
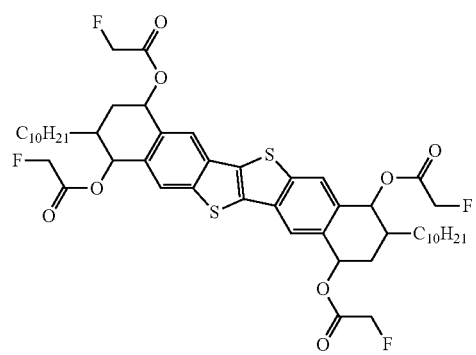
Exemplary compound 15
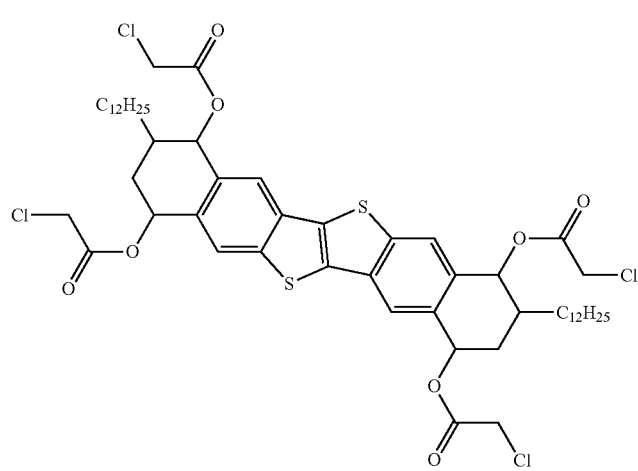
Exemplary compound 16
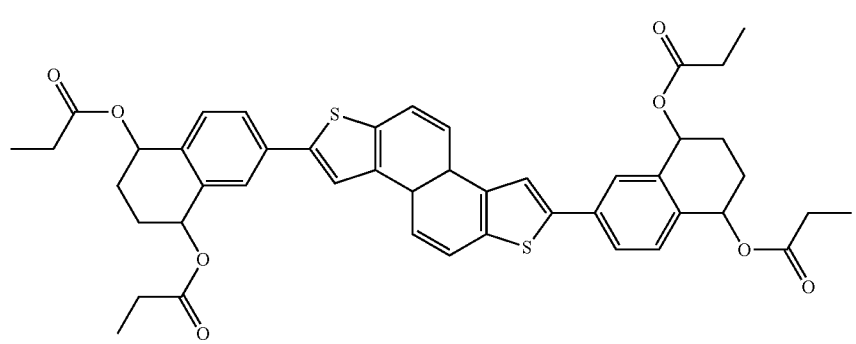

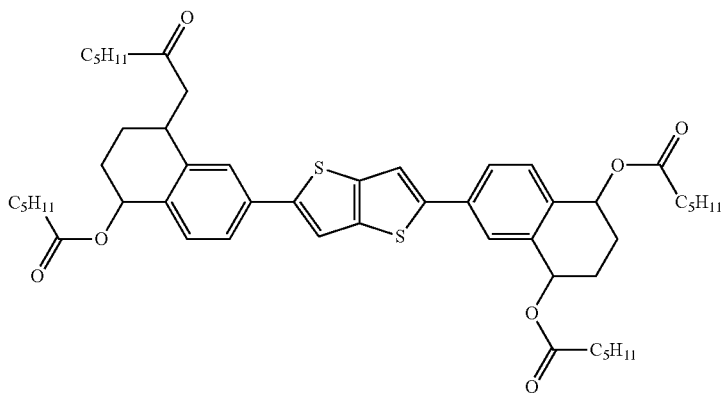
Exemplary compound 17
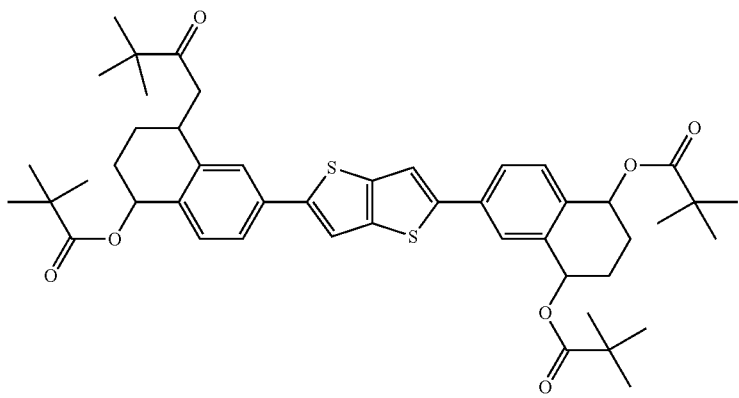
Exemplary compound 18
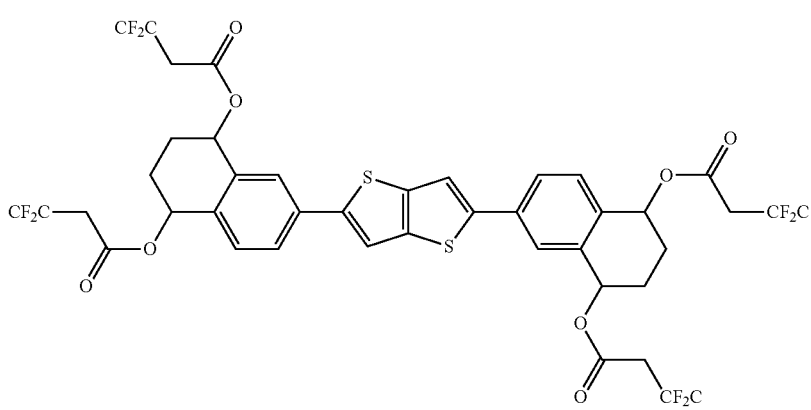
Exemplary compound 19
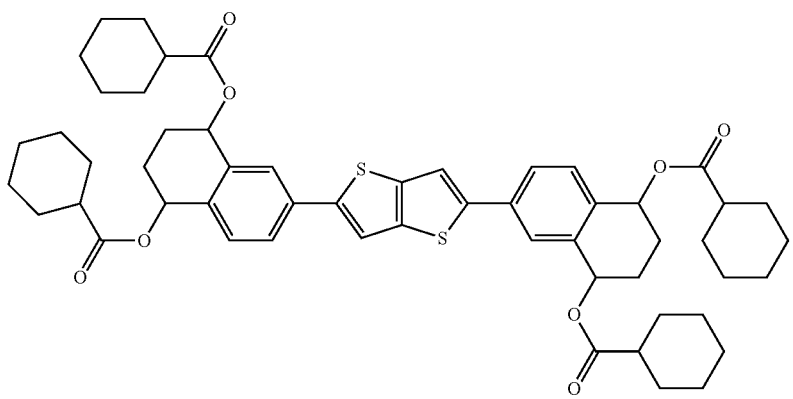
Exemplary compound 20

Exemplary compound 21
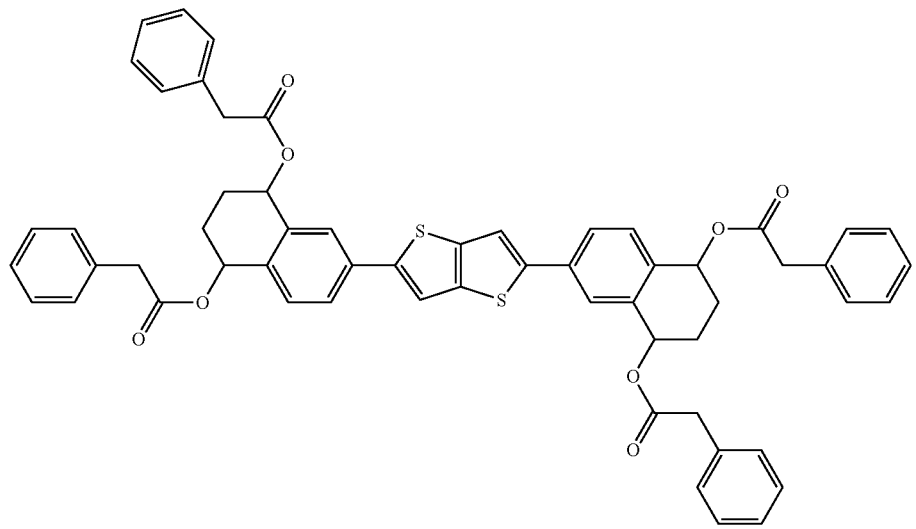
Exemplary compound 22
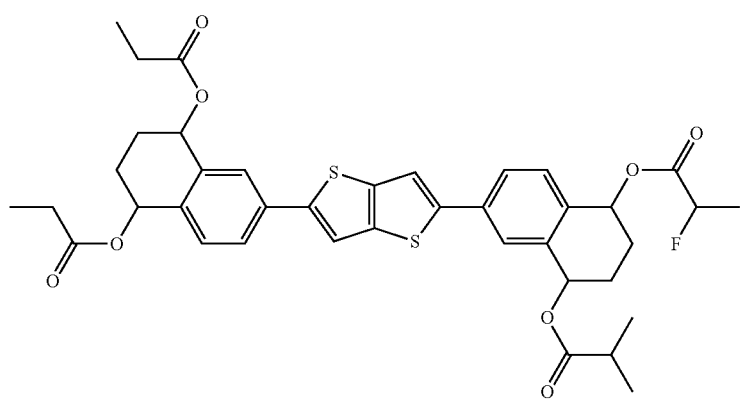
Exemplary compound 23
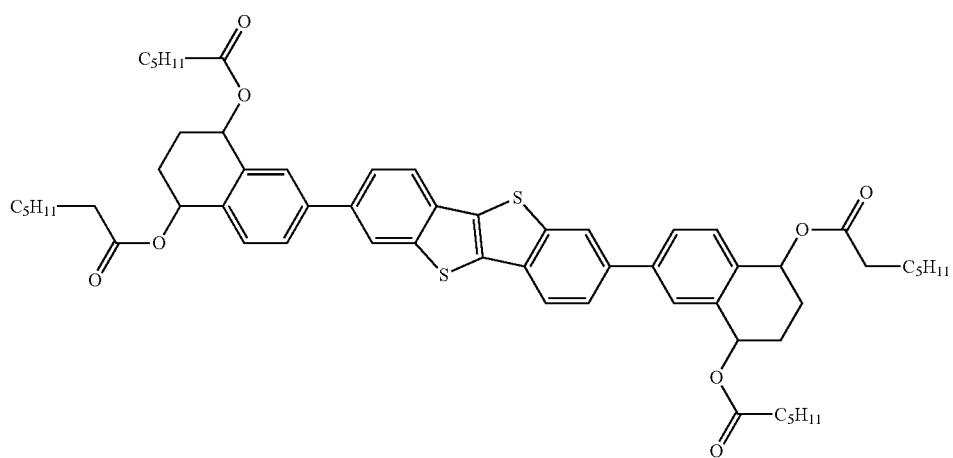

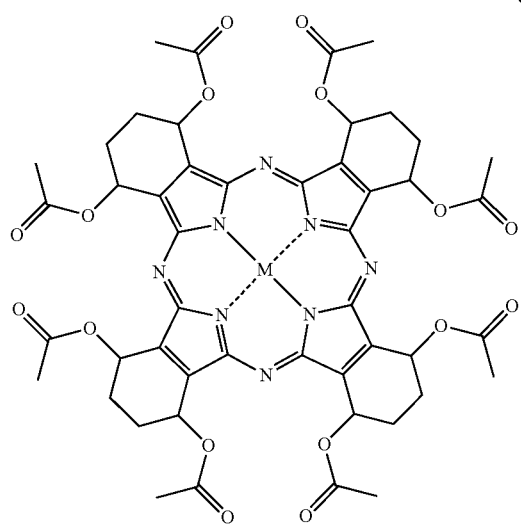
M = H₂: Exemplary compound 24
M = Cu: Exemplary compound 25
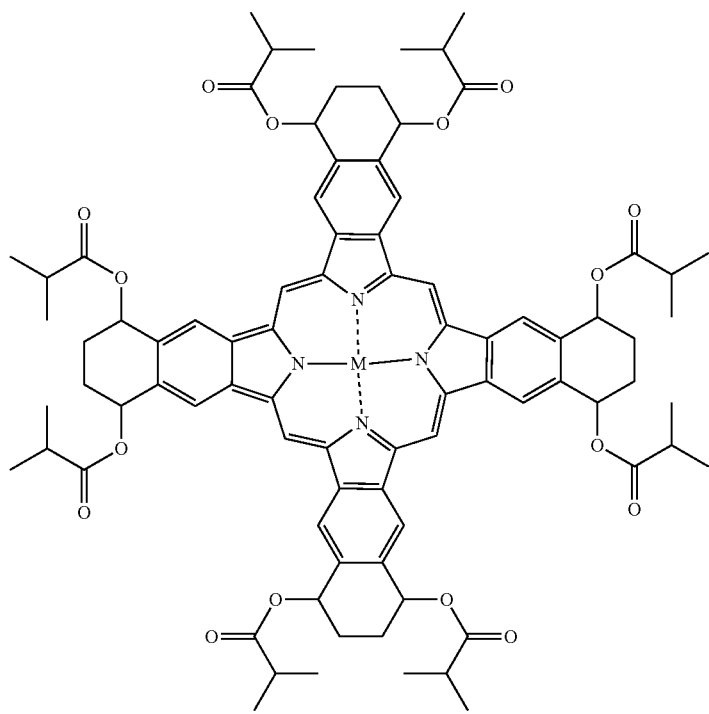
M = H₂: Exemplary compound 26
M = Cu: Exemplary compound 27

Exemplary compound 28
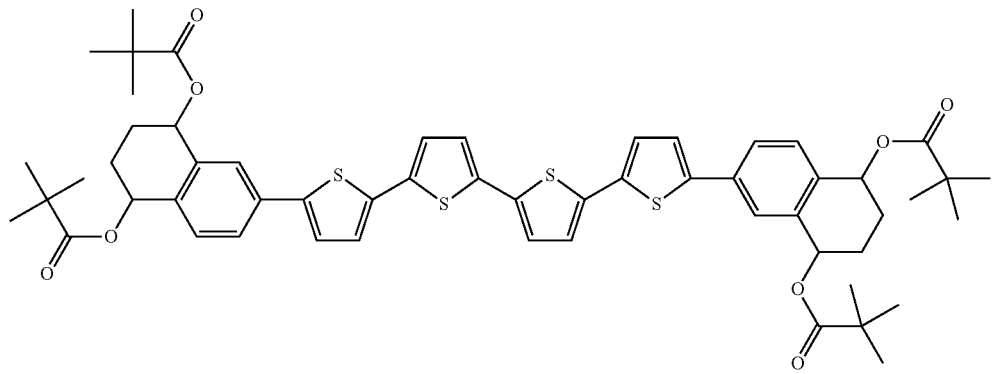
Exemplary compound 29
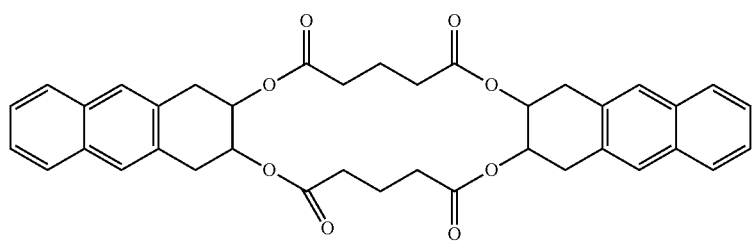
Exemplary compound 30
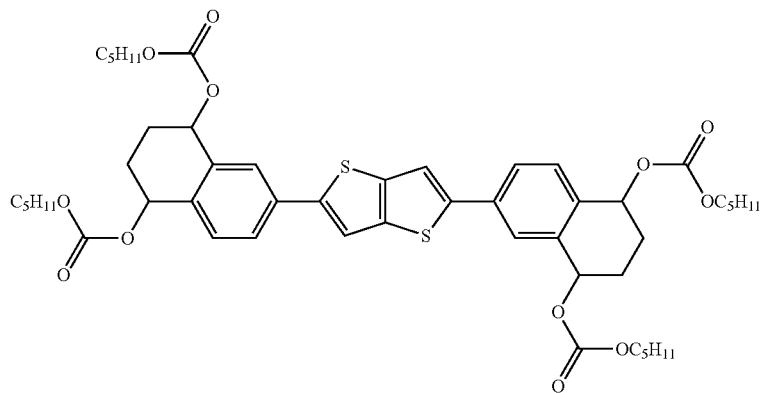
Exemplary compound 31
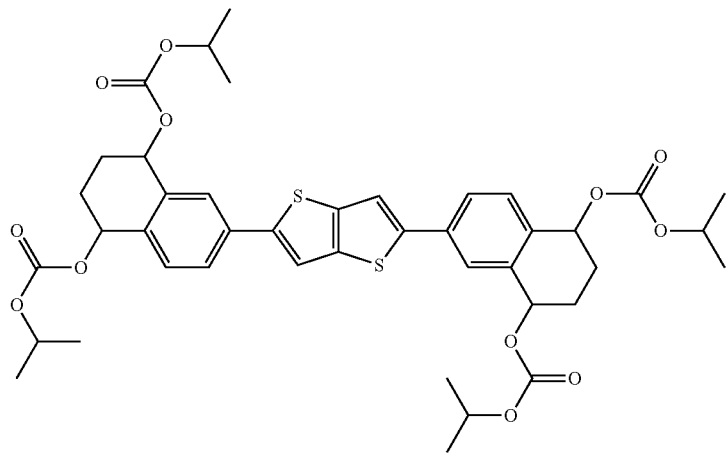

-continued
Exemplary compound 32
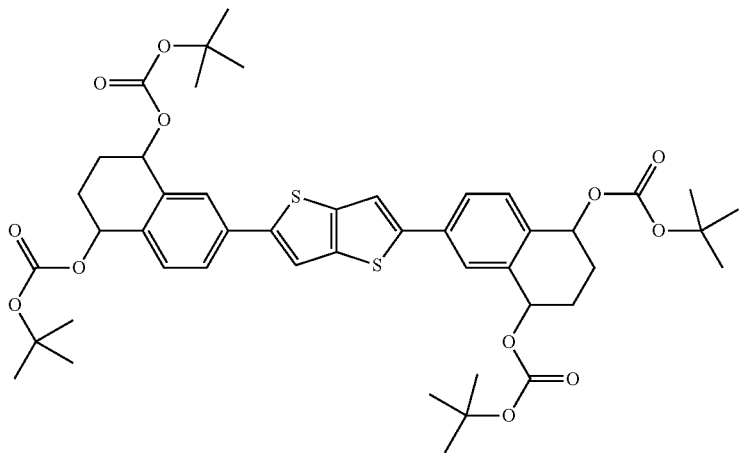
Exemplary compound 33
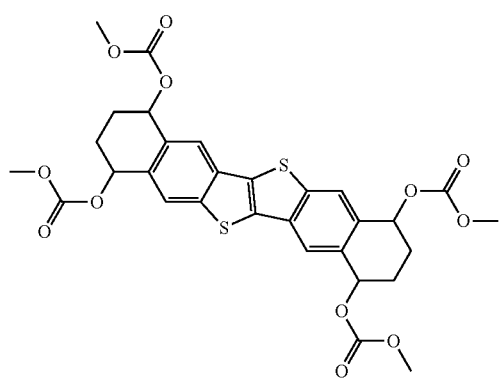
Exemplary compound 34
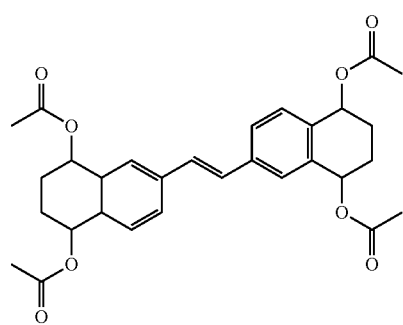
Exemplary compound 35
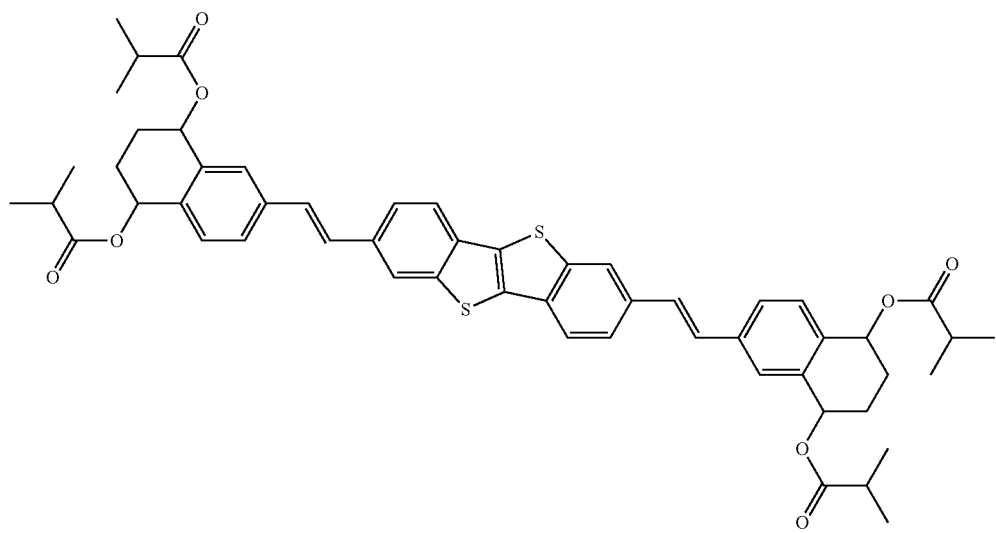

-continued
Exemplary compound 36
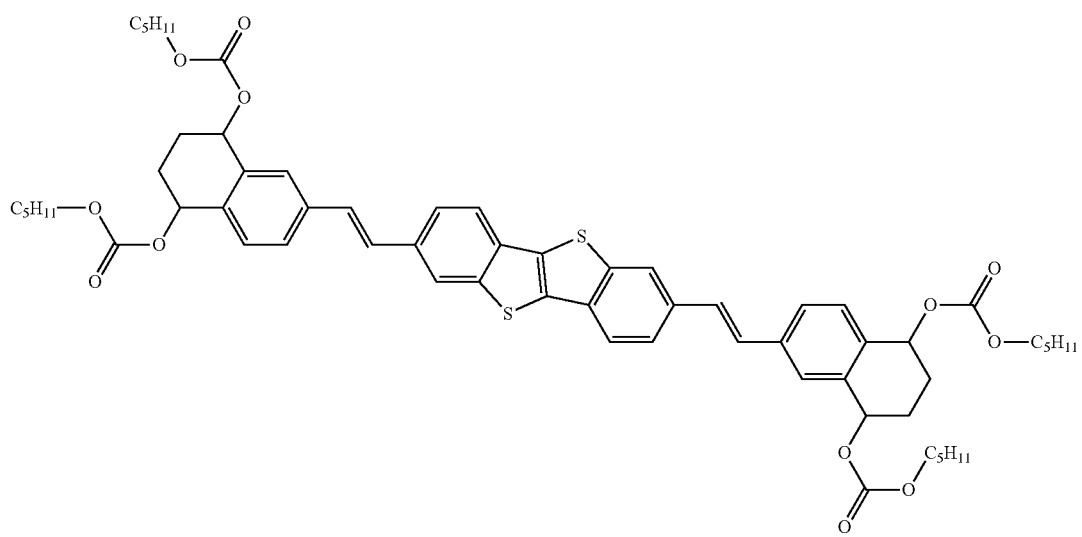
Exemplary compound 37
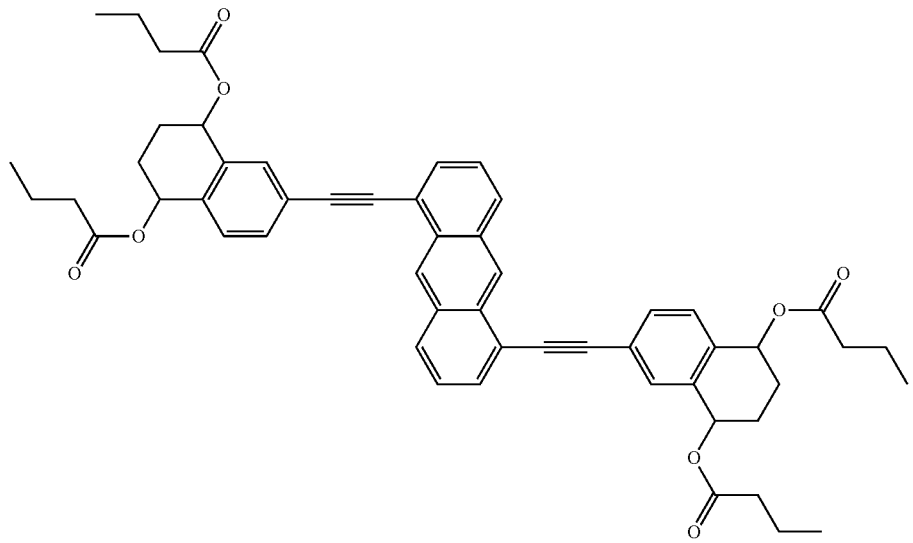
Exemplary compound 38
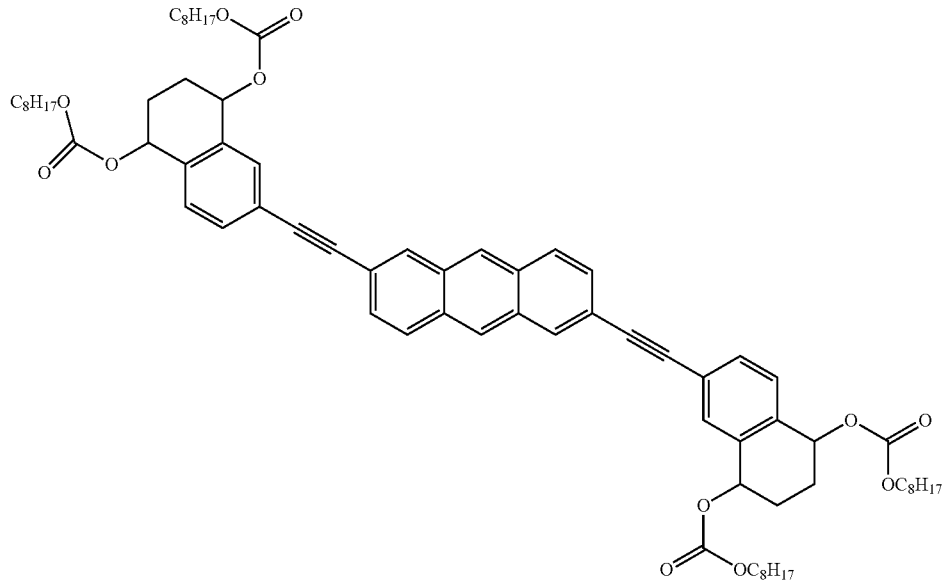

Exemplary compound 39

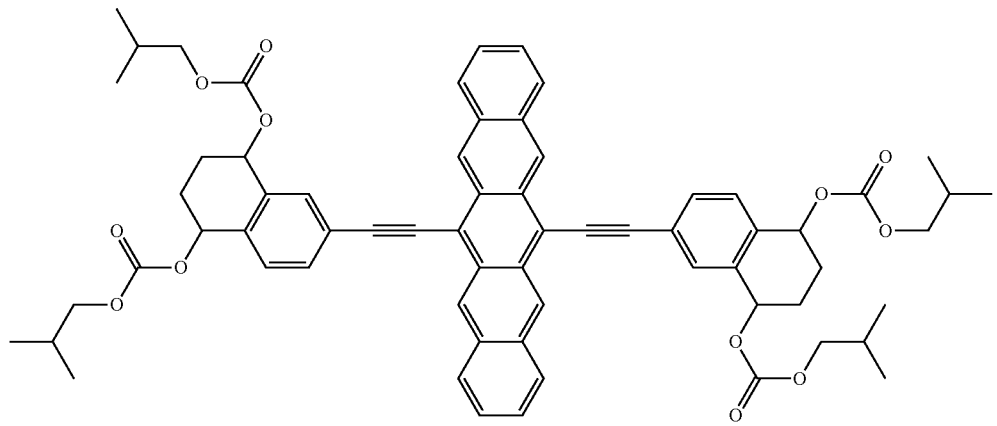

By applying energy to the precursor A-(B)$_m$, the below-described elimination reaction occurs, so that the specific substituents are eliminated, thereby obtaining a π-electron conjugated compound A-(C)m and a film-like product containing the compound.

Next, the compound A-(C)m (hereinafter may be referred to as a "specific compound") produced from the precursor A-(B)$_m$ will be exemplified. However, the π-electron conjugated compound in the present invention should not be construed as being limited thereto.

Specific compound 1

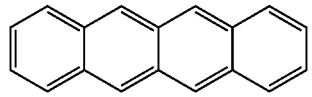

Specific compound 2

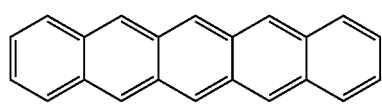

Specific compound 3

Specific compound 4

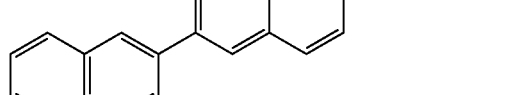

-continued

Specific compound 5

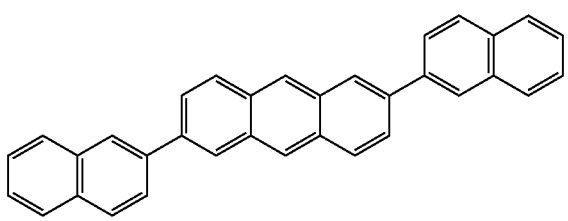

Specific compound 6

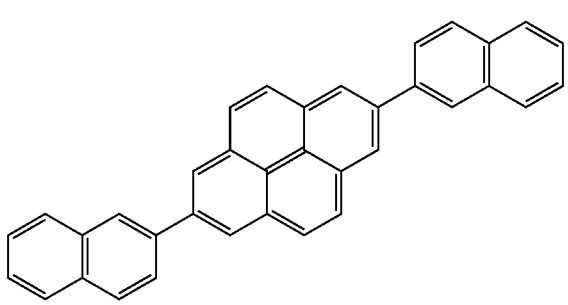

Specific compound 7

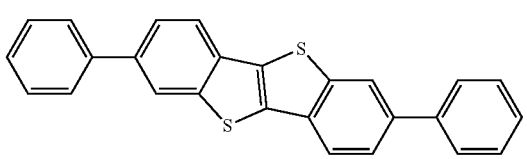

Specific compound 8

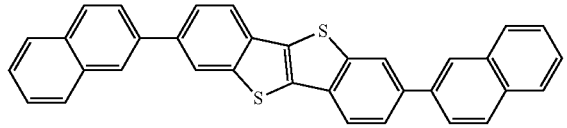

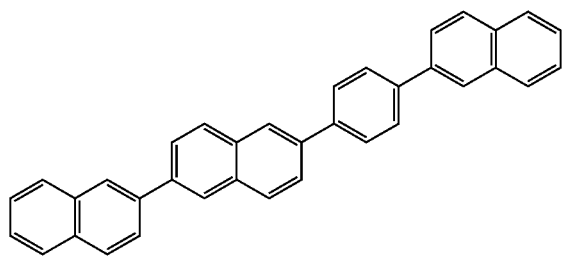

Specific compound 9
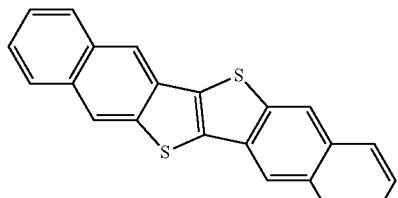
Specific compound 10
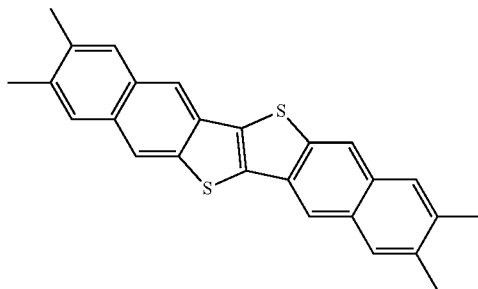
Specific compound 11
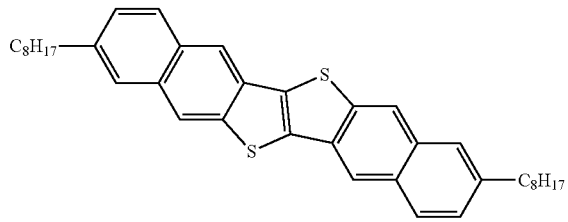
Specific compound 12
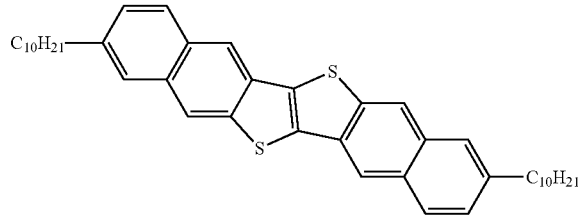
Specific compound 13
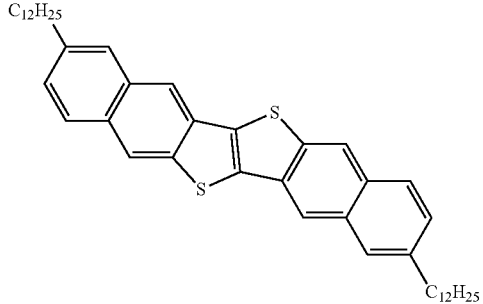
Specific compound 14
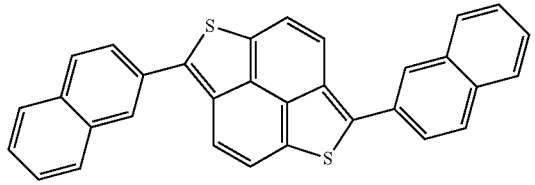
Specific compound 15
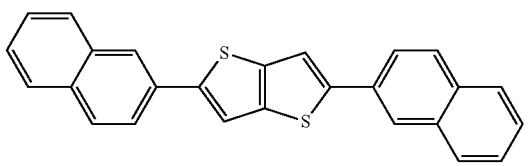
Specific compound 16
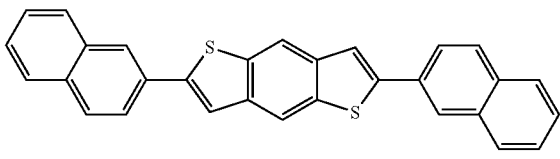
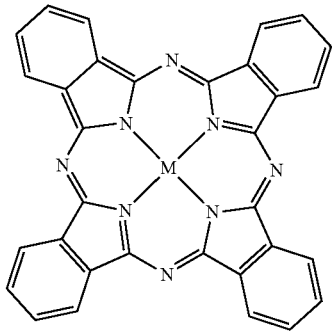
M = H$_2$: Specific compound 17
M = Cu: Specific compound 18
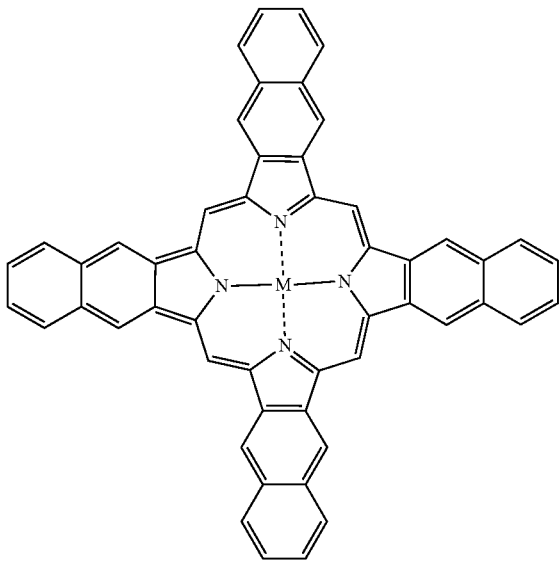
M = H$_2$: Specific compound 19
M = Cu: Specific compound 20
Specific compound 21
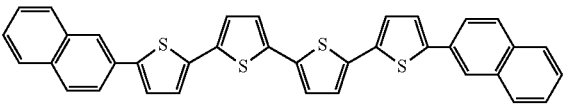

Specific compound 22

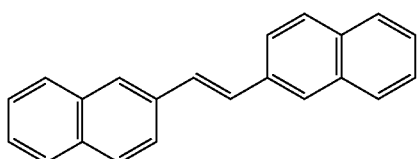

Specific compound 23

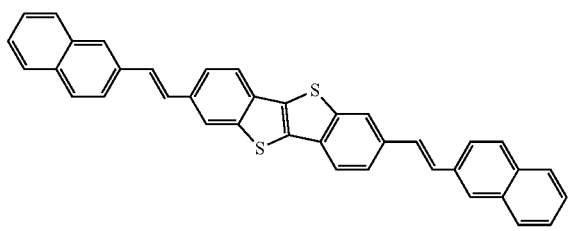

Specific compound 24

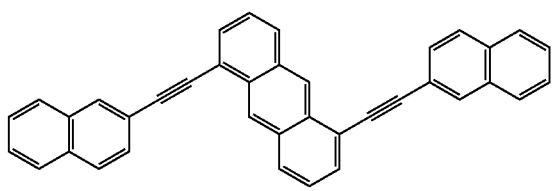

Specific compound 25

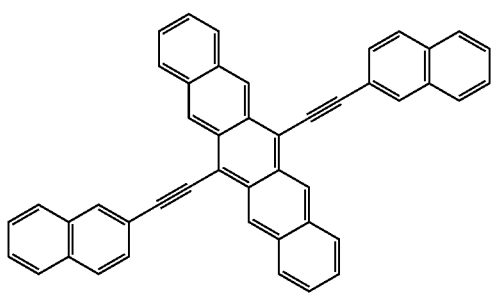

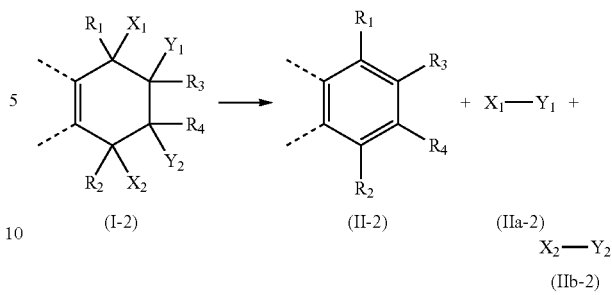

(I-2)  (II-2)  (IIa-2)

$$X_2—Y_2$$

(IIb-2)

There are several stereoisomers of the compound represented by General Formula (I-2) depending on the steric configuration of the substituents. However, each of the stereoisomers is converted to the compound represented by General Formula (II-2), and eliminated components are the same in each case. More preferably, substituents $X_1$ and $Y_1$ or substituents $X_2$ and $Y_2$ are located on the same side of the cyclohexene ring plane (cis-configuration) from the viewpoints of improving the efficiency of the elimination reaction, decreasing the conversion temperature, and increasing the reaction yield.

The substituents $(X_1, X_2)$ and $(Y_1, Y_2)$ eliminated from the precursor represented by General Formula (I-2) are the same as described above in "Method for producing specific compound through elimination reaction of leaving substituent-containing compound."

(Method for Producing π-electron Conjugated Compound Precursor)

The method for forming a halogen group and acyloxy group in the cyclohexene skeleton of the solvent-soluble substituent is the same as described above in "Method for producing Leaving Substituent-Containing Compound."

Also, the method for linking together via a covalent bond the π-electron conjugated substituent A and the solvent-soluble substituent B, which are used in the method for producing the precursor A-(B)m in the present invention, is the same as the method for bonding the solvent-soluble substituent to the other skeleton in the above-described leaving substituent-containing compound.

(Electronic Devices)

The specific compound of the present invention can be used for the electronic devices described above in "(Application of Leaving Substituent-Containing Compound to Device."

That is, the solvent used for preparing a coating liquid containing the precursor A-(B)m is not particularly limited and may be appropriately selected depending on the intended purpose. The solvent preferably has a boiling point of 500° C. or lower since such solvent can be easily removed. However, highly volatile solvents are not necessarily preferred, and the solvent used preferably has a boiling point of 50° C. or higher. Although thorough examination has not yet been conducted, for obtaining a sufficient conductivity, it is thought to be important that the precursors variously change in position for intermolecular contact as well as that the leaving groups in the precursor are simply eliminated. In other words, after the leaving groups (substituents) have been eliminated from the precursor present in the coating film, it is possibly required in the solvent that the resultant compounds be at least partially change in direction or position from a random state for intermolecular contact, rearrangement, aggregation, crystallization, etc.

(Method for Producing π-electron Conjugated Compound Through Elimination Reaction of π-electron Conjugated Compound Precursor)

The method of the present invention for producing the film-like product containing the π-electron conjugated compound has a core step of producing the π-electron conjugated compound through elimination reaction. Thus, the elimination reaction will be described in detail.

In the production method of the present invention, a film containing the compound (precursor) having a cyclohexene ring structure represented by General Formula (I-2) is formed by, for example, coating on a substrate (support) such as a plastic substrate, a metal substrate, a silicon wafer and a glass substrate. Next, eliminated components represented by General Formulas (IIa-2) and (IIb-2) are eliminated from the compound (precursor) having the cyclohexene ring structure contained in the precursor-containing film, so that the compound (precursor) is converted to the compound having a structure represented by General Formula (II-2).

The solvent used may be, for example, those having affinity to a polar carboester group serving as a leaving group contained in the precursor A-(B)m. Specific examples thereof include polar (water-miscible) solvents such as alcohols (e.g., methanol, ethanol and isopropanol), glycols (e.g., ethylene glycol, diethylene glycol and propylene glycol), ethers (e.g., tetrahydrofuran (THF) and dioxane), ketones (e.g., methyl ethyl ketone and methyl isobutyl ketone), phenols (e.g., phenol and cresol), nitrogen-containing organic solvents (e.g., dimethyl formamide (DMF), pyridine, dimethylamine and triethylamine) and CELLOSOLVE (registered trademark) (e.g., methyl cellosolve and ethyl cellosolve). The solvent may also be those having relatively high affinity to the other structure than the leaving groups. Specific examples thereof include hydrocarbons (e.g., toluene, xylene and benzene), halogenated hydrocarbon solvents (e.g., carbon tetrachloride, methylene chloride, 1,2-dichloroethane, 1,1,2-trichloroethane, trichloroethylene, chloroform, monochlorobenzene and dichloroethylidene), esters (e.g., methyl acetate and ethyl acetate) and nitrogen-containing organic solvents (e.g., nitromethane and nitroethane). These solvents may be used alone or in combination.

In use, polar (water-miscible) solvents such as tetrahydrofuran (THF) are particularly preferably combined with water-immiscible solvents such as halogenated hydrocarbons (e.g., toluene, xylene, benzene, methylene chloride, 1,2-dichloroethane, chloroform and carbon tetrachloride) and esters (e.g., ethyl acetate).

The amount of the organic solvent used is not particularly limited and may be appropriately determined depending on the intended purpose. The amount of the organic solvent is preferably 200 parts by mass to 200,000 parts by mass with respect to 1 part by mass of the precursor A-(B)m.

Also, the coating liquid may further contain a resin component and a volatile or self-decomposable acid or base for promoting decomposition of the carboester group in such a small amount that the effects of the present invention cannot be impaired. Further, strongly-acid solvents such as trichloroacetic acid (which decomposes into chloroform and carbon dioxide with heating) and trifluoroacetic acid (volatile) are preferably used since the carboester group (weak Lewis acid) is readily removed in the presence of them. Also, by applying energy to the film containing the precursor of an organic semiconductor, the film can be converted to an organic semiconductor film.

EXAMPLES

Hereinafter, the present invention will be further described with the following Examples, which should not be construed as limiting the scope of the present invention.

The identification of the compounds used in Examples was performed using a NMR spectrometer (JNM-ECX, manufactured by JEOL Ltd., 500 MHz), a mass spectrometer (GCMS-QP2010 Plus, manufactured by SHIMADZU CORPORATION), an elemental analyzer (CHN) (CHN coder MT-2, manufactured by Yanagimoto Mfg. Co., Ltd.), and an elemental analyzer (sulfur) (DX320 manufactured by Dionex Corporation, ion chromatography—anion analysis system). The purity of each compound was obtained by measuring the compound using a mass spectrometer (GCMS-QP2010 Plus, manufactured by SHIMADZU CORPORATION), or LCMS (LCT Premire and Alliance, manufactured by Waters), and calculating the purity thereof from ratios of peak areas.

Synthesis Example 1

Synthesis 1 of Intermediate of Specific Compound
Synthesis of Compound 2

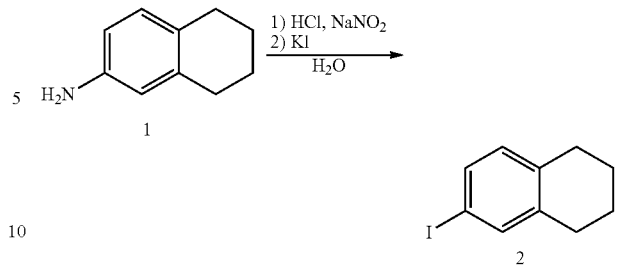

In a 500 mL beaker, 1,2,3,4-tetrahydro-6-iodo naphthalene (compound of the above formula 1, 10 g, 65.3 mmol) and 15% HCl (60 mL) were poured, and while keeping the temperature at 5° C. or lower under cooling with ice, an aqueous sodium nitrite solution (5.41 g, 78.36 mmol in water 23 mL) was gradually added dropwise in the mixed solution.

After the completion of the dropwise addition, the resultant solution was stirred at 5° C. or lower for 1 hour, and an aqueous potassium iodide solution (13.0 g, 78.36 mmol in water 50 mL) was added at one time in the resultant solution. The beaker was taken out of the ice bath, and the solution was stirred for 3 hours, and then heated at 60° C. for 1 hour until no nitrogen was generated.

After the reaction solution had been cooled down to room temperature, the reaction solution was extracted with diethyl ether 3 times. The organic layer was washed with 5% aqueous thiosodium sulfate solution (100 mL) 3 times, and further washed with saturated brine (100 mL) 2 times. Moreover, the organic layer was dried with sodium sulfate, and the filtrate was condensed, to thereby obtain red oil.

The red oil was purified by silica gel column chromatography using hexane as a solvent, to thereby obtain Compound 2 as colorless oil. The amount of Compound 2 was 12.0 g, and the yield was 71.2%. The analysis result of the Compound 2 is as follows.

$^1$H NMR (500 MHz, CDCl$_3$, TMS, δ): 1.73-1.81 (m, 4H), 2.70 (quint, 4H, J=4.85 Hz), 6.80 (d, 1H, J=8.0 Hz), 7.38 (dd, 1H, J$_1$=8.0 Hz J$_2$=1.75 Hz), 7.41 (s, 1H)

Mass spectrometry: GC-MS m/z=258 (M+)

Synthesis of Compound 3

A desired compound was synthesized by using the method described in J. Org. Chem. 1999, 64, 9365-9373.

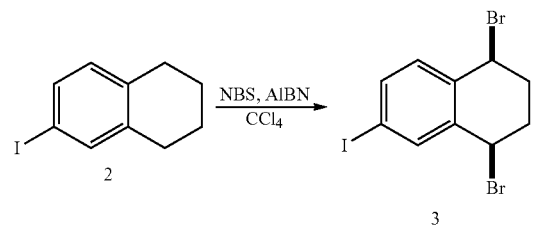

A 100 mL-round bottom flask was charged with Compound 2 (3.1 g, 12 mmol), azobisisobutyronitrile (59 mg, 0.36 mmol), carbon tetrachloride (50 mL), and N-bromosuccinimide (4.7 g, 26.4 mmol), and purged with argon gas, followed by gently heating to 80° C., stirring for 1 hour at the same temperature (80° C.), and then cooling down to room temperature. The precipitation was filtered, and the filtrate was condensed under reduced pressure, to thereby obtain Compound 3 as a pale yellow solid. The amount of Compound 3 was 4.99 g and the yield was 100%.

The compound was not further purified, and used for next reaction.

The analysis result of the Compound 3 is as follows.

$^1$H NMR (500 MHz, CDCl$_3$, TMS, δ): 2.31-2.41 (m, 2H), 2.70-2.79 (m, 2H), 5.65 (t, 2H, J=2.0 Hz), 7.24-7.28 (m, 2H), 7.31-7.34 (m, 2H)

Mass spectrometry: GC-MS m/z=413 (M+)

Synthesis of Compound 4

Similar to Compound 3, 1,4-dibromo-1,2,3,4-tetrahydronaphthalene was synthesized by the method described in J. Org. Chem. 1999, 64, 9365-9373, and used as a material.

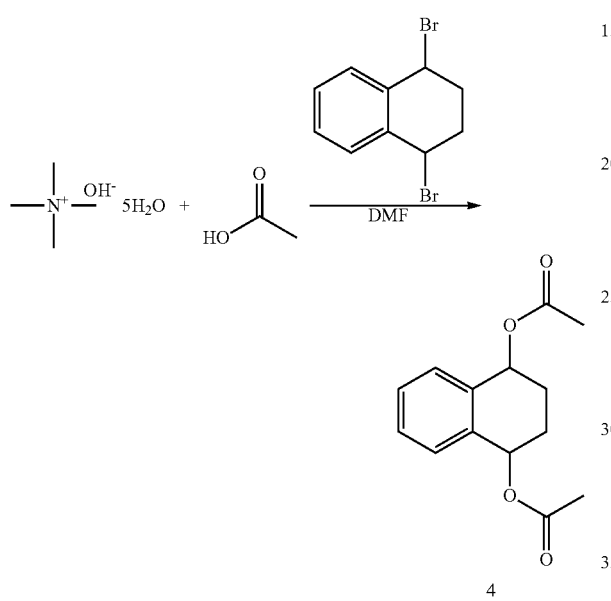

A 100 mL-round bottom flask was charged with tetramethylammonium hydroxide pentahydrate (3.62 g, 20 mmol), acetic acid (1.21 g, 20 mmol), and dimethylformamide (hereinafter referred to as DMF) (30 mL), and purged with argon gas, followed by stirring at room temperature for 2.5 hours. In the flask, 1,4-dibromo-1,2,3,4-tetrahydronaphthalene (2.90 g, 10 mmol) was added, and stirred at room temperature for 16 hours. The reaction solution was diluted with 100 mL of ethyl acetate, and 200 mL of pure water was added to the diluted solution, so as to separate the organic layer. The aqueous layer was extracted with 30 mL of ethyl acetate 4 times, and the combined organic layer was washed with saturated sodium bicarbonate solution, followed by washing with saturated brine, and drying with magnesium sulfate. The filtrate was condensed to thereby obtain a pale brown solid. The solid was washed with hexane, to thereby obtain Compound 4 as a colorless solid. The amount of Compound 4 was 1.50 g and the yield was 60.6%. Also, Compound 4 was a mixture of racemic form and meso form in a ratio of 5:6.

Compound 4 was recrystallized from hexane, so as to separate the racemic form from the meso form.

The analysis result of the Compound 4 is as follows.

Racemic form: $^1$H NMR (500 MHz, CDCl$_3$, TMS, δ): 1.96-1.99 (m, 2H), 2.07 (s, 6H), 2.27-2.30 (m, 2H), 6.05 (t, 2H, J=2.3 Hz), 7.34 (br, 4H)

Meso form: $^1$H NMR (500 MHz, CDCl$_3$, TMS, δ): 2.09-2.12 (m, 4H), 2.13 (s, 6H), 5.96-5.98 (m, 2H), 7.32 (br, 4H)

Mass spectrometry: GC-MS m/z=248 (M+)

Synthesis of Compound 5

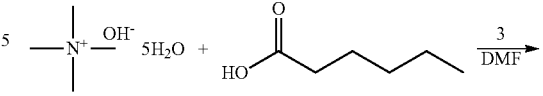

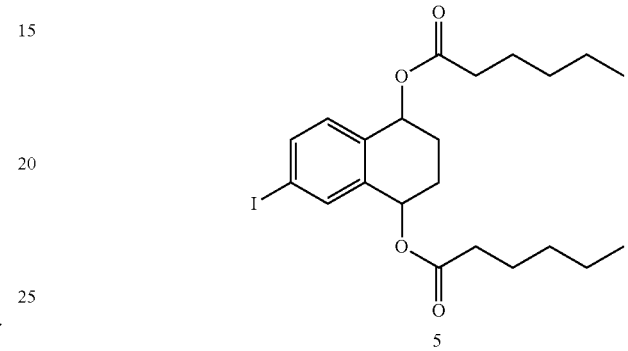

A 100 mL-round bottom flask was charged with tetramethylammonium hydroxide pentahydrate (3.62 g, 20 mmol), caproic acid (2.51 mL, 20 mmol) and DMF (30 mL), and purged with argon gas, followed by stirring at room temperature for 2.5 hours. In the flask, Compound 3 (4.16 g, 10 mmol) was added, and stirred at room temperature for 16 hours. The reaction solution was diluted with 100 mL of ethyl acetate, and 200 mL of pure water was added to the diluted solution, so as to separate the organic layer. The aqueous layer was extracted with 30 mL of ethyl acetate 4 times, and the combined organic layer was washed with saturated sodium bicarbonate solution, followed by washing with saturated brine, and drying with magnesium sulfate. The filtrate was condensed to thereby obtain orange oil. The orange oil was purified by silica gel column chromatography (solvent: toluene→ethyl acetate/toluene (5/95, v/v)), to thereby obtain Compound 5 as colorless oil. The amount of Compound 5 was 2.44 g, and the yield was 50.2%.

The analysis result of the Compound 5 is as follows.

$^1$H NMR (500 MHz, CDCl$_3$, TMS, δ): 0.87-0.90 (m, 6H), 1.24-1.34 (m, 8H), 1.60-1.67 (m, 4H), 1.90-1.94 (m, 2H), 2.23-2.34 (m, 6H), 5.98 (d, 2H, J=3.5 Hz), 7.06 (d, 2H, J=8.0 Hz), 7.63-7.66 (m, 2H)

Mass spectrometry: GC-MS m/z=486 (M+)

From the above analysis result, it was confirmed that a structure of the synthesized product did not contradict that of Compound 5.

Synthesis of Compound 6

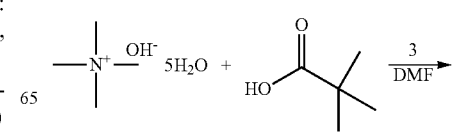

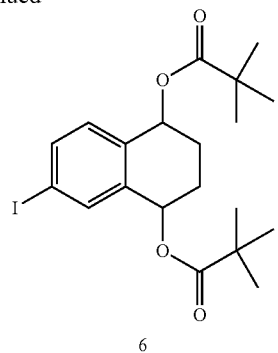

6

A 100 mL-round bottom flask was charged with tetramethylammonium hydroxide pentahydrate (3.62 g, 20 mmol), pivalic acid (2.04 g, 20 mmol) and DMF (30 mL), purged with argon gas, followed by stirring at room temperature for 2.5 hours. In the flask, Compound 3 (4.16 g, 10 mmol) was added, and stirred at room temperature for 16 hours. The reaction solution was diluted with 100 mL of ethyl acetate, and 200 mL of pure water was added to the diluted solution, so as to separate the organic layer. The aqueous layer was extracted with 30 mL of ethyl acetate 4 times, and the combined organic layer was washed with saturated sodium bicarbonate solution, followed by washing with saturated brine, and drying with magnesium sulfate. The filtrate was condensed to thereby obtain a pale orange solid. The pale orange solid was recrystallized from ethanol repeatedly twice, so as to obtain Compound 6 as pale yellow crystals. The amount of Compound 6 was 1.93 g, and the yield was 42.0%.

The analysis result of Compound 6 is as follows.

$^1$H NMR (500 MHz, CDCl$_3$, TMS, δ): 1.18 (s, 18H), 1.20 (s, 18H), 1.87-1.92 (m, 4H), 2.21-2.24 (m, 4H), 5.94 (d, 4H, J=2.3 Hz), 7.02 (d, 2H, J=8.0 Hz), 7.62-7.63 (m, 2H), 7.64-7.65 (m, 2H)

Mass spectrometry: GC-MS m/z=458 (M+)

Melting point: 114.0° C. to 115.5° C.

From the above analysis result, it was confirmed that a structure of the synthesized product did not contradict that of Compound 6.

Synthesis of Compound 7

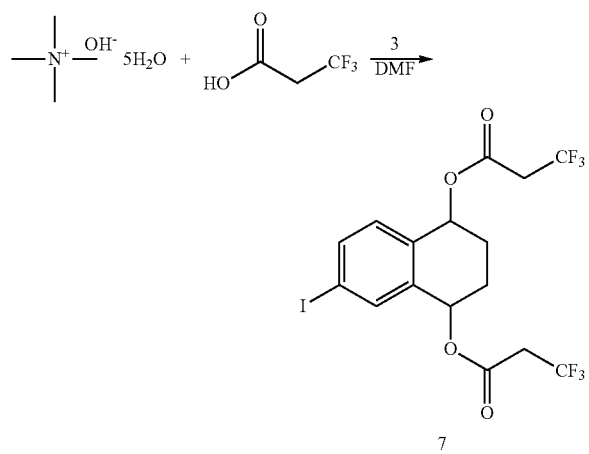

7

A 100 mL-round bottom flask was charged with tetramethylammonium hydroxide pentahydrate (3.62 g, 20 mmol), 3,3,3-trifluoropropanoic acid (2.56 g, 20 mmol) and DMF (30 mL), and purged with argon gas, followed by stirring at room temperature for 2.5 hours. In the flask, Compound 3 (4.16 g, 10 mmol) was added, and stirred at room temperature for 48 hours.

The reaction solution was diluted with 100 mL of ethyl acetate, and 200 mL of pure water was added to the diluted solution, so as to separate the organic layer. The aqueous layer was extracted with 30 mL of ethyl acetate 4 times, and the combined organic layer was washed with saturated sodium bicarbonate solution, followed by washing with saturated brine, and drying with magnesium sulfate. The filtrate was condensed to thereby obtain a brown liquid. The brown liquid was purified by silica gel column chromatography (solvent: ethyl acetate/hexane (1/2, v/v) and 2% triethylamine), to thereby obtain light yellow oil having an amount 2.44 g.

The light yellow oil was purified by Recycling Preparative HPLC (LC-9104, manufactured by Japan Analytical Industry Co., Ltd.), to thereby obtain Compound 7 as colorless oil. The amount of Compound 7 was 1.2 g, and the yield was 25%.

The analysis result of the Compound 7 is as follows.

$^1$H NMR (500 MHz, CDCl$_3$, TMS, δ): 1.99-2.31 (m, 4H, H2, H3), 3.14-3.30 (m, 4H, —CH2CF3), 5.96-6.08 (m, 2H, H1, H4), 7.05-7.10 (m, 1H, ArH), 7.66-7.71 (m, 2H, ArH)

Mass spectrometry: GC-MS m/z=510 (M+)

From the above analysis result, it was confirmed that a structure of the synthesized product did not contradict that of Compound 7.

Synthesis Example 2

Synthesis 2 of Intermediate of Specific Compound
Synthesis of Compound 8

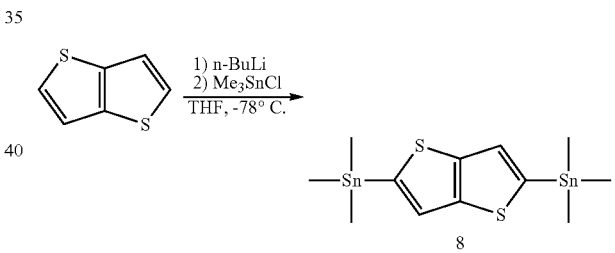

8

A 200 mL-round bottom flask, which had been sufficiently dried, was charged with thieno[3,2-b]thiophene (2.81 g, 20.0 mmol), and purged with argon. The flask was further charged with anhydrous tetrahydrofuran, (hereinafter referred to as THF) (50 mL), and cooled down to −78° C. by using an acetone-dry ice bath. Into the flask, n-butyllithium (2.2 eq, 28.1 mL (1.6 M hexane solution), 44 mmol) was added dropwise for 15 minutes, and the temperature of the reaction system was increased to room temperature, followed by stirring at room temperature for 16 hours. The reaction system was cooled down to −78° C. again, and trimethyltin chloride (2.5 eq, 50 mL (1.0 M hexane solution), 50 mmol) was added at one time to the reaction system. The temperature of the reaction system was increased to room temperature, followed by stirring for 24 hours.

Water (80 mL) was added to the reaction system, followed by quenching. Then ethyl acetate was further added to the reaction system, so as to separate the organic layer. The organic layer was washed with a saturated aqueous potassium fluoride solution, and washed with saturated brine, and dried with sodium sulfate. After filtration, the filtrate was condensed to thereby obtain a brown solid. The brown solid was recrystallized from acetonitrile consecutively three times, to thereby obtain Compound 8 as colorless crystals. The amount of Compound 8 was 5.0 g, and the yield was 54.1%.

The analysis result of the compound 8 is as follows.

$^1$H NMR (500 MHz, CDCl$_3$, TMS, δ): 0.38 (s, 18H), 7.23 (s, 2H)

Mass spectrometry: GC-MS m/z=466 (M+)

From the above analysis result, it was confirmed that a structure of the synthesized product did not contradict that of Compound 8.

Synthesis of Compound 9

Benzo[1,2-b:4,5-b']dithiophene was synthesized by the method described in J. Org. Chem., 2005, 70 (25), pp. 10569-10571 and Org. Lett. 2009, 11 (11), pp. 2473-2475 in the same manner as described in Japanese Patent Application Laid-Open (JP-A) No. 2009-275032 and used as a material.

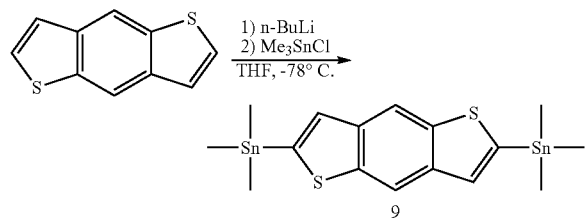

A 200 mL-round bottom flask, which had been sufficiently dried, was charged with benzo[1,2-b:4,5-b]dithiophene (3.81 g, 20.0 mmol), and purged with argon. The flask was further charged with anhydrous THF (50 mL), and cooled down to −78° C. by using an acetone-dry ice bath. Into the flask, n-butyllithium (2.2 eq, 28.1 mL (1.6 M hexane solution), 44 mmol) was added dropwise for 15 minutes, and the temperature of the reaction system was increased to room temperature, followed by stirring at room temperature for 16 hours. The reaction system was cooled down to −78° C. again, and trimethyltin chloride (2.5 eq, 50 mL (1.0 M hexane solution), 50 mmol) was added at one time to the reaction system. The temperature of the reaction system was increased to room temperature and followed by stirring for 24 hours.

Water (80 mL) was added to the reaction system, followed by quenching. Then ethyl acetate was further added to the reaction system, so as to separate the organic layer. The organic layer was washed with a saturated aqueous potassium fluoride solution, and washed with saturated brine, and dried with sodium sulfate. After filtration, the filtrate was condensed to thereby obtain a brown solid. The brown solid was recrystallized from acetonitrile consecutively three times, to thereby obtain Compound 9 as pale yellow crystals. The amount of Compound 9 was 7.48 g, and the yield was 72.5%.

The analysis result of Compound 9 is as follows.

$^1$H NMR (500 MHz, CDCl$_3$, TMS, δ): 0.44 (s, 18H), 7.41 (s, 2H), 8.27 (s, 2H)

Mass spectrometry: GC-MS m/z=518 (M+)

From the above analysis result, it was confirmed that a structure of the synthesized product did not contradict that of Compound 9.

Synthesis of Compound 10

2,7-Diiodo[1]benzothieno[3,2-b][1]benzothiophene was synthesized with reference to Zh. Org. Khim., 16, 2, 383 (1980) and J. Am. Chem. Soc. 128, 12604 (2006), and used as a material.

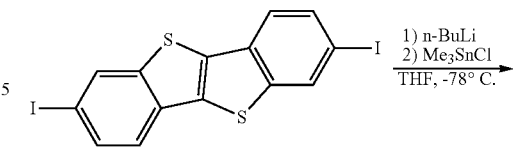

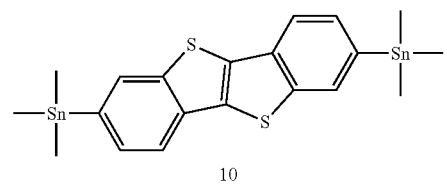

A 300 mL-round bottom flask, which had been sufficiently dried, was charged with 2,7-diiodo[1]benzothieno[3,2-b][1]benzothiophene (4.92 g, 10.0 mmol), and purged with argon. The flask was further charged with anhydrous THF (150 mL), and cooled down to −78° C. by using an acetone-dry ice bath. Into the flask, n-butyllithium (2.2 eq, 14.1 mL (1.6 M hexane solution), 22 mmol) was added dropwise for 15 minutes, and the temperature of the reaction system was increased to room temperature, followed by stirring at room temperature for 16 hours. The reaction system was cooled down to −78° C. again, and trimethyltin chloride (2.5 eq, 25 mL (1.0 M hexane solution), 25 mmol) was added at one time to the reaction system. The temperature of the system was increased to room temperature and followed by stirring for 24 hours.

Water (80 mL) was added to the reaction system, followed by quenching. Then chloroform was further added to the reaction system, so as to separate the organic layer. The organic layer was washed with a saturated aqueous potassium fluoride solution, and washed with saturated brine, and dried with sodium sulfate. After filtration, the filtrate was condensed to thereby obtain a brown solid. The brown solid was recrystallized from toluene, and further recrystallized from acetonitrile, to thereby obtain Compound 10 as pale brown crystals. The amount of Compound 10 was 3.40 g, and the yield was 60.0%.

The analysis result of Compound 10 is as follows.

$^1$H NMR (500 MHz, CDCl$_3$, TMS, δ): 0.37 (s, 18H), 7.55 (d, 2H, J=8.6 Hz), 7.87 (d, 2H, J=7.5 Hz), 8.04 (s, 2H)

Mass spectrometry: GC-MS m/z=566 (M+)

From the above analysis result, it was confirmed that a structure of the synthesized product did not contradict that of Compound 10.

Synthesis Example 3

Synthesis of Precursor Molecule

Synthesis of Compound 11

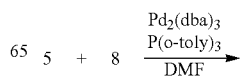

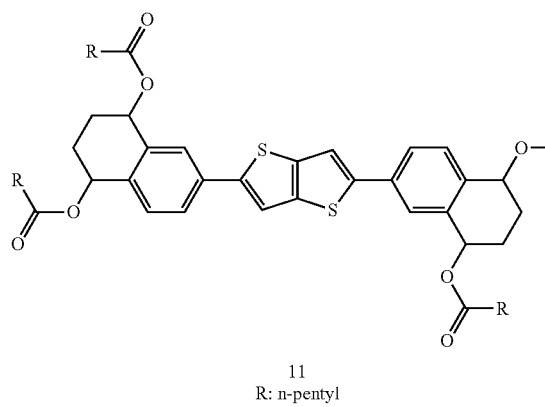

11
R: n-pentyl

A 100 mL-round bottom flask was charged with Compound 5 (973 mg, 2.0 mmol), Compound 8 (466 mg, 1 mmol, and DMF (10 mL), bubbled with argon gas for 30 minutes, and then further charged with tris(dibenzylideneacetone)dipalladium (0) (18.3 mg, 0.02 mmol) and tri(ortho-tolyl)phosphine (24.4 mg, 0.08 mmol), followed by stirring for 20 hours at room temperature in an argon atmosphere. The reaction solution was diluted with chloroform. The diluted solution was filtered through CELITE, and the insoluble matter was removed. Then, water was added to the filtrate so as to separate the organic layer. The aqueous layer was extracted with chloroform three times, and the combined organic layer was washed with saturated aqueous potassium fluoride solution, followed by washing with saturated brine, and drying with magnesium sulfate. The filtrate was condensed to thereby obtain a red liquid. The red liquid was purified by column chromatography (fixed bed: (neutral silica gel, manufactured by KANTO CHEMICAL CO., INC.) and 10% by mass potassium fluoride, solvent: hexane/ethyl acetate, 9/1→8/2, v/v), to thereby obtain a yellow solid. The yellow solid was recrystallized from hexane/ethanol, to thereby obtain Compound 11 as a yellow solid. The amount of Compound 11 was 680 mg, and the yield was 79.3%.

The analysis result of Compound 11 is as follows.

$^1$H NMR (500 MHz, CDCl$_3$, TMS, δ): 0.87-0.89 (m, 12H), 1.28-1.33 (m, 16H), 1.61-1.69 (m, 8H), 1.96-2.01 (m, 4H), 2.28-2.36 (m, 12H), 6.08 (d, 4H, J=12.1 Hz), 7.37 (d, 2H, J=8.6 Hz), 7.48 (s, 2H), 7.57-7.59 (m, 4H)

Elemental analysis ($C_{50}H_{64}O_8S_2$)

Synthesis of Compound 12

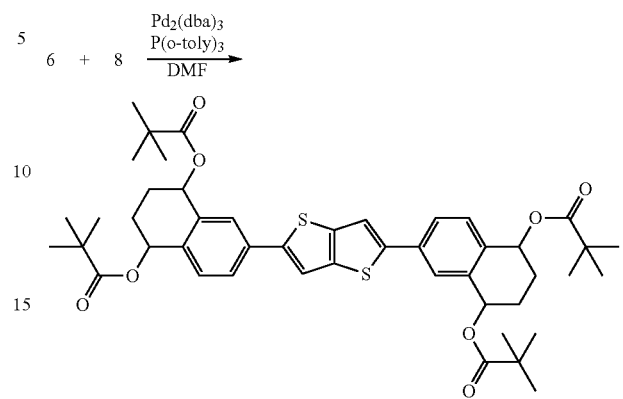

12

A 100 mL-round bottom flask was charged with Compound 6 (2.0 mmol, 917 mg), Compound 8 (466 mg, 1 mmol) and DMF (10 mL), bubbled with argon gas for 30 minutes, and then further charged with tris(dibenzylideneacetone)dipalladium (0) (18.3 mg, 0.02 mmol) and tri(ortho-tolyl)phosphine (24.4 mg, 0.08 mmol), followed by stirring at room temperature in an argon atmosphere for 24 hours, and further stirring at 50° C. for 3 hours. The reaction solution was diluted with toluene. The diluted solution was filtered through CELITE, and the insoluble matter was removed. Then, water was added to the filtrate so as to separate the organic layer. The aqueous layer was extracted with toluene. The combined organic layer was washed with saturated aqueous potassium fluoride solution, followed by washing with saturated brine, and drying with magnesium sulfate. The filtrate was condensed to obtain a solid, and the obtained solid was washed with hexane, to thereby obtain Compound 12 as a yellow solid. The amount of Compound 12 was 320 mg, and the yield was 40.0%.

The analysis result of Compound 12 is as follows.

$^1$H NMR (500 MHz, CDCl$_3$, TMS, δ): 1.21 (s, 18H), 1.24 (s, 18H), 1.90-1.96 (m, 4H), 2.30 (dt, 4H, J$_1$=9.2 Hz, J$_2$=2.3 Hz), 6.03 (d, 4H, J=13.2 Hz), 7.32 (d, 2H, J=8.0 Hz 7.46 (s, 2H), 7.53 (d, 2H, J=1.7 Hz), 7.58 (dd, 2H, J$_1$=8.0 Hz, J$_2$=2.3 Hz)

Elemental analysis ($C_{46}H_{56}O_8S_2$)

|   | Found | Theoretical |
|---|-------|-------------|
| C | 69.92 | 70.06 |
| H | 7.67  | 7.53  |
| O | 14.85 | 14.93 |
| S | 7.44  | 7.48  |

Melting point: 113.7° C. to 114.7° C.

From the above analysis result, it was confirmed that a structure of the synthesized product did not contradict that of Compound 11.

|   | Found | Theoretical |
|---|-------|-------------|
| C | 68.87 | 68.97 |
| H | 6.95  | 7.05  |
| O | 16.08 | 15.98 |
| S | 8.10  | 8.01  |

Decomposition temperature: 275.2° C.

From the above analysis result, it was confirmed that a structure of the synthesized product did not contradict that of Compound 12.

Synthesis of Compound 13

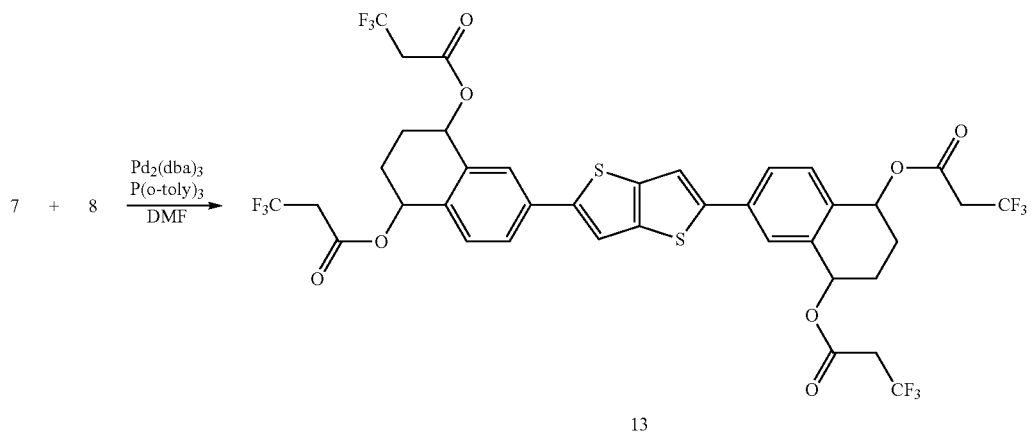

A 100 mL-round bottom flask was charged with Compound 7 (1,020 mg, 2.0 mmol), Compound 8 (466 mg, 1 mmol), and DMF (10 mL), bubbled with argon gas for 30 minutes, and then further charged with tris(dibenzylideneacetone)dipalladium (0) (18.3 mg, 0.02 mmol), and tri(orthotolyl)phosphine (24.4 mg, 0.08 mmol), and followed by stirring at room temperature in an argon atmosphere for 16 hours, further stirring at 80° C. for 8 hours. The reaction solution was diluted with ethyl acetate. The diluted solution was filtered through CELITE, and the insoluble matter was removed. Then, water was added to the filtrate, so as to separate the organic layer. The aqueous layer was extracted with ethyl acetate. The combined organic layer was washed with a saturated aqueous potassium fluoride solution, followed by washing with saturated brine, and drying with magnesium sulfate. The filtrate was condensed to thereby obtain a yellow solid. The yellow solid was purified by column chromatography (fixed bed: (neutral silica gel, manufactured by KANTO CHEMICAL CO., INC., and 10% by mass potassium fluoride, solvent: hexane/ethyl acetate (2/1, v/v) and 2% triethylamine), to thereby obtain a yellow solid.

The yellow solid was purified by Recycling Preparative HPLC (LC-9104, manufactured by Japan Analytical Industry Co., Ltd., solvent: THF), to thereby obtain Compound 13 as light yellow crystals. The amount of Compound 13 was 200 mg, and the yield was 22.1%. The analysis result of Compound 13 is as follows.

$^1$H NMR (500 MHz, CDCl$_3$, TMS, δ): 2.06-2.35 (m, 8H, H2, H3 of Tetralin), 3.16-3.33 (m, 8H, —CH2CF3), 6.07-6.18 (m, 4H, H1, H4 of Tetralin), 7.36-7.41 (m, 2H, ArH), 7.50 (d, 2H, J=6.9 Hz, ArH), 7.57-7.64 (m, 4H, ArH)

Elemental analysis ($C_{38}H_{28}F_{12}O_8S_2$)

|   | Found | Theoretical |
|---|-------|-------------|
| C | 50.65 | 50.45 |
| H | 3.02  | 3.12  |
| O | 14.00 | 14.15 |
| S | 7.19  | 7.09  |

Decomposition temperature: 197.5° C.

From the above analysis result, it was confirmed that a structure of the synthesized product did not contradict that of Compound 13.

Synthesis of Compound 14

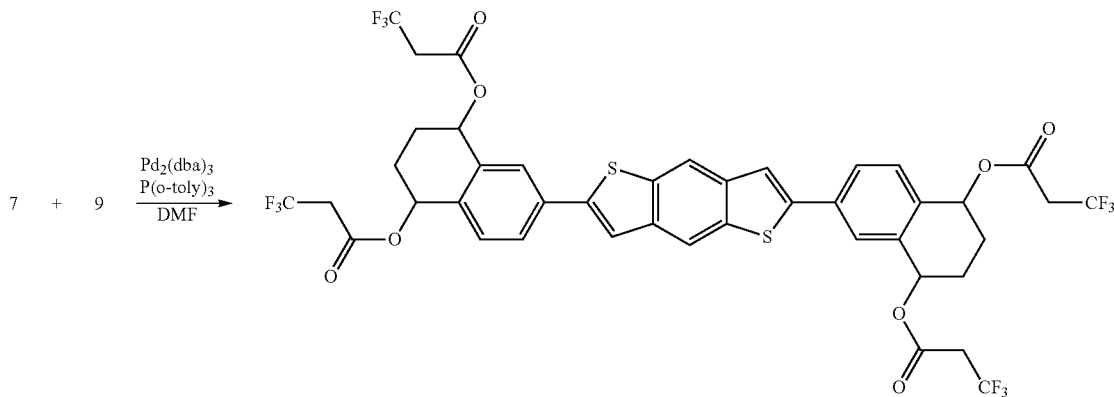

A 100 mL-round bottom flask was charged with Compound 7 (1,887 mg, 3.7 mmol), Compound 9 (929 mg, 1.8 mmol), and DMF (25 mL), bubbled with argon gas for 30 minutes, and then further charged with tris(dibenzylideneacetone)dipalladium (0) (32.9 mg, 0.036 mmol) and tri(orthotolyl)phosphine (43.9 mg, 0.144 mmol), followed by stirring for 4 hours at 80° C. in an argon atmosphere. The reaction solution was diluted with chloroform. The diluted solution was filtered through CELITE, and the insoluble matter was removed. Then, water was added to the filtrate so as to separate the organic layer. The aqueous layer was extracted with chloroform. The combined organic layer was washed with saturated aqueous potassium fluoride solution, followed by washing with saturated brine, and drying with magnesium sulfate. The filtrate was condensed to obtain a yellow solid.

The yellow solid was purified by Recycling Preparative HPLC (LC-9104, manufactured by Japan Analytical Industry Co., Ltd., solvent: THF), to thereby obtain Compound 14 as light yellow crystals. The amount of Compound 14 was 340 mg, and the yield was 20.0%.

The analysis result of Compound 14 is as follows.

$^1$H NMR (500 MHz, CDCl$_3$, TMS, δ): 2.08-2.37 (m, 8H, H2, H3 of Tetralin), 3.20-3.3.34 (m, 8H, —CH2CF3), 6.09-6.6.21 (m, 4H, H1, H4 of Tetralin), 7.40-7.47 (m, 2H, ArH), 7.60 (d, 2H, J=7.5 Hz, ArH), 7.68-7.75 (m, 4H, ArH), 8.22 (s, 2H)

Elemental analysis ($C_{42}H_{30}F_{12}O_8S_2$)

|   | Found | Theoretical |
|---|-------|-------------|
| C | 52.74 | 52.83 |
| H | 3.28  | 3.17  |
| O | 13.70 | 13.41 |
| S | 6.52  | 6.72  |

Decomposition temperature: 231° C.

From the above analysis result, it was confirmed that a structure of the synthesized product did not contradict that of Compound 14.

Synthesis of Compound 15

(ortho-tolyl)phosphine (43.9 mg, 0.144 mmol), followed by stirring for 12 hours at 80° C. in an argon atmosphere. The reaction solution was diluted with chloroform. The diluted solution was filtered through CELITE, and the insoluble matter was removed. Then, water was added to the filtrate so as to separate the organic layer. The aqueous layer was extracted with chloroform. The combined organic layer was washed with saturated aqueous potassium fluoride solution, followed by washing with saturated brine, and drying with magnesium sulfate. The filtrate was condensed to obtain a yellow solid. The yellow solid was purified by column chromatography (fixed bed: (neutral silica gel, manufactured by KANTO CHEMICAL CO., INC., and 10% by mass potassium fluoride, solvent: dichloromethane/ethyl acetate (3/1, v/v) and 2% triethylamine), to thereby obtain a yellow solid.

The yellow solid was purified by Recycling Preparative HPLC (LC-9104, manufactured by Japan Analytical Industry Co., Ltd., solvent: THF), to thereby obtain Compound 15 as light yellow crystals. The amount of Compound 15 was 210 mg, and the yield was 42.7%.

The analysis result of Compound 15 is as follows.

$^1$H NMR (500 MHz, CDCl$_3$, TMS, δ): 0.85-0.91 (m, 12H), 1.29-1.33 (m, 16H), 1.63-1.69 (m, 8H), 1.99-2.04 (m, 4H), 2.32-2.37 (m, 12H), 6.15 (d, 4H, J=18.9 Hz), 7.46 (d, 2H, J=8.0 Hz), 7.65-7.69 (m, 6H), 7.95 (d, 2H, J=8.0 Hz), 8.11 (d, 2H, J=1.2 Hz)

Elemental analysis ($C_{58}H_{68}O_8S_2$)

|   | Found | Theoretical |
|---|-------|-------------|
| C | 72.50 | 72.77 |
| H | 7.43  | 7.16  |
| O | 13.57 | 13.37 |
| S | 6.49  | 6.70  |

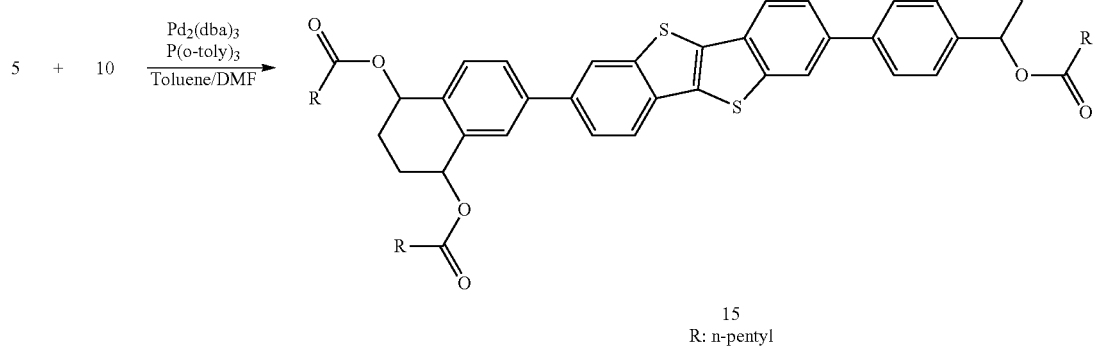

15
R: n-pentyl

A 100 mL-round bottom flask was charged with Compound 5 (1,020 mg, 2.1 mmol), Compound 10 (492 mg, 1.0 mmol) and DMF/toluene (25 mL), bubbled with argon gas for 30 minutes, and then further charged with tris(dibenzylideneacetone)dipalladium (0) (32.9 mg, 0.036 mmol) and tri Decomposition temperature: 179.0° C.

From the above analysis result, it was confirmed that a structure of the synthesized product did not contradict that of Compound 15.

Synthesis of Compound 16

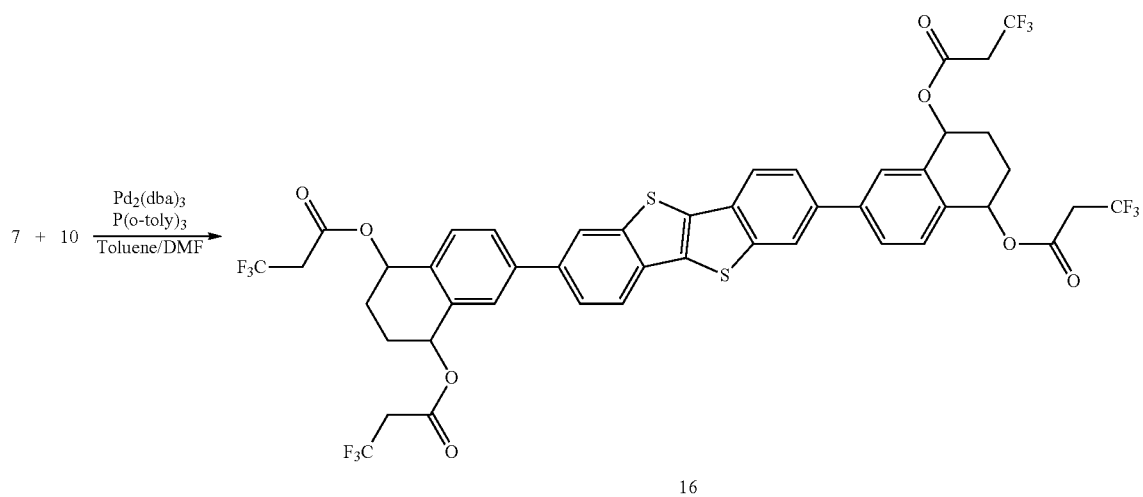 [SMILES: "Toluene/DMF" ; O=C(CC(F)(F)F)OC1CCC(OC(=O)CC(F)(F)F)c2cc(-c3ccc4c(c3)sc3c5ccc(-c6ccc7c(c6)C(OC(=O)CC(F)(F)F)CCC7OC(=O)CC(F)(F)F)cc5sc43)ccc21]

A 100 mL-round bottom flask was charged with Compound 7 (1,020 mg, 2.1 mmol), Compound 10 (492 mg, 1.0 mmol), and DMF/toluene (25 mL), bubbled with argon gas for 30 minutes, and then further charged with tris(dibenzylideneacetone)dipalladium (0) (18.3 mg, 0.02 mmol) and tri(ortho-tolyl)phosphine (24.4 mg, 0.08 mmol), followed by stirring for 8 hours at 80° C. in an argon atmosphere. The reaction solution was diluted with chloroform. The diluted solution was filtered through CELITE, and the insoluble matter was removed. Then, water was added to the filtrate so as to separate the organic layer. The aqueous layer was extracted with chloroform, and the combined organic layer was washed with saturated aqueous potassium fluoride solution, followed by washing with saturated brine, and drying with magnesium sulfate. The filtrate was condensed to obtain a yellow solid. The yellow solid was purified by column chromatography (fixed bed: (neutral silica gel, manufactured by KANTO CHEMICAL CO., INC.) and 10% by mass potassium fluoride, solvent: dichloromethane/ethyl acetate (3/1, v/v) and 2% triethylamine), to thereby obtain a yellow solid.

The yellow solid was purified by Recycling Preparative HPLC (LC-9104, manufactured by Japan Analytical Industry Co., Ltd., solvent: THF), to thereby obtain Compound 16 as light yellow crystals. The amount of Compound 16 was 180 mg, and the yield was 36.5%.

The analysis result of Compound 16 is as follows.

$^1$H NMR (500 MHz, CDCl$_3$, TMS, δ): 2.08-2.38 (m, 8H, H2, H3 of Tetralin), 3.19-3.33 (m, 8H, —CH2CF3), 6.12-6.25 (m, 4H, H1, H4 of Tetralin), 7.48-7.50 (m, 2H, ArH), 7.65-7.73 (m, 6H, ArH), 7.97 (d, 2H, J=8.6 Hz, ArH), 8.12 (d, 2H, J=1.2 Hz, ArH)

Elemental analysis (C$_{46}$H$_{32}$F$_{12}$O$_8$S$_2$)

|   | Found | Theoretical |
|---|-------|-------------|
| C | 55.17 | 54.98 |
| H | 3.41  | 3.21  |
| O | 12.95 | 12.74 |
| S | 6.07  | 6.38  |

Decomposition temperature: 218° C.

From the above analysis result, it was confirmed that a structure of the synthesized product did not contradict that of Compound 16.

Example 1

Synthesis of Naphthalene Using Leaving Substituent-Containing Compound 4

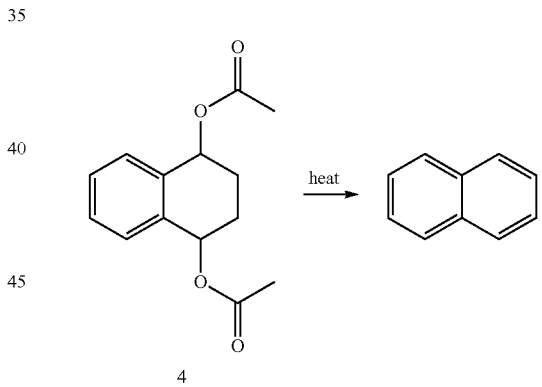

Compound 4 (100 mg) synthesized in Synthesis Example 1 was placed in a round bottom flask, and stirred at an internal temperature of 180° C. for 1 hour. In the flask, a glass tube equipped with a cooling part containing ice was placed, and the pressure inside the flask was reduced (40 mmHg), and sublimation purification was performed by heating while keeping the internal temperature at 80° C. Then, colorless crystals attached to the glass tube were scraped off for recovery. The amount of the colorless crystals was 51.5 mg, and the yield was 99.8%.

The analysis result of the crystals is as follows.

$^1$H NMR (500 MHz, CDCl$_3$, TMS, δ): 7.48 (d, 4H, J$_1$=6.8 Hz), 7.84 (d, 4H, J$_1$=8.3 Hz)

Mass spectrometry: GC-MS m/z=128 (M+)

Elemental analysis (C$_{10}$H$_8$)

|   | Found | Theoretical |
|---|---|---|
| C | 93.46 | 93.71 |
| H | 6.44 | 6.29 |

Melting point: 79.0° C. to 80.0° C.

Compound purity (LC-MS): 99.9%

From the result, it was confirmed that the colorless crystals obtained by the above-described reaction were naphthalene.

Example 2

Synthesis 1 of 2-Iodonaphthalene Using Leaving Substituent-Containing Compound 5

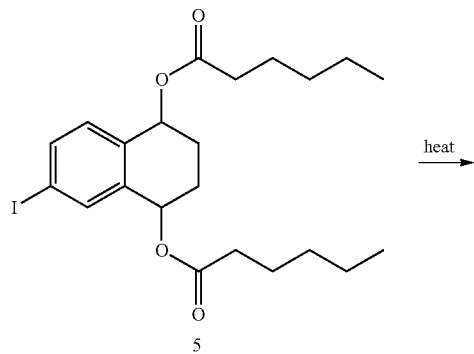

Compound 5 (97.28 mg, 0.2 mmol) synthesized in Synthesis Example 1 was placed in a round bottom flask, and stirred at an internal temperature of 180° C. for 1 hour. In the flask, a glass tube equipped with a cooling part containing ice was placed, and the pressure inside the flask was reduced (40 mmHg), and sublimation purification was performed by heating while keeping the internal temperature at 50° C. Then, colorless crystals attached to the glass tube were scraped off for recovery. The amount of the colorless crystals was 50.66 mg, and the yield was 99.7%.

The analysis result of the crystals is as follows.

$^1$H NMR (400 MHz, CDCl$_3$, TMS, δ): 7.46-7.52 (m, 2H) 7.55-7.58 (m, 1H), 7.68-7.74 (m, 2H), 7.76-7.82 (m, 1H), 8.22-8.26 (m, 1H)

Mass spectrometry: GC-MS m/z=254 (M+)

Elemental analysis ($C_{10}H_7I$)

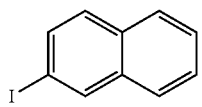

|   | Found | Theoretical |
|---|---|---|
| C | 47.11 | 47.27 |
| H | 2.94 | 2.78 |

Melting point: 50.5° C. to 52.0° C.

Compound purity (LC-MS): ≥99.8%

From the result, it was confirmed that the colorless crystals obtained by the above-described reaction were 2-iodonaphthalene.

Example 3

Synthesis of 2-Iodonaphthalene Using Leaving Substituent-Containing Compound 6

The reaction was performed in the same manner as in Example 2, except that Compound 5 used in Example 2 was replaced with Compound 6 (91.67 mg, 0.2 mmol).

Then, colorless crystals attached to the glass tube were scraped off for recovery. The amount of the colorless crystals was 50.46 mg, and the yield was 99.3%.

The crystals were analyzed as described below, and obtained the same analysis result as that of Example 2.

Thus, it was confirmed that the colorless crystals obtained by the above-described reaction were 2-iodonaphthalene.

Example 4

Synthesis of 2-Iodonaphthalene Using Leaving Substituent-Containing Compound 7

The reaction was performed in the same manner as in Example 2, except that Compound 6 used in Example 2 was replaced with Compound 7 (102.0 mg, 0.2 mmol), and that the internal temperature of the flask was changed to 160° C.

Then, colorless crystals attached to the glass tube were scraped off for recovery. The amount of the colorless crystals was 50.76 mg, and the yield was 99.9%.

The crystals were analyzed as described below, and obtained the same analysis results as that of Example 2.

Thus, it was confirmed that the colorless crystals obtained by the above-described reaction were 2-iodonaphthalene.

Examples 1 to 4 indicated that using the leaving substituent-containing compound, naphthalene and the derivatives thereof were quantitatively obtained at a relatively low temperature of 180° C. or less and with high yield of 99% or more. It was also indicated that, in the case of the compound having an alkyl group partially halogenated (fluorinated) with high electron attraction properties, the reaction was completed at lower temperature.

Example 5

Synthesis 1 of Organic Semiconductor Compound 1 (Compound 17)

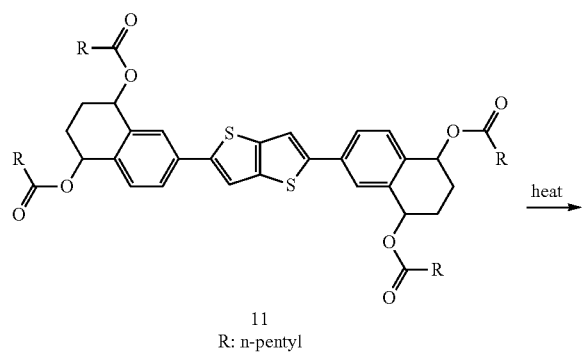

11
R: n-pentyl

| | Found | Theoretical |
|---|---|---|
| C | 79.84 | 79.55 |
| H | 4.00 | 4.11 |
| S | 16.10 | 16.34 |

Mass spectrometry: GC-MS m/z=392 (M+)
Melting point: 357.7° C.
Compound purity (GCMS): ≥99.8%

From the above analysis result, it was confirmed that a structure of the synthesized product did not contradict that of Compound 17.

Example 6

Synthesis 2 of Organic Semiconductor Compound 1 (Compound 17)

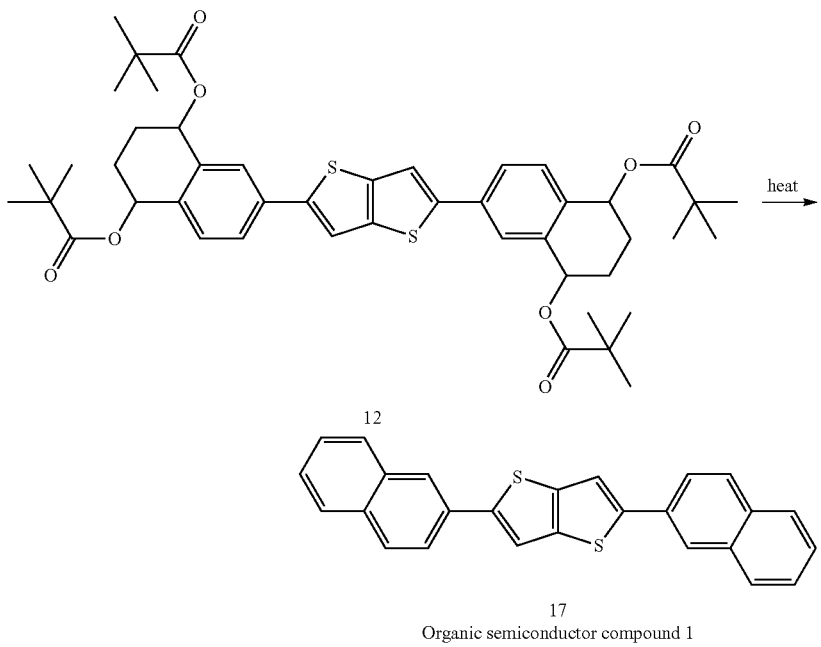

12

17
Organic semiconductor compound 1

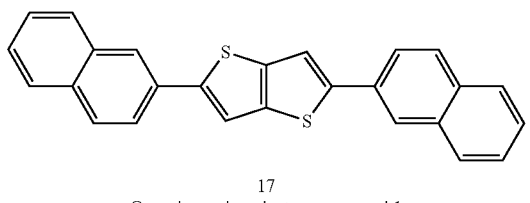

17
Organic semiconductor compound 1

A round bottom flask was charged with Compound 11 (200 mg, 0.23 mmol) synthesized in Synthesis Example 3, and heated at 245° C. (internal temperature of the flask) and stirred for 1 hour in an argon atmosphere.

The obtained solid was washed with toluene, further washed with methanol, and dried in vacuum, to thereby obtain Compound 17 as yellow crystals. The amount of Compound 17 was 86.9 mg, and the yield was 96.3%. The analysis result of Compound 17 is as follows.

Elemental analysis ($C_{26}H_{16}S_2$)

A reaction and purification were performed in the same manner as in Example 5, except that Compound 11 was replaced with Compound 12 (184.2 mg, 0.23 mmol), and that the reaction temperature was changed to 270° C.

Similar to Example 5, Compound 17 as yellow crystals was obtained. The amount of Compound 17 was 86.3 mg, and the yield was 96.3%.

The analysis result of Compound 17 obtained in this reaction was as described below.

Elemental analysis ($C_{26}H_{16}S_2$)

| | Found | Theoretical |
|---|---|---|
| C | 79.64 | 79.55 |
| H | 4.10 | 4.11 |
| S | 16.20 | 16.34 |

Mass spectrometry: GC-MS m/z=392 (M+)
Melting point: 357.2° C.
Compound purity (GCMS): 99.7%

From the above analysis result, it was confirmed that a structure of the synthesized product did not contradict that of Compound 17.

Example 7

Synthesis 3 of Organic Semiconductor Compound 1 (Compound 17)

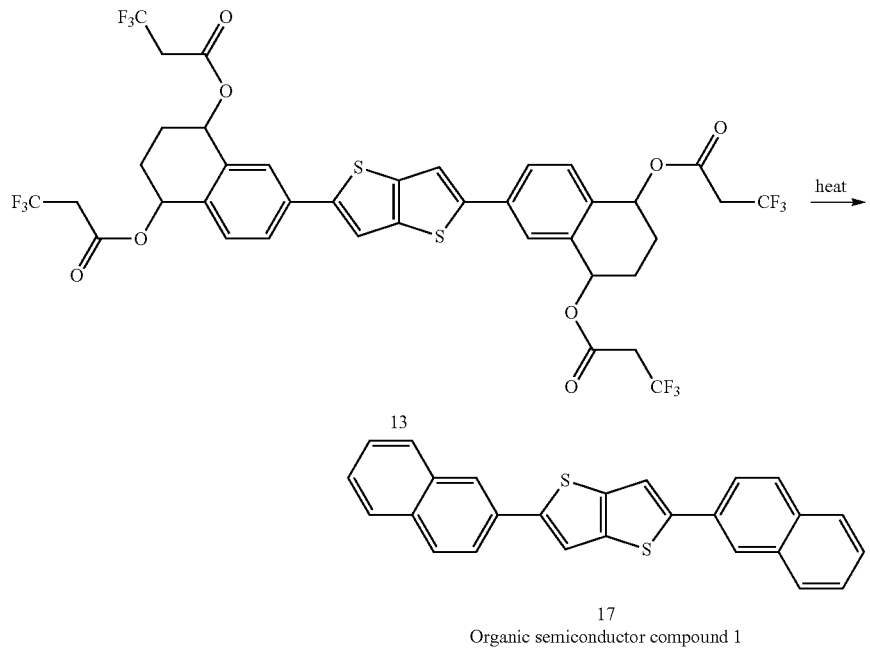

A reaction and purification were performed in the same manner as in Example 5, except that Compound 11 was replaced with Compound 13 (219.6 mg, 0.23 mmol), and that the reaction temperature was changed to 200° C.

Similar to Example 5, Compound 17 as yellow crystals was obtained. The amount of Compound 17 was 89.2 mg, and the yield was 98.8%. The analysis result of Compound 17 obtained in this reaction was as described below.

Elemental analysis ($C_{26}H_{16}S_2$)

|   | Found | Theoretical |
|---|-------|-------------|
| C | 79.58 | 79.55 |
| H | 4.11  | 4.11  |
| S | 16.32 | 16.34 |

Mass spectrometry: GC-MS m/z=392 (M+)

Melting point: 357.2° C.

Compound purity (GCMS): 99.7%

From the above analysis result, it was confirmed that a structure of the synthesized product did not contradict that of Compound 17.

Example 8

Synthesis of Organic Semiconductor Compound 2 (Compound 18)

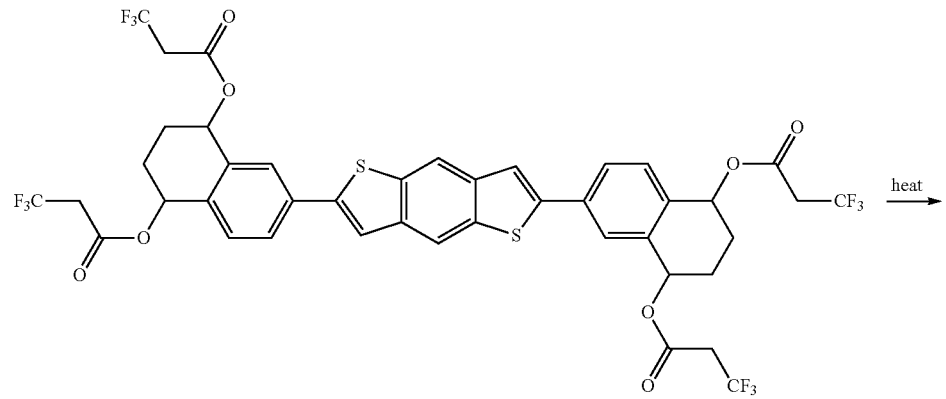

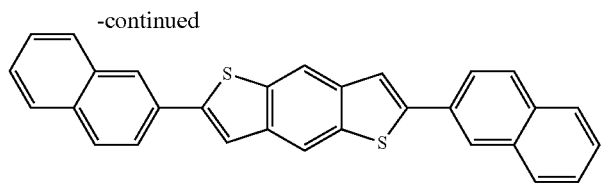

18
Organic semiconductor compound 2

A reaction was performed in the same manner as in Example 5, except that Compound 11 was replaced with Compound 14 (208.1 mg, 0.23 mmol), and that the reaction temperature was changed to 240° C. The obtained solid was washed sequentially with chloroform, acetone, and methanol, and dried in vacuum, to thereby obtain Compound 18 as yellow green crystals. The amount of Compound 18 was 100 mg, and the yield was 98.3%. The analysis result of Compound 18 obtained in this reaction was as described below.

From the above analysis result, it was confirmed that a structure of the synthesized product did not contradict that of Compound 18.

Example 9

Synthesis 1 of Organic Semiconductor Compound 3 (Compound 19)

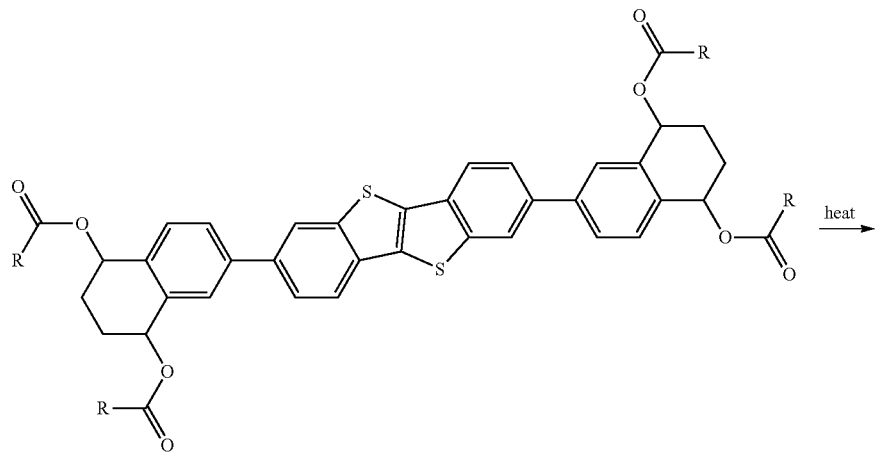

15
R: n-pentyl

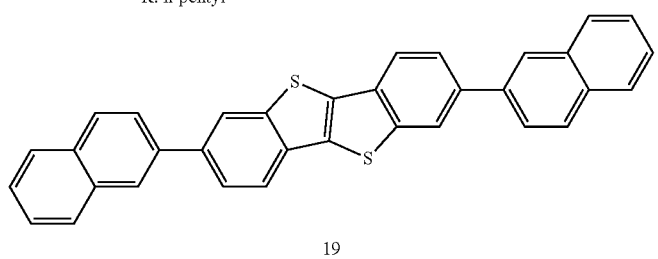

19
Organic semiconductor compound 3

Elemental analysis value ($C_{30}H_{18}S_2$)

|   | Found value | Theoretical value |
|---|---|---|
| C | 81.21 | 81.41 |
| H | 4.10 | 4.10 |
| S | 14.59 | 14.49 |

Mass spectrometry: GC-MS m/z=442 (M+)

Melting point: 438.2° C.

Compound purity (GCMS): 99.8%

A reaction was performed in the same manner as in Example 5, except that Compound 11 was replaced with Compound 15 (208.1 mg, 0.23 mmol), and that the reaction temperature was changed to 255° C. The obtained solid was washed sequentially with chloroform and methanol, and dried in vacuum, to thereby obtain Compound 19 as light yellow crystals. The amount of Compound 19 was 110 mg, and the yield was 97.1%. The analysis result of Compound 19 obtained in this reaction was as described below.

Elemental analysis ($C_{34}H_{20}S_2$)

|   | Found | Theoretical |
|---|-------|-------------|
| C | 82.67 | 82.89 |
| H | 4.10  | 4.09  |
| S | 13.14 | 13.02 |

Mass spectrometry: GC-MS m/z=492(M+)
Melting point 378.2° C.
Compound purity (GCMS): 99.5%

From the above analysis result, it was confirmed that a structure of the synthesized product did not contradict that of Compound 19.

Example 10

Synthesis 2 of Organic Semiconductor Compound 3 (Compound 19)

|   | Found | Theoretical |
|---|-------|-------------|
| C | 82.52 | 82.89 |
| H | 4.08  | 4.09  |
| S | 13.17 | 13.02 |

Mass spectrometry: GC-MS m/z=492 (M+)
Melting point: 377.9° C.
Compound purity (GCMS): 99.4%

From the above analysis result, it was confirmed that a structure of the synthesized product did not contradict that of Compound 19.

The results of Examples 10 to 15 indicated that a sparingly soluble π-electron conjugated compound could be obtained at a high yield of 97% or more with a high purity of 99% or more only by heating and washing at approximately 200° C. to approximately 250° C.

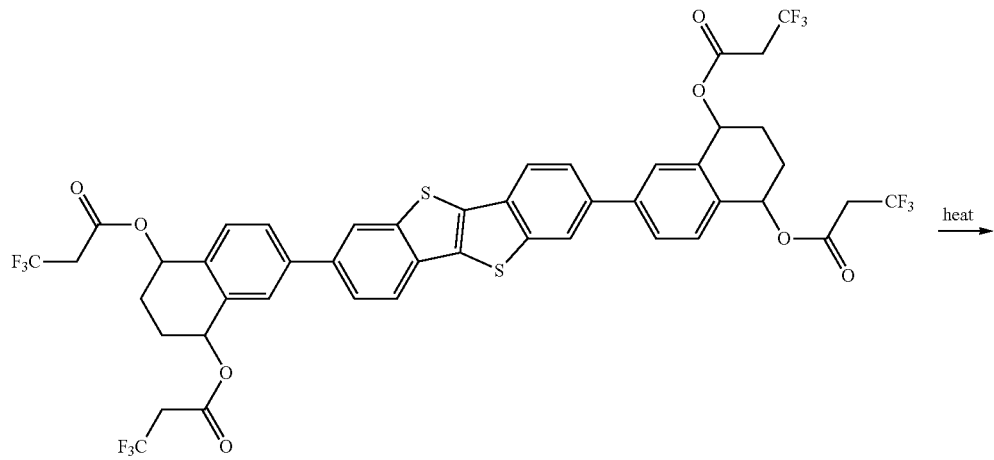

16

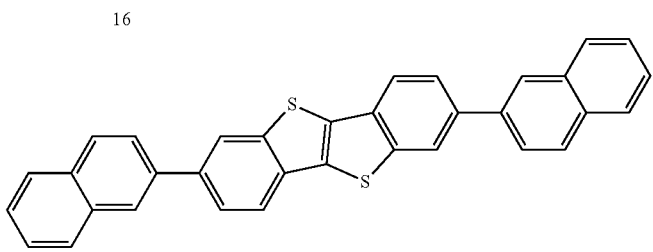

19
Organic semiconductor compound 3

A reaction was performed in the same manner as in Example 5, except that Compound 11 was replaced with Compound 16 (208.1 mg, 0.23 mmol), and that the reaction temperature was changed to 220° C. The obtained solid was washed sequentially with chloroform, acetone, and methanol, and dried in vacuum, to thereby obtain Compound 19 as light yellow crystals. The amount of Compound 18 was 111.8 mg, and the yield was 98.7%.

The analysis result of Compound 19 obtained in this reaction was as described below.

Elemental analysis ($C_{34}H_{20}S_2$)

It was found that the conversion temperature was approximately the sublimation temperature or lower of each compound. The sublimation temperature is defined as a temperature at which the mass of a compound reduces by 1%. For example, in FIG. 2, after termination of reduction of mass upon conversion, substantially horizontal line is observed at 300° C. to 340° C. in the graph. And, the mass is reduced by 1% or more at a temperature of 340° C. or higher, and thus, it was considered that the compound was sublimated.

It was indicated that the method was an effective method not only for the production of an organic solvent soluble low molecular weight compounds such as naphthalene, but also for production of a π-electron conjugated compound normally sparingly soluble in an organic solvent.

These can be used in many molecules, such as pigments, organic semiconductor molecules, etc.

Example 11

Evaluation of Solubility

Each of Compound 11 to Compound 19 synthesized in Synthesis Example 3 was added to toluene, THF, anisole, and chloroform (each 2.0 mg), until the compound was not dissolved therein, and stirred for 10 minutes under reflux of the solvent, and cooled down to room temperature. The mixture was further stirred for 1 hour and left to stand for 16 hours, and the supernatant was filtered using a 0.2 μm-PTFE filter, to thereby obtain a saturated solution. The saturated solution was dried under reduced pressure, and the solubility of the precursor in each solvent was calculated. The results are shown in Table 1.

TABLE 1

| Solvent | Toluene | THF | Anisole | Chloroform |
|---|---|---|---|---|
| Compound 11 | A | A | B | A |
| Compound 12 | A | A | A | A |
| Compound 13 | A | A | B | A |
| Compound 14 | B | A | A | A |
| Compound 15 | A | A | B | A |
| Compound 16 | B | A | B | A |
| Compound 17 | D | D | D | D |
| Compound 18 | D | D | D | D |
| Compound 19 | D | D | D | D |

In Table 1, A denotes that the solubility is 0.5% by mass or more; B denotes that the solubility is 0.1% by mass or more to less than 0.5% by mass; C denotes that the solubility is 0.005% by mass or more to less than 0.1% by mass; and D denotes that the solubility is less than 0.005% by mass.

In any case using Compounds 11 to 16, the compound from which the precursor compound had undergone elimination (i.e., Compounds 17 to 19) under reflux of the solvent could not be confirmed.

From Table 1, it was confirmed that the compounds had a solubility of approximately 0.1% by mass or more to the various solvents having different polarities. It was apparent that the compound had high selectivity of solvent in a coating process.

Table 1 indicated that Compound 17, 18 and 19 which were converted materials had a solubility of 0.005% by mass or less to those solvents, and that the compound converted by elimination reaction became insoluble to the solvents.

It was found that in the state of solution, the compound had thermal stability and storage stability, so that the compound is not decomposed even in reflux of anisole (154° C.).

The reason is not certain, but it is considered that when the distance between molecules is very close like a solid state, elimination easily occurs, but when there is a certain distance between molecules like in a solution state, elimination does not easily occur.

Example 12

Observation of Elimination Behavior of Compound 11

Compound 11 (5 mg) synthesized in Synthesis Example 3 was heated on a silicon wafer which was placed on a hot plate set at given temperatures of 150° C., 160° C., 170° C., 180° C., 220° C., 230° C., 240° C., and 260° C. for 30 minutes so as to prepare a sample.

IR spectra (KBr method, SPECTRUM GX, manufactured by PerkinElmer, Inc.) of the sample, Compound 11 before heating and Compound 17 which had been converted were measured. The results are shown in FIG. 1.

Under the heating condition at 240° C., —O— (1,156 cm$^{-1}$) absorption and C=O (1,726 cm$^{-1}$) absorption were disappeared, and new absorptions (810 cm$^{-1}$, 738 cm$^{-1}$, 478 cm$^{-1}$, aromatic series) were confirmed. This was identified with the spectrum of Compound 17.

Figure 2:
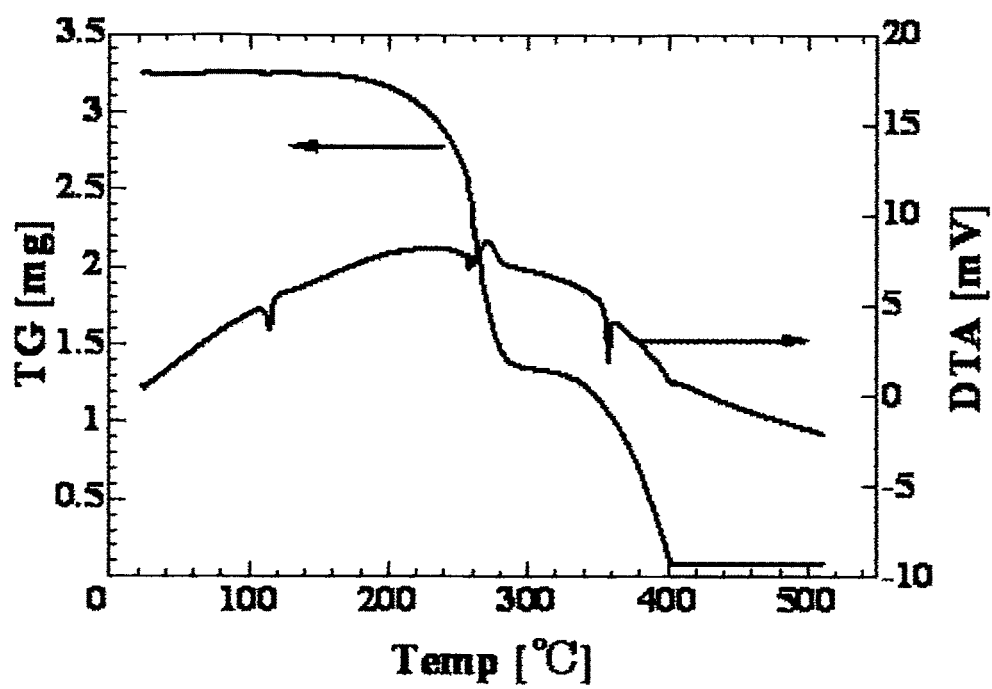
FIG. 2 is a TG-DTA graph of Compound 11 in which the horizontal axis indicates a temperature [° C.], the left vertical axis indicates a change in mass [mg], and the right vertical axis indicates a differential heat [mV].

Compound 11 was heated at a range of 25° C. to 500° C. at a temperature increase rate of 5° C./min and the pyrolysis behavior thereof was observed by TG-DTA (EXSTAR6000, manufactured by Seiko Instruments Inc.) using Al$_2$O$_3$ as a reference in a nitrogen airflow (200 mL/min). The results are shown in FIG. 2.

In TG-DTA, 56.7% of mass reduction was observed from 160° C. to 290° C.

The mass reduced coincided substantially with that of 4 molecules of caproic acid (theoretical value: 54.2%). It was confirmed that a melting point was 357.7° C. This was identified with the melting point of Compound 17.

These results showed that Compound 11 was converted to Compound 17 by heating.

Moreover, these results showed that a threshold of elimination reaction was about 240° C.

Example 13

Observation of Elimination Behavior of Compound 12

A sample was prepared, IR spectrum was measured, and a conversion temperature was estimated in the same manner as in Example 12, except that Compound 11 of Example 12 was replaced with Compound 12, and that the heating conditions were 170° C., 180° C., 200° C., 220° C., 240° C., 250° C., 260° C., 280° C., and 300° C.

Under the heating condition at 280° C., —O— (1,156 cm$^{-1}$) absorption and C=O (1,726 cm$^{-1}$) absorption were disappeared, and new absorptions (810 cm$^{-1}$, 738 cm$^{-1}$, 478 cm$^{-1}$, aromatic series) were confirmed. TG-DTA of Compound 12 was measured in the same manner as in Compound 11. In TG-DTA, 58.2% of mass reduction was observed from 250° C. to 285° C. The mass reduced was somewhat larger than 4 molecules of pivalic acid (theoretical value: 51.0%). It was confirmed that a melting point was 357.2° C. This was identified with the melting point of Compound 17.

These results showed that Compound 12 was converted to Compound 17 by heating.

Moreover, these results showed that a threshold of elimination reaction was about 280° C.

Example 14

Observation of Elimination Behavior of Compound 15

A sample was prepared, IR spectrum was measured, and a conversion temperature was estimated in the same manner as in Example 12, except that Compound 11 of Example 12 was replaced with Compound 15, and that the heating conditions were 180° C., 200° C., 220° C., 230° C., 240° C., 250° C., 260° C., and 280° C. Under the heating condition at 250° C., —O— (1,156 cm$^{-1}$) absorption and C=O (1,726 cm$^{-1}$) absorption were disappeared, and new absorptions (810 cm$^{-1}$, 738 cm$^{-1}$, 478 cm$^{-1}$, aromatic series) were confirmed. This was identified with the spectrum of Compound 19. TG-DTA of Compound 15 was measured in the same manner as in Compound 11. In TG-DTA, 50.7% of mass reduction was observed from 200° C. to 300° C. The mass reduced coincided substantially with four molecules of caproic acid (theoretical value: 48.5%). It was confirmed that a melting point was 358.2° C. This was identified with the melting point of Compound 19.

These results showed that Compound 15 was converted to Compound 19 by heating.

Moreover, these results showed that a threshold of elimination reaction was about 250° C.

Example 15

Observation of Elimination Behavior of Compound 13

A sample was prepared, IR spectrum was measured, and a conversion temperature was estimated in the same manner as in Example 12, except that Compound 11 of Example 12 was replaced with Compound 13, and that the heating conditions were 180° C., 190° C., 200° C., 220° C., 230° C., and 240° C. Under the heating condition at 200° C., —O— (1,156 cm$^{-1}$) absorption and C=O (1,726 cm$^{-1}$) absorption were disappeared, and new absorptions (810 cm$^{-1}$, 738 cm$^{-1}$, 478 cm$^{-1}$, aromatic series) were confirmed. This was identified with the spectrum of Compound 17. TG-DTA of Compound 13 was measured in the same manner as in Compound 11. In TG-DTA, 57.0% of mass reduction was observed from 180° C. to 220° C. The mass reduced coincided substantially with 3,3,3-trifluoropropionic acid (theoretical value: 56.6%). It was confirmed that a melting point was 358.0° C. This was identified with the melting point of Compound 17.

These results showed that Compound 13 was converted to Compound 17 by heating.

Moreover, these results showed that a threshold of elimination reaction was about 200° C.

From these Examples, the elimination behavior and the threshold temperature of elimination reaction could be estimated. It was confirmed that the π-conjugated core to be combined caused less effect, but that the temperature at which elimination reaction occurred changed depending on an alkyl chain introduced to an ester site. The higher the acidity (pKa) of an alkyl chain, namely carboxylic acid as an eliminated component was, the lower the elimination temperature was. The pivalic acid had an acidity of 5.0 pKa, the caproic acid had an acidity of 4.6 pKa, and the 3,3,3-trifluoropropionic acid had an acidity of 3.0 pKa. It was confirmed that a desired π-electron conjugated compound could be obtained by heating the compound of the present invention at approximately 250° C.

It was considered that in Examples 12 to 14, the mass reduction of the found value was larger than that of the theoretical value, because Compounds 17 and 19 were relatively highly sublimated under the conditions of high temperature and nitrogen air flow, and the solvent was contained in the crystals of the precursor.

Example 16

Production Example of Thin Film

Each of Compounds 11, 14 and 15 (each 5 mg) synthesized in Synthesis Example 3 was dissolved in THF, so that the concentration of each compound became 0.1% by mass, and the mixture was filtered using a 0.2 µm-filter, to prepare a solution. Onto a N-type silicon substrate having a 300 nm-thick thermally-oxidized film, which had been soaked in concentrated sulfuric acid for 24 hours, 100 µl, of the prepared solution was added dropwise, and then the substrate was covered with a petri dish and left to stand until the solvent was dried, to thereby form a thin film. The thin film was observed with a polarization microscope and a scanning probe microscope (NANOPICS, manufactured by Seiko Instruments Inc., contact mode), and it was confirmed that a smooth and continuous amorphous film was obtained.

Figure 3A:
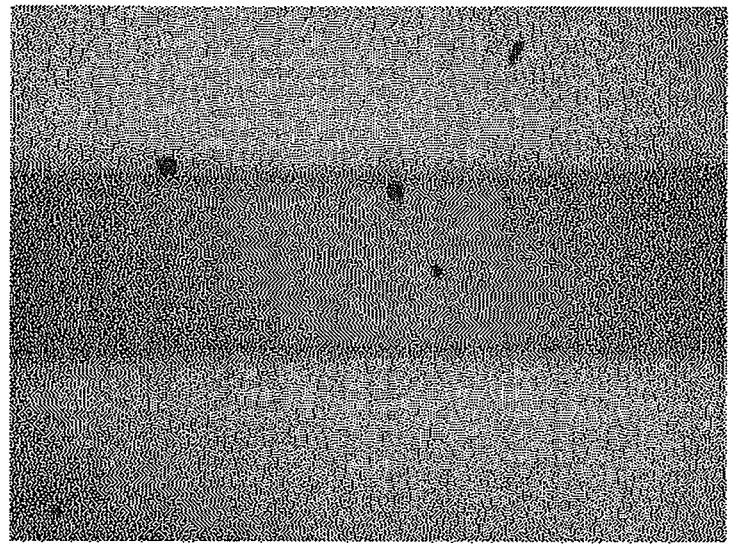
FIG. 3A is a photograph of a film made of a compound of the present invention, which is taken with a polarization microscope (open Nicol).
Figure 3B:
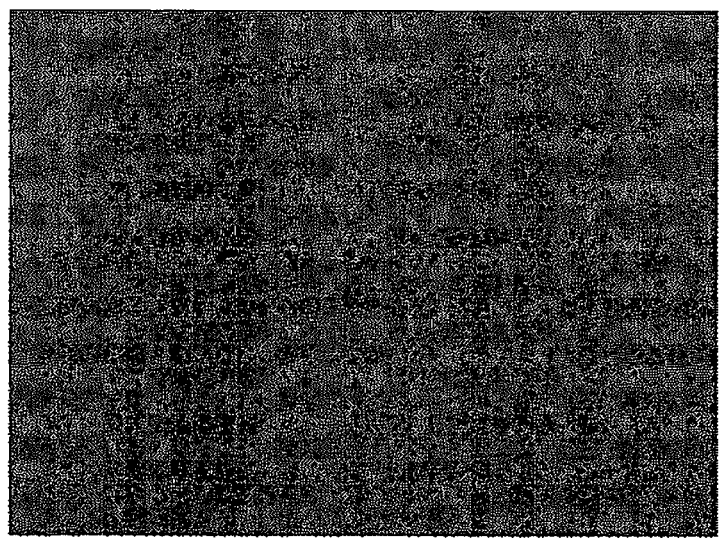
FIG. 3B is a photograph of a film made of a compound of the present invention, which is taken with a polarization microscope (cross Nicol).
Figure 4A:
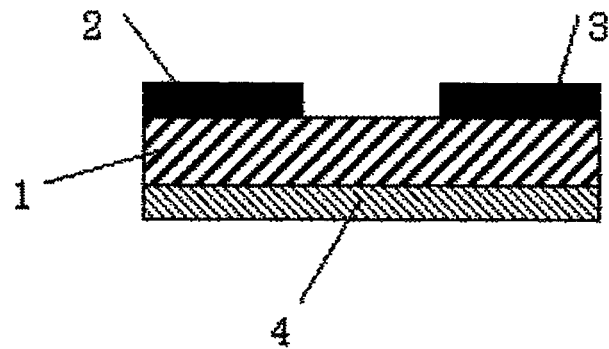
FIG. 4A schematically illustrates an organic thin-film transistor (part 1).
Figure 4B:
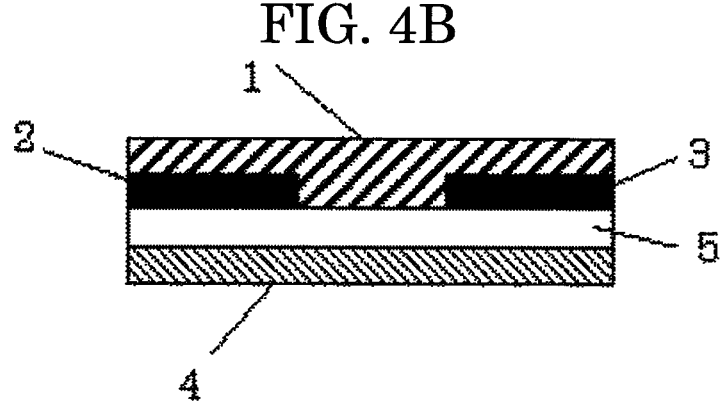
FIG. 4B schematically illustrates an organic thin-film transistor (part 2).
Figure 4C:
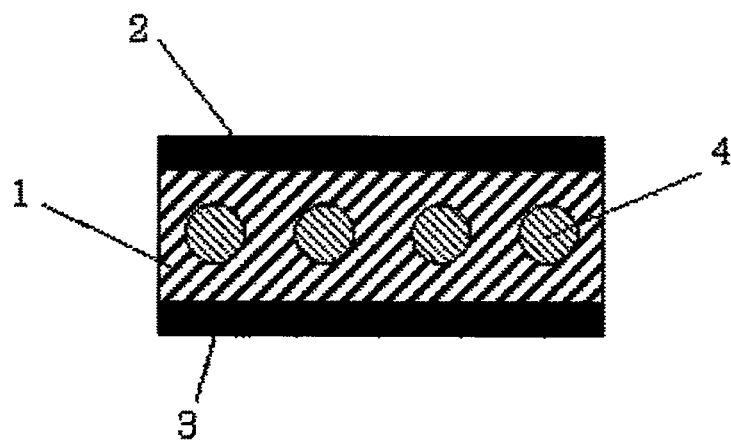
FIG. 4C schematically illustrates an organic thin-film transistor (part 3).
Figure 4D:
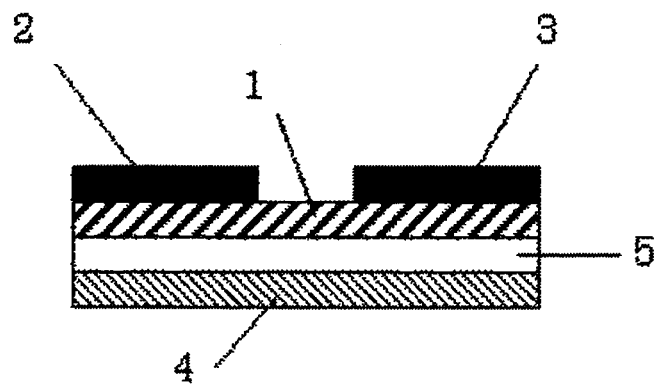
FIG. 4D schematically illustrates an organic thin-film transistor (part 4).

Next, the thin film was subjected to annealing for 30 minutes at 250° C. in an argon atmosphere. Then, the thin film was observed in the same manner as described above. After anneal treatment, a plurality of colored domains were observed with the polarization microscope, and it was confirmed that a smooth and crystalline film was obtained. The polarization microscope pictures of these films are shown in FIGS. 3A and 3B. These films were obtained because each of Compounds 11, 14 and 15 as precursors, in which an ester group which was a soluble group was eliminated, so that Compound 11, 14 and 15 were respectively converted into Compound 17, 18 and 19 having stronger intermolecular interaction, and became crystalline in the film.

The thin film was insoluble in chloroform, THF, toluene, etc. at 25° C.

Comparative Example 1

The preparation of a solution and production of a thin film of Comparative Example 1 were performed in the same manner as in Example 16, except that Compounds 11, 14 and 15 were replaced with Compound 17, 18 and 19, and that THF were replaced with dichlorobenzene heated at 150° C.

In all films, crystals were precipitated in such a degree that it could be recognized by visual observation, and it was confirmed that noncontinuous film was formed. Under the polarization microscope, a plurality of noncontinuous colored domains were observed. Under the scanning probe microscope, a surface roughness of 100 µm or more was confirmed.

These results indicated that the production method of the present invention was effective on thin film deposition using sparingly soluble compounds, which were slightly dissolved in some solvents each having a high boiling point.

Example 17

Production and Evaluation of Organic Thin Film Transistor Through Wet Process Using Solution Thin film containing Compound 11 was produced in the same manner as in Example 16. The thin film was subjected to annealing for 30 minutes at 250° C. in an argon atmosphere, so as to convert to a thin film formed of Organic Semiconductor Compound 1, and having a thickness of 50 nm.

On the thin film, gold was vacuum deposited via a shadow mask under the condition of back pressure of up to 10$^{-4}$ Pa, deposition rate of 1 Å/s to 2 Å/s and film thickness of 50 nm, thereby forming source and drain electrodes having a channel length of 50 µm and channel width of 2 mm. Thus, a field-effect transistor (FET) element having a structure shown in FIG. 4D was produced. The organic semiconductor film and silicon oxide film in a region other than the gold electrodes were removed by scraping, and a conductive paste (manufactured by Fujikura Kasei Co., Ltd.) was applied in the region and the solvent was dried. Through the region, voltage was applied to the silicon substrate serving as the gate electrode.

Figure 5:
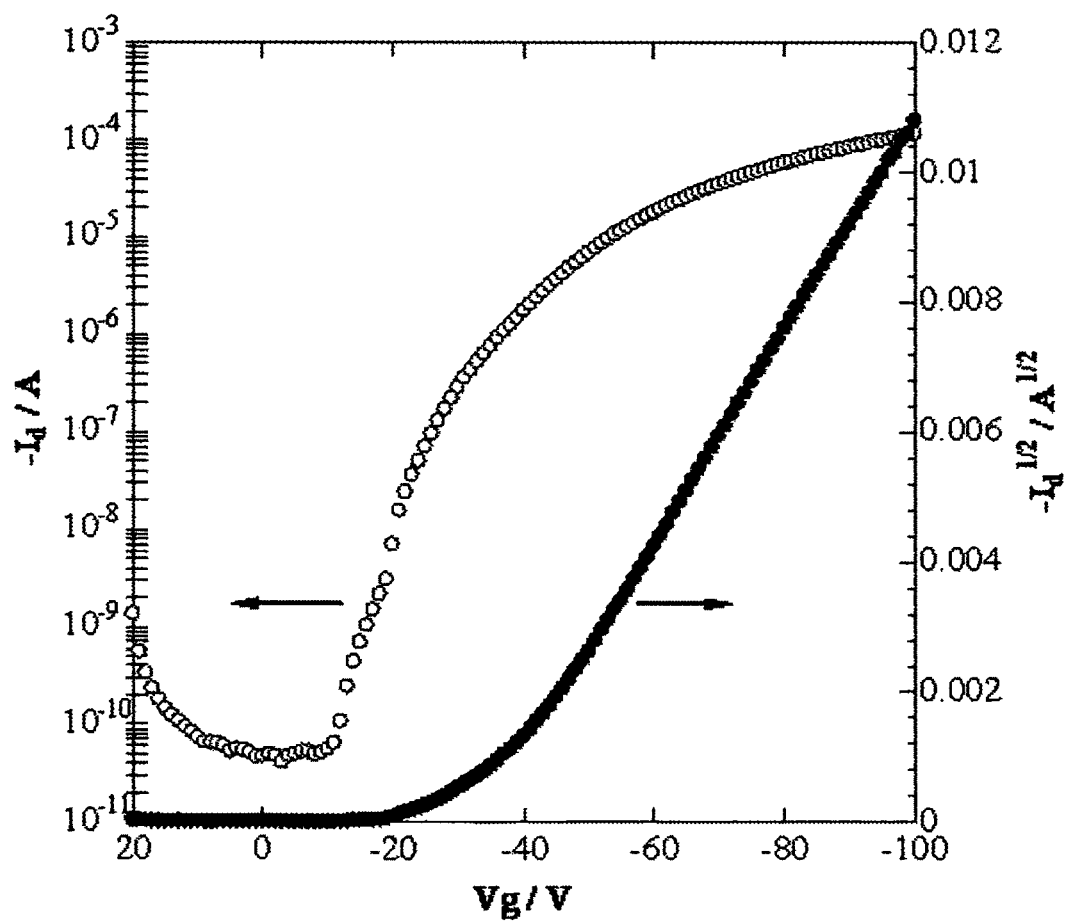
FIG. 5 is a current-voltage graph of an organic thin-film transistor of the present invention.

The electric property of the FET element was evaluated by a semiconductor parameter analyzer B1500A (manufactured by Agilent Technologies) under the measurement conditions of fixed source drain voltage: −100V, and gate voltage sweep: from −20V to +100V). The FET element exhibited a property as a p-type transistor element. The current and voltage (I-V) characteristics of the organic thin film transistor (FET element) is shown in FIG. 5. In FIG. 5, a white circle represents an absolute value of drain current on the left vertical axis, and a black circle represents a square root of the absolute value of drain current on the right vertical axis. The applied gate electrode is on the horizontal axis.

From the saturation region of the current and voltage (I-V) characteristics of the organic thin film transistor, a field-effect mobility was obtained. The field-effect mobility of the organic thin-film transistor was calculated by the following equation.

$$Ids = \mu Cin W(Vg-Vth)2/2L$$

In the equation, Cin is a capacitance per unit area of a gate insulating film, W is a channel width, L is a channel length, Vg is a gate voltage, Ids is a source-drain current, $\mu$ is a field effect mobility and Vth is a gate threshold voltage at which a channel begins to be formed.

Moreover, a ratio of an on-current at a gate voltage of 100 V to an off-current at a gate voltage of 0 V was obtained as a current on/off ratio. The results are shown in Table 2.

As a result, a saturation mobility was $2.8 \times 10^{-2}$ cm$^2$/Vs, and a current on/off ratio was $3.0 \times 10^7$.

Example 18

A FET element was produced, and then evaluation of properties was performed in the same manner as in Example 17, except that Compound 11 of Example 17 was replaced with Compound 14, and then a thin film was converted into a thin film formed of Organic Semiconductor Compound 2. The results are shown in Table 2.

As a result, a saturation mobility was $4.3 \times 10^{-2}$ cm$^2$/Vs, and a current on/off ratio was $2.0 \times 10^7$.

Example 19

A FET element was produced, and then evaluation of properties was performed in the same manner as in Example 17, except that Compound 11 of Example 17 was replaced with Compound 15, and then a thin film was converted into a thin film formed of Organic Semiconductor Compound 3. The results are shown in Table 2.

As a result, a saturation mobility was $5.5 \times 10^{-2}$ cm$^2$/Vs, and a current on/off ratio was $4.1 \times 10^7$.

Comparative Example 2

A thin film formed of Organic Semiconductor Compound 1 was produced on the same substrate as that in Example 17 using the dichlorobenzene solution described in Comparative Example 1, and then an FET element was produced, and evaluation of properties was performed. The results are shown in Table 2.

Comparative Example 3

A thin film formed of Organic Semiconductor Compound 3 was produced on the same substrate as that in Example 17 using the dichlorobenzene solution described in Comparative Example 1, and then an FET element was produced, and evaluation of properties was performed. The results are shown in Table 2.

Comparative Example 4

A thin film formed of Organic Semiconductor Compound 3 was produced on the same substrate as that in Example 17 using the dichlorobenzene solution described in Comparative Example 1, and then an FET element was produced, and evaluation of properties was performed. The results are shown in Table 2.

TABLE 2

|  | Mobility (cm$^2$/Vs) | On/off ratio (Id$_{100v}$/Id$_{0v}$) |
| --- | --- | --- |
| Example 17 | $2.8 \times 10^{-2}$ | $3.0 \times 10^7$ |
| Example 18 | $4.3 \times 10^{-2}$ | $2.0 \times 10^7$ |
| Example 19 | $5.5 \times 10^{-2}$ | $4.1 \times 10^7$ |
| Comparative Example 2 | Not operated | Not operated |
| Comparative Example 3 | Not operated | Not operated |
| Comparative Example 4 | Not operated | Not operated |

From these Examples, it was apparent that excellent FET characteristics could be obtained even through a wet process using solution by using a leaving substituent-containing compound of the present invention, and converting the compound to a film containing an organic semiconductor compound, although excellent FET characteristics cannot be obtained by forming a film only by solving a sparingly soluble organic semiconductor compound in a solvent having a high boiling point. It was apparent that the organic thin film transistor of the present invention exhibited excellent hole mobility, current on/off ratio, and had excellent characteristics as an organic thin film transistor. Therefore, the leaving substituent-containing compound of the present invention, and the organic semiconductor compound obtained by using the leaving substituent-containing compound are useful for production of an organic electronic device, such as an organic thin film transistor.

INDUSTRIAL APPLICABILITY

The leaving substituent-containing compound of the present invention is excellent in solubility in various organic solvents, and can synthesize a specific compound, and an organic semiconductor compound with high yield without generating olefin end-groups by elimination reaction occurred by application of energy, thereby having excellent processability.

Since an organic semiconductor compound is a sparingly soluble, it is difficult to form a film. However, the leaving substituent-containing compound is used for film formation as an organic semiconductor compound precursor, followed by converting to an organic semiconductor compound with, for example, heat, thereby easily obtaining a continuous organic semiconductor film. Moreover, the organic semiconductor film can be patterned by removing unconverted portions by washing, thus, the film formed by using the leaving substituent-containing compound of the present invention may be applied to organic electronic devices, particularly, applied to electronic devices such as semiconductors, and optical electronic devices such as EL light-emitting elements, photoelectric conversion device such as thin film solar battery, dye-sensitized solar battery, electronic paper, various sensors, and radio frequency identifications (RFIDs).

According to the production method of the present invention, a π-electron conjugated compound containing a benzene ring can be synthesized without generating olefin end-groups with high yield by elimination reaction occurred by application of energy, thereby having excellent processability.

By using the production method of the present invention, a continuous film of a sparingly soluble compound can be usually obtained through a wet process using a solution, although a continuous film can be obtained only by vacuum-deposition using a sparingly soluble compound. This process may be applied to organic electronic devices, particularly, applied to electronic devices such as semiconductors, and optical electronic devices such as EL light-emitting elements, photoelectric conversion device such as thin film solar battery, dye-sensitized solar battery, electronic paper, various sensors, and radio frequency identifications (RFIDs).

The invention claimed is:

1. A leaving substituent-containing compound, having a structure represented by Formula (I):

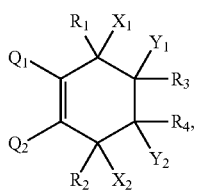

Formula (I)

wherein:
a pair of $X_1$ and $X_2$ or a pair of $Y_1$ and $Y_2$ each represent a hydrogen atom, and the other pair each represent a group selected from the group consisting of a halogen atom and a substituted or unsubstituted acyloxy group having one or more carbon atoms;
a pair of the acyloxy groups represented by the pair of $X_1$ and $X_2$ or the pair of $Y_1$ and $Y_2$ are optionally identical or different, or are optionally bonded together to form a ring;
$R_1$ to $R_4$ each represent a hydrogen atom or a substituent; and
$Q_1$ and $Q_2$ each represent a hydrogen atom, a halogen atom or a monovalent organic group, and are optionally bonded together to form a ring.

2. The leaving substituent-containing compound according to claim 1, wherein the structure represented by Formula (I) comprises a partial structure represented by Formula (III):

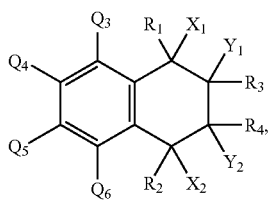

Formula (III)

wherein:
$Q_3$ to $Q_6$ each represent a hydrogen atom, a halogen atom or a monovalent organic group;

$Q_3$ and $Q_4$ are optionally bonded together to form a ring;
$Q_4$ and $Q_5$ are optionally bonded together to form a ring; and
$Q_5$ and $Q_6$ are optionally bonded together to form a ring.

3. The leaving substituent-containing compound according to claim 2, wherein the structure represented by Formula (III) is a structure represented by the following Formula (IV) or (V):

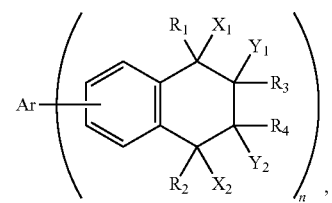

Formula (IV)

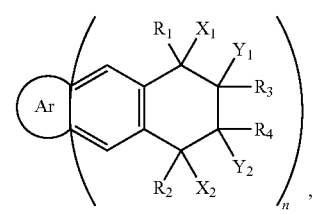

Formula (V)

wherein:
n is an integer of 1 or more, and when n is an integer of 2 or greater, a plurality of substituents in parentheses are optionally identical or different;
Ar represents an aryl group optionally having a substituent or a heteroaryl group optionally having a substituent; and
Ar is linked through a covalent bond with or ring-fused with a skeleton of a cyclohexene derivative.

4. The leaving substituent-containing compound according to claim 3, wherein Ar is at least one selected from the group consisting of an aromatic hydrocarbon ring, an aromatic heterocyclic ring, a group in which one or more aromatic hydrocarbon rings are ring-fused with one or more aromatic heterocyclic rings, a group in which two or more aromatic hydrocarbon rings are ring-fused together, a group in which two or more aromatic heterocyclic rings are ring-fused together, a group in which one or more aromatic hydrocarbon rings are linked through a covalent bond with one or more aromatic heterocyclic rings, a group in which two or more aromatic hydrocarbon rings are linked together through a covalent bond, and a group in which two or more aromatic heterocyclic rings are linked together via a covalent bond.

* * * * *